(12) United States Patent
Fischetti et al.

(10) Patent No.: US 7,582,729 B2
(45) Date of Patent: Sep. 1, 2009

(54) NUCLEIC ACIDS AND POLYPEPTIDES OF $C_1$ BACTERIOPHAGE AND USES THEREOF

(75) Inventors: Vincent Fischetti, West Hempstead, NY (US); Daniel Nelson, New York, NY (US); Raymond Schuch, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 10/556,359

(22) PCT Filed: May 14, 2004

(86) PCT No.: PCT/US2004/015052

§ 371 (c)(1),
(2), (4) Date: Mar. 15, 2007

(87) PCT Pub. No.: WO2004/104213

PCT Pub. Date: Dec. 2, 2004

(65) Prior Publication Data

US 2007/0265198 A1    Nov. 15, 2007

(51) Int. Cl.
*C07K 14/00* (2006.01)
(52) U.S. Cl. .................................................... 530/350
(58) Field of Classification Search ........................ None
See application file for complete search history.

(56) References Cited

U.S. PATENT DOCUMENTS

| 6,056,955 | A  | * | 5/2000  | Fischetti et al. | ............ | 424/94.1 |
| 6,326,002 | B1 | * | 12/2001 | Fischetti et al. | ............ | 424/94.1 |
| 6,608,187 | B2 | * | 8/2003  | Nelson et al.    | ............ | 536/23.1 |

FOREIGN PATENT DOCUMENTS

WO    WO 01/19391    *    3/2001

OTHER PUBLICATIONS

GenBank Accession No. NC_004814 (submitted Jan. 7, 2003).*
Nelson et al., Prevention and elimination of upper respiratory colonization of mice by group A streptococci by using a bateriophage lytic enzyme, PNAS, 2001, 98(7):4107-4112.*

* cited by examiner

*Primary Examiner*—Gary B Nickol
*Assistant Examiner*—Nicole Kinsey White

(57) ABSTRACT

The full-length nucleic acid sequence of the $C_1$ bacteriophage is disclosed in the present application. The specific regions of the $C_1$ genome encoding the PlyC lysin have also been identified and sequenced. The invention relates to the pharmaceutical and diagnostic utility of these sequences and provides for development of pharmaceutical compositions for treating or preventing streptococcal infections in mammals, for compositions for decontamination of inanimate surfaces and for diagnosis of streptococcal infections.

2 Claims, 9 Drawing Sheets

A.

B.

C.

NUCLEIC ACIDS AND POLYPEPTIDES OF C$_1$ BACTERIOPHAGE AND USES THEREOF

FIELD OF THE INVENTION

The invention relates to novel nucleic acids and proteins isolated from C$_1$ bacteriophage and therapeutic and diagnostic uses of these nucleic acids and polypeptides and related pharmaceutical compositions useful in treating Streptococcal infections. The invention further relates to the identification, isolation and cloning of specific genes from the C$_1$ bacteriophage, specifically the C$_1$ bacteriophage lysin, termed PlyC, and the use of these genes and gene products for prophylactic and therapeutic use to treat or prevent Streptococcal infections, and to aid in diagnosis of infections caused by Streptococcus.

BACKGROUND OF THE INVENTION

Group C streptococci are a common cause of infection in several animal species but are generally considered to be a rare cause of infection in humans (Ghoneim, A. T. et al. (1980), J. Clin. Pathol. 33:188-190; Feldman, W. E. Postgrad. Med. (1993), 93(3): 141-145). Of the four species of group C streptococci, *S. equisimilis* has been reported to cause most human illnesses, including bacteremia, endocarditis, meningitis, pneumonia, epiglottitis, puerperal sepsis, and wound infections. However, *S. zooepidemicus* has been associated with two outbreaks of pharyngitis and nephritis in Europe (Duca, E. et al. (1969), J. Hyg. Camb. 67: 691-698; Barnham, M. et al. (1983), Lancet 8331: 945-948). In both of the European outbreaks, unpasteurized milk was suspected as the source of infection. More recently, Group C streptococci was identified as a causative agent in a prosthetic joint infection (Kleshinski, J. et al. (2000) Southern Medical Journal 93:1217-1220). This is the first reported outbreak in the United States and is the first such reported outbreak in which the vehicle, ie. cheese made from unpasteurized cows' milk, has been epidemiologically implicated. Although *S. zooepidemicus* and *S. equisimilis* are rarely reported causes of mastitis in cows, the cause of this outbreak was contaminated milk from cows with mammary infections due to *S. zooepidemicus*.

Group C streptococci are also the causative agent of strangles, a highly contagious and serious infection of horses and other equids. The disease is characterized by severe inflammation of the mucosa of the head and throat, with extensive swelling and often rupture of the lymph nodes, which produces large amounts of thick, creamy pus. The organism can be isolated from the nose or lymph nodes of affected animals, and is usually readily identified in the laboratory by simple sugar tests.

Control of the disease is complicated by the development of long-term carriers that outwardly appear healthy and are frequently difficult to detect because swab samples from them often do not yield cultures of *S. equi*. The organism resides in the guttural pouches and resumption of active shedding can recur sporadically for unknown reasons. Previously, endoscopy was the only way to reliably detect most carriers but this is too impractical in most circumstances. The outbreak prevalence of these carriers combined with movement and mixing with susceptible animals probably accounts for the high incidence of strangles. Although a "PCR test" to detect the DNA of the organism in nasopharyngeal swabs is now available, enabling sensitive carrier detection, there are still practical difficulties and expense with multiple nasal sampling and some endoscopy, although much less than previously. For the large majority of horses the most effective means of controlling strangles would be a good vaccine or other immunogenic compositions that are effective in eliminating the causative agent.

Group A *Streptococcus* (*Streptococcus pyogenes*), the primary etiologic agent of bacterial pharyngitis, is one of few human pathogens that remain uniformly sensitive to penicillin (Macris, M. H., et al. (1998) Pediatr. Infect. Dis. J. 17:377-381). Additionally, the advent of rapid group A streptococcal diagnostic test kits over the last decade has allowed early initiation of antibiotic treatment. Despite these factors, streptococcal-mediated pharyngitis is reported in over 2.5 million people annually in the United States with >80% of these cases occurring in children under 15 years of age (Schappert, S. M., et al. (1999) Vital Health Stat. 13). However, streptococcal pharyngitis classically is not a reportable disease and it has been speculated that the documented number of these pharyngitis cases may be considerably underestimated. Additionally, penicillin fails to completely eradicate streptococci in up to 35% of patients treated for pharyngitis (Pichichero, M. E. (1998) Pediatr. Rev. 19:291-302) and carriage rates as high as 50% have been reported in close contact areas such as day care centers (Feldman, S., et al. (1987) J. Pediatr. 110:783-787). This high carriage rate contributes to the spread of streptococcal pharyngitis (Nguyen, L., et al. (1997) J. Clin. Microbiol. 35:2111-2114) and correlates with outbreaks of rheumatic fever (Oliver, C. (2000) J. Antimicrob. Chemother. 45 Topic T1:13-21). While eradication of the carrier state would reduce the pool of streptococci in the population, and thus streptococcal-related diseases, to date the only treatment is an extensive regimen of antibiotics (Tanz, R. R., et al. (1998) Pediatric Annals 27:281-285) that may increase streptococcal resistance to macrolides, which are often prescribed for patients with penicillin allergies (York, M. K., et al. (1999) J. Clin. Microbiol. 37:1727-1731).

Bovine mastitis is an inflammation of a cow's mammary gland, usually due to a microbial infection originating from contaminated teats. Experimental bovine mastitis can be induced with as little as 100 organisms, so a few chronic infections within a herd can maintain a persistent bacterial reservoir. Several bacterial species have the ability to cause bovine mastitis, including *Staphylococcus aureus, Streptococcus uberis, Streptococcus agalactiae* (Group B strep), and *Escherichia coli*. Of these, *S. aureus*, which causes acute conditions, and *S. uberis*, which causes chronic conditions, are responsible for the bulk of bovine mastitis cases. The persistence and economic impact of bovine mastitis is alarming. Wilson et al. (Wilson, D. J., et al. (1997) J. Dairy Sci. 80:2592-2598) recently published the results of a retrospective study of milk samples collected from more than 100,000 cows in New York and northern Pennsylvania between 1991 and 1995. They found that intramammary infections were present in 36% of cows enrolled in the Dairy Herd Improvement Association. This disease is estimated to cost the producer approximately $200/cow/year, which corresponds to a U.S. total of $1.7 billion annually.

Current therapies for bovine mastitis rely heavily on the use of β-lactam antibiotics such as penicillins and cephalosporins. These agents have had a beneficial impact on dairy-animal health and milk production. However, the cure rate for treatment of some infections, particularly *S. aureus*, is often less than 15%. This is attributed to incomplete penetration of the antibiotics throughout the mammary gland (Yancey, R. J., et al. (1991) Eur. J. Clin. Microbiol. Infec. Dis. 10:107-113). Additionally, concerns of accidental exposure of susceptible consumers to residual antibiotics resulting in anaphylaxis has necessitated the imposition of a post-treatment milk discard period and strict industry surveillance of all milk shipments.

While infections can be cleared in days with antibiotic treatment, the discard period can often last weeks until residual antibiotic levels fall within acceptable parameters. Finally, there is growing concern that the agricultural use of antibiotics contributes to the emergence of antibiotic resistance in human pathogens (Smith, D. L., et al. (2002) Proc. Natl. Acad. Sci. U.S.A. 99:6434-5439). Taken together, these concerns suggest alternative therapies are needed for the therapeutic management of bovine mastitis.

Tailed bacteriophages are the most populous "organism" on Earth with roughly $10^{30}$ inhabitants in the biosphere (Brussow, H. et al. (2002) Cell 108:13-16). However, we are just beginning to appreciate the role they play in bacterial diversity (Hendrix, R. W. et al. (1999) Proc. Natl. Acad. Sci. U.S.A. 96:2192-2197) and more recently, bacterial pathogenesis (Broudy, T. B. et al. (2003) Infect. Immun. 71:3782-3786; Wagner, P. L. et al. (2002) Infect. Immun. 70:3985-3993). Indeed, whole genome sequencing of two different strains of group A streptococci reveals that polylysogenic phage represent the only diversity between the two strains (Beres, S. B. et al. (2002) Proc. Natl. Acad. Sci. U.S.A. 99:10078-10083; Ferretti, J. J. et al. (2001) Proc. Natl. Acad. Sci. U.S.A. 98:4658-4663). Recent advances have allowed whole bacteriophage genomes of evolutionary or biological interest to be rapidly sequenced for comparison to known genomes.

The streptococcal $C_1$ bacteriophage has roots at the forefront of bacteriophage research. Shortly after the discovery of bacteriophages by Twort and d'Herelle (Twort, F. W. (1915) Lancet ii.: 1241-1243; d'Herelle, F. H. (1917) C. R. Acad. Sci. (Paris) 165:373-375), the $C_1$ bacteriophage was isolated by Clark in 1925 from a sewage plant in Milwaukee, Wis. and represents the first documented bacteriophage found to be active on any type of streptococci (Clark, P. F. et al. (1926) J. Bacteriol. 11:89). Initially known as the "sludge" phage or "Clark" phage, it infected streptococci isolated from animals (which we now know to be group C streptococci), but not streptococci found in humans (now known to be group A streptococci) (Shwartzman, G. (1927) J. Exp. Med. 46-497-509; Lancefield, R. C. (1932) Proc. Soc. Exp. Biol. Med. 30:169-171). In a hallmark 1934 paper, Alice Evans, using the "Clark" phage which she renamed B563, was the first person to utilize phage in order to classify bacterial strains, thus founding the analytical field of phage typing (Evans, A. C. (1934) Public Health Reports 49:1386-1401). Additionally, Evans noticed that phage lysates had lytic activity on streptococci that were not sensitive to the phage itself. She called this phenomenon "nascent lysis" and attributed it to a "lysin" activity originally defined by Twort (Twort, F. W. (1925) Lancet ii.:642-644). In 1957, Krause renamed the Evans B563 phage, $C_1$, to imply an exquisite specificity for group C streptococci (Krause, R. M. (1957) J. Exp. Med. 106:365-384). Krause also noted that the $C_1$ cell wall hydrolase, or lysin, had a less restrictive range given that groups A, C, and E streptococci were rapidly lysed by this enzyme.

On the genetic level, the $C_1$ phage has not been studied in detail. Two published restriction maps of this genome exist (Pomrenke, M. E. et al. (1989) J. Basic Microbiol. 6:395-398; Totolian, A. A. et al. (1981) Reedbooks Ltd., Surrey), but to date, no sequence data was available. The majority of interest in this phage involves its lysin, which has been used extensively as a tool to dissolve the streptococcal cell wall in order to make protoplasts, extract genomic DNA, or to study surface proteins (van de Rijn, I. et al. (1981) Infect. Immun. 32:86-91; Wheeler, J. et al. (1980) J. Gen. Microbiol. 120:27-33).

At the end of a bacteriophage lytic cycle in a sensitive bacterial host, all double stranded DNA bacteriophages produce a lytic system that consists of a holin and at least one peptidoglycan hydrolase, or "lysin", capable of degrading the bacterial cell wall. Lysins can be endo-β-N-acetylglucosaminidases or N-acetylmuramidases (lysozymes), which act on the sugar moiety, endopeptidases which cleave the peptide cross bridge, or more commonly, an N-acetylmuramoyl-L-alanine amidase, which hydrolyzes the amide bond connecting the sugar and peptide constituents. Typically, the holin is expressed in the late stages of phage infection forming a pore in the cell membrane allowing the lysin(s) to gain access to the cell wall peptidoglycan resulting in release of progeny phage (for review, see (Young, R. (1992) Microbiol. Rev. 56:430-481)). Lysin, added to sensitive organisms in the absence of bacteriophage, lyses the cell wall producing a phenomenon known as "lysis from without".

The $C_1$ bacteriophage specifically infect group C streptococci and produce a lysin (termed PlyC) that has been partially purified and characterized (Fischetti, V. A., et al. (1971) J. Exp. Med. 133:1105-1117; Raina, J. L. (1981) J. Bacteriol. 145:661-663). $C_1$ phage lysin can cause "lysis from without" in groups A and E streptococci as well as group C streptococci (Maxted, W. R. (1957) J. Gen. Microbiol. 16:584-594; Krause, R. M. (1957) J. Exp. Med. 106:365-384). Additionally, PlyC works on *Streptococcus equi* and *Streptococcus uberis*. This unique activity has been exploited as a tool in group A streptococcal studies to isolate surface molecules including M proteins (Fischetti, V. A., et al. (1985) J. Exp. Med. 161:1384-1401), to lyse cells for DNA extraction, and to make protoplasts when used in a hypertonic environment (Wheeler, J., et al. (1980) J. Gen. Microbiol. 120:27-33).

The present invention provides alternate means for the prevention and/or treatment of pathogenic streptococcal infections in humans and animals such as streptococcal pharyngitis, equine Strangles disease, bovine mastitis, and other disease states associated with groups A, C, and E streptococci as well as *S. equi* and *S. uberis*. Furthermore, the present invention provides the means for diagnosis of such pathogenic infections.

SUMMARY OF THE INVENTION

The present invention relates to the isolation and elucidation of the nucleic acid and protein sequence of $C_1$ bacteriophage, which is specific for Group C streptococci, and the therapeutic and diagnostic uses of these nucleic acid and polypeptide sequences. Furthermore, several open reading frames have been identified for which functions have been assigned. In a more particular aspect of the invention, the open reading frames associated with the two subunits of the PlyC (lysin) enzyme have been identified. Previous studies had demonstrated that the lytic properties associated with an isolated lysin had therapeutic potential to eliminate streptococcal colonization (Nelson et al. (2001) Proc. Nat. Acad. Sci. USA. 98:4107-4112). The available sequence data now provides the means by which such therapeutic and diagnostic utility can be carried out.

Accordingly, a first aspect of the invention provides for the isolation and elucidation of the full length nucleic acid sequence of $C_1$ bacteriophage, provided herein as SEQ ID NO: 21 (GenBank accession No.AY212251). More specifically, the $C_1$ bacteriophage contains a double-stranded, linear sequence of DNA with 16,687 base pairs, and a G+C content of 34.6%. Also present are 143 base pair inverted terminal repeats. Furthermore, 20 predicted open reading frames (ORFs) have been identified, described herein in Table III as SEQ ID NOs: 1-20, with the first 11 on the positive strand and the remaining 9 on the negative strand. The majority of the ORF-encoded proteins are dissimilar to known phage proteins and have no homology to any proteins contained in GenBank. Further analysis of the bacteriophage $C_1$ DNA revealed a terminal protein (TP) covalently linked to the 5' terminus of the DNA. The scientific evidence for the novel sequences and potential therapeutic and diagnostic utility of these sequences is provided below.

A second aspect of the invention provides for identification and elucidation of the nucleic acid and protein sequence of the multimeric PlyC (lysin). In a specific embodiment, the PlyC has two open reading frames (ORF 9 and ORF 11) and comprises a light chain (ORF 9) and heavy chain (ORF 11) subunits, the amino acid sequences both of which are provided herein as SEQ ID NOs: 9 and 11, respectively. Note, the light chain is now referred to as PlyC-B, although it was formerly called the PlyC alpha subunit (Nelson, D., et al. (2003) J. Bacteriol. 185:3325-3332). Likewise, the heavy chain is now referred to as PlyC-A, although it was formerly called the PlyC beta subunit. In a yet further embodiment, the PlyC may further comprise the polypeptide of SEQ ID NO: 10 (ORF 10). In a yet further embodiment, the PlyC orf 9 codes for a protein that is 8 kDa in size and the PlyC orf 11 codes for a protein that is 50 kDa in size. In a particular embodiment, the polypeptide comprises at least two subunits, the subunits comprising a PlyC lysin light chain (PlyC-B) and a PlyC lysin heavy chain (PlyC-A). In a further embodiment, the polypeptide comprises multiple copies of one or both subunits and fragments, mutants, variants, analogs or derivatives thereof. Particularly, since the native protein has an apparent molecular weight of 100 kDa as measured by gel filtration, a further embodiment of the invention provides for native PlyC to be a "multimer", composed of multiple copies of the heavy subunit (ORF 11), or the light subunit (ORF 9), or both light and heavy subunits. More specifically, this embodiment provides for PlyC to be preferably composed, but not limited to one heavy subunit (ORF 11) and 5 or 6 light subunits (ORF 9). A further embodiment provides that the operon containing the PlyC gene(s) is referred to as plyC (SEQ ID: 25). plyC is a 2.2 kb sequence containing the genes plyCA (SEQ ID: 23), lil (SEQ ID: 24), plyCB (SEQ ID: 22), and ~200 bp of untranslated sequence on both ends (See FIG. 2). It is envisioned that the multimeric PlyC may be used for treating or preventing bacterial infections, comprising administering a therapeutically effective amount of the PlyC multimer. In a yet further embodiment of the invention, the PlyC multimer is prepared as a pharmaceutical composition with a pharmaceutically acceptable carrier for use in treating bacterial infections, including infections caused by pathogenic streptococci of Groups A, C and E, as well as *S. uberis,* and *S. equi.* It is envisioned that the composition comprising the multimeric PlyC may be useful in treating streptococcal infections in mammals, including, but not limited to, horses and cows. A further embodiment provides for use of the pharmaceutical compositions for treatment of bovine mastitis in cows and strangles in horses. A yet further embodiment includes the use of the pharmaceutical compositions comprising multimeric PlyC for treatment of humans. A yet further embodiment provides for the use of the pharmaceutical compositions for treatment of streptococcal pharyngitis. A yet further embodiment provides for the use of the polypeptides of the present invention, that is, the C1 bacteriophage PlyC lytic enzyme, including the PlyC heavy and light chain subunits and multiple copies of one or the other subunits and fragments, mutants, variants, analogs or derivatives thereof for the preparation of a medicament for the treatment of a bacterial infection. In another preferred embodiment, the invention provides for the use of the polypeptides of the present invention, that is, the C1 bacteriophage PlyC lytic enzyme, including the PlyC heavy and light chain subunits and multiple copies of one or the other subunits and fragments, mutants, variants, analogs or derivatives thereof for the preparation of a medicament for the treatment of streptococcal infections selected from the group consisting of group A, E, C, *S. uberis* and *S. Equi.*

A third aspect of the invention provides for the generation of antibodies specific for the PlyC multimer. In a preferred embodiment, the antibodies are monoclonal antibodies specific for the PlyC multimer, or subunits or fragments thereof. In a yet further embodiment, the antibodies are polyclonal antibodies prepared in mice, rats, guinea pigs, rabbits, goats, sheep, horses, pigs, cows, or any other mammal generally used in the art for generation of polyclonal antibodies. In another embodiment, the antibodies may be chimeric antibodies, humanized antibodies, single chain antibodies or fragments thereof. A further embodiment provides for an immortal cell line that produces a monoclonal antibody that is specific for the multimeric PlyC or subunits or fragments thereof.

A fourth aspect of the invention provides for methods of diagnosing the presence of a pathogenic streptococcal infection. In a preferred embodiment, the binding domain of PlyC is labeled with a fluorescent chemical or protein using methods known to those skilled in the art and the labeled PlyC is then incubated directly with a sample taken from a subject suspected of harboring a pathogenic streptococci. The observation of fluorescence in the sample is indicative of the presence of a pathogenic streptococcal infection. A yet further embodiment provides for the use of the PlyC multimer in a luciferin-luciferase assay to aid in diagnosing pathogenic streptococcal infections. In this assay format, a sample suspected of harboring a pathogenic *streptococcus* is incubated directly with the PlyC multimer. If the sample contains a pathogenic *streptococcus,* the PlyC will bind to the bacteria, resulting in lysis of the bacteria and subsequent release of ATP or other components normally present in the cytoplasm of the bacterial cell, such as enzymes. The lysate is then tested in a luciferin-luciferase assay. In another embodiment, the sample suspected of harboring a pathogenic *streptococcus* may be added directly to the PlyC multimer concurrently with luciferin-luciferase without the need to collect the cell lysate first before adding it to the luciferin-luciferase. If a pathogenic *streptococcus* is present in the sample, the release of ATP from the lysed bacteria will trigger a positive reaction in the luciferin-luciferase system, resulting in release of measurable light from the reaction mixture.

One further embodiment of the invention may use an antibody to the PlyC multimer or subunits or fragments thereof, or antibodies may be prepared to any of the proteins listed in Table III as SEQ ID NOs: 1-20, and the antibody may be labeled (eg. with fluorescein or other known fluorescent proteins or chemicals), coupled to the bacteriophage protein and used to monitor binding of the specific protein to the bacteria in a patient sample, thus aiding in detection of pathogenic streptococci. Alternatively, any one of the proteins from Table III may be fluorescein labeled directly and used to detect the presence of pathogenic streptococci in a patient sample.

Further diagnostic testing formats, including ELISA assays or radioimmunoassays may also be contemplated for use with the present invention. In these formats, one can utilize the proteins identified in Table III directly or one may prepare antibodies to these proteins as noted herein for use in kits to monitor the presence of pathogenic streptococci in a patient sample. The procedures for ELISA or radioimmunoassays are known to those skilled in the art.

A fifth aspect of the invention provides for methods of preventing or treating bacterial infections comprising administering a therapeutically effective dose of a composition comprising a therapeutically effective amount of the PlyC multimer having a sequence as set forth in SEQ ID NOs: 9 and 11. A particular embodiment comprises methods for preventing or treating bacterial infections comprising administering a therapeutically effective dose of a composition containing the amino acid sequences as set forth in SEQ ID NOs: 9 and 11, further comprising a therapeutically effective amount of the polypeptide having the amino acid sequence as set forth in SEQ ID NO: 10. A specific embodiment provides that the PlyC multimer is composed of gene products of the plyC operon (SEQ ID NO: 25).

A sixth aspect of the invention provides for pharmaceutical compositions comprising a therapeutically effective amount of the PlyC multimer as set forth is SEQ ID NOs: 9 and 11 and a pharmaceutically acceptable carrier. A further embodiment provides for a pharmaceutical composition comprising a therapeutically effective amount of the PlyC multimer as set forth is SEQ ID NOs: 9 and 11 and further comprising a therapeutically effective amount of the polypeptide having the amino acid sequence as set forth in SEQ ID NO: 10. A specific embodiment may include a pharmaceutical composition designed for use in treatment of infections caused by *streptococcus* groups A, E and C, as well as *S. uberis,* and *S. equi.* Another embodiment may include a pharmaceutical composition designed for use in treatment of topical or systemic infections, or infections that are non-responsive to other antibiotic modalities. A yet further embodiment provides for veterinary use of the pharmaceutical compositions of the present invention. A preferred embodiment is for use in treating infections in mammals, including but not limited to, horses or cows. A yet further embodiment is use of the pharmaceutical compositions for treatment of human subjects. Another embodiment provides for a composition comprising the polypeptides of the present invention, that is, the C1 bacteriophage PlyC lytic enzyme, including the PlyC heavy and light chain subunits and multiple copies of one or the other subunits and fragments, mutants, variants, analogs or derivatives thereof for use in decontaminating inanimate surfaces to eliminate possible contamination with streptococci from Groups A, E, and C, as well as *S. uberis* and *S. equi.* In a particular embodiment, the composition may be used to decontaminate milking, dairy, and agricultural equipment from streptococci.

A seventh aspect of the invention provides for the identification and use of a particular polypeptide comprising the amino acid sequence for the holin polypeptide of bacteriophage C1. In a particular embodiment, the amino acid sequence for the holin is identified as SEQ ID NO: 8. It is envisioned that the holin may be utilized to better understand the biochemical aspects of bacterial lysis and may be used either to identify agents useful for antimicrobial therapy or for use in the diagnosis of streptococcal infections.

An eighth aspect of the invention provides for the identification and use of a particular polypeptide comprising the amino acid sequence for the major tail polypeptide of bacteriophage $C_1$. In a particular embodiment, the amino acid sequence for the major tail polypeptide is identified as SEQ ID NO: 12. It is envisioned that the major tail polypeptide may be utilized to better understand the biochemical aspects of binding of the bacteriophage to the bacterial cell wall. Thus, this polypeptide may be used either to aid in identification of agents useful for antimicrobial therapy or for use in the diagnosis of streptococcal infections.

A ninth aspect of the invention provides for the identification and use of a particular polypeptide comprising the amino acid sequence for the major capsid polypeptide of bacteriophage $C_1$. In a particular embodiment, the amino acid sequence for the major capsid polypeptide is identified as SEQ ID NO: 16. It is envisioned that the major capsid polypeptide may be utilized to better understand the biochemical aspects of binding of the bacteriophage to the bacterial cell wall. Thus, this polypeptide may be used either to aid in identification of agents useful for antimicrobial therapy or for use in the diagnosis of streptococcal infections.

Other advantages of the present invention will become apparent from the ensuing detailed description taken in conjunction with the following illustrative drawings.

DETAILED DESCRIPTION

Figure 1:
FIG. 1. Elucidation of subunits for PlyC. (A) Native-PAGE of purified PlyC shows a single, homogeneous band. (B) The native-PAGE was placed on an group A streptococcal-embedded agarose and allowed to incubate for 2 hr before the native gel was removed. The clearing zone on the agarose indicated that the PlyC activity corresponds to the single band on the native-PAGE. (C) An SDS-PAGE of the purified PlyC used in figure A shows that PlyC is composed of 2 subunits. The 50 kDa heavy chain is now termed PlyC-A and the 8 kDa light chain is termed PlyC-B. N-terminal sequencing of the native-PAGE gave a double sequence, which corresponded to the two chains sequenced in the SDS-PAGE (see text for details).
Figure 1:
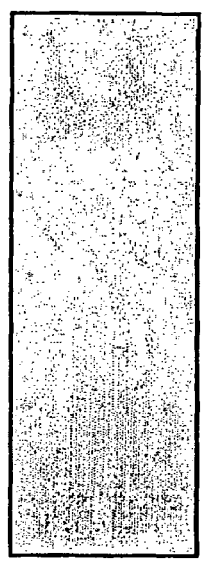
Figure 1:
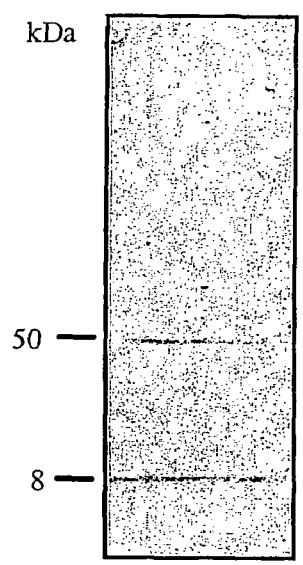

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entirety.

Definitions

"Treatment" refers to the administration of medicine or the performance of medical procedures with respect to a patient, for either prophylaxis (prevention) or to cure the infirmity or malady in the instance where the patient is afflicted.

The term "antibody" as used herein includes intact molecules as well as fragments thereof, such as Fab and F(ab')$_2$, which are capable of binding the epitopic determinant. The antibodies may be monoclonal, polyclonal, chimeric, humanized, or single chain antibodies, or fragments thereof. Antibodies that bind multimeric PlyC, or subunits or fragments thereof, can be prepared using intact dimers, polypeptides or fragments-containing small peptides of interest as the immunizing antigen attached to a carrier molecule. Commonly used carriers that are chemically coupled to peptides include bovine serum albumin and thyroglobulin. The coupled peptide is then used to immunize the animal (e.g, a mouse, rat or rabbit).

A "therapeutically effective amount" or "therapeutically effective dose" is an amount or dose sufficient to decrease, prevent or ameliorate the symptoms associated with the bacterial infection.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

"Analog" as used herein, refers to a nucleotide, a protein, or a polypeptide that possesses similar or identical activity or function(s) as the nucleotide, protein or polypeptide having the desired activity and therapeutic effect of the present invention (eg. having the ability to prevent or treat streptococcal infections or to aid in the diagnosis of streptococcal infections), but need not necessarily comprise a sequence that is similar or identical to the sequence of the preferred embodiment, such as that of SEQ ID NOS: 21 or 9 or 11, or possess a structure that is similar or identical to that of SEQ ID NOS: 21 or 9 or 11. As used herein, a nucleic acid or nucleotide sequence, or an amino acid sequence of a protein or polypeptide is "similar" to that of a nucleic acid, nucleotide or protein or polypeptide having the desired activity if it satisfies at least one of the following criteria: (a) the nucleic acid, nucleotide, protein or polypeptide has a sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleic acid, nucleotide, protein or polypeptide sequences having the desired activity as described herein (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of the AAPI; or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the polypeptides of the present invention having the desired therapeutic effect. As used herein, a polypeptide with "similar structure" to that of the preferred embodiments of the invention refers to a polypeptide that has a similar secondary, tertiary or quarternary structure as that of the preferred embodiment. The structure of a polypeptide can determined by methods known to those skilled in the art, including but not limited to, X-ray crystallography, nuclear magnetic resonance, and crystallographic electron microscopy.

"Derivative" refers to either a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide protein or polypeptide possesses a similar or identical function as the parent polypeptide.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

A "variant" (v) of polynucleotides or polypeptides, as the term is used herein, are polynucleotides or polypeptides that are different from a reference polynucleotide or polypeptide, respectively. Variant polynucleotides are generally limited so that the nucleotide sequence of the reference and the variant are closely related overall and, in many regions, identical. Changes in the nucleotide sequence of the variant may be silent. That is, they may not alter the amino acid sequence encoded by the polynucleotide. Where alterations are limited to silent changes of this type a variant will encode a polypeptide with the same amino acid sequence as the reference. Alternatively, changes in the nucleotide sequence of the variant may alter the amino acid sequence of a polypeptide encoded by the reference polynucleotide. Such nucleotide changes may result in amino acid substitutions, additions, deletions, fusions, and truncations in the polypeptide encoded by the reference sequence. Variant polypeptides are generally limited so that the sequences of the reference and the variant are that are closely similar overall and, in many regions, identical. For example, a variant and reference polypeptide may differ in amino acid sequence by one or more substitutions, additions, deletions, fusions, and truncations, which may be present or absent in any combination. Such variants can differ in their amino acid composition (e.g. as a result of allelic or natural variation in the amino acid sequence, e.g. as a result of alternative mRNA or pre-mRNA processing, e.g. alternative splicing or limited proteolysis) and in addition, or in the alternative, may arise from differential post-translational modification (e.g., glycosylation, acylation, phosphorylation, isoprenylation, lipidation).

A nucleic acid which is "hybridizable" to a nucleic acid of the present invention or to its reverse complement, or to a nucleic acid encoding a derivative, or to its reverse complement under conditions of low stringency can be used in the methods of the invention to detect the presence of a $C_1$ bacteriophage gene and/or presence or expression level of a $C_1$ gene product. By way of example and not limitation, procedures using such conditions of low stringency are as follows (see also Shilo and Weinberg, 1981, Proc. Natl. Acad. Sci. U.S.A. 78, 6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency that may be used are well known in the art (e.g., as employed for cross-species hybridizations).

A nucleic acid which is "hybridizable" to an $C_1$ bacteriophage nucleic acid (e.g., having a sequence as set forth in SEQ ID NO: 21 or to its reverse complement, or to a nucleic acid encoding a derivative thereof, or to its reverse complement under conditions of high stringency) is also provided for use in the methods of the invention. By way of example and not limitation, procedures using such conditions of high-stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filter is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency that may be used are well known in the art.

A nucleic acid which is "hybridizable" to a $C_1$ bacteriophage nucleic acid (e.g., having a sequence as set forth in SEQ ID NO: 21 or to its reverse complement, or to a nucleic acid encoding a derivative thereof, or to its reverse complement under conditions of moderate stringency) is also provided for use in the methods of the invention. For example, but not limited to, procedures using such conditions of moderate stringency are as follows: filters comprising immobilized DNA are pretreated for 6 hours at 55° C. in a solution containing 6×SSC, 5× Denhardt's solution, 0.5%. SDS and 100 µg/ml denatured salmon sperm DNA. Hybridizations are carried out in the same solution with 5-20×10$^6$ cpm $^{32}$P-labeled probe. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Washing of filters is done at 37° C. for 1 hour in a solution containing 2×SSC, 0.1% SDS. Other conditions of moderate stringency that may be used are well known in the art. (see, e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols,® 1994-1997 John Wiley and Sons, Inc.).

General Description

The $C_1$ phage is currently classified as a member of the *Podoviridae* family of bacteriophage based on its physical appearance of short, non-contractile tails. This designation makes the $C_1$ phage a tempting choice to sequence for several reasons. First, the *Podoviridae* represent a diverse set of phage where only a few sequenced genomes exist and even fewer have been studied in detail. Additionally, both the historical interest of the $C_1$ phage and the current medical implications of its lysin warrant further investigation. Taken together, the $C_1$ genome is an ideal candidate for genomic sequencing and characterization presented herein;

Accordingly, the present invention provides methods for the elucidation of the nucleic acid and protein sequence of $C_1$ bacteriophage, which is specific for Group C streptococci, and the therapeutic and diagnostic uses of these nucleic acid and polypeptide sequences. The invention further provides for the full-length nucleic acid sequence of $C_1$ bacteriophage, as set forth in SEQ ID NO: 21. More specifically, the $C_1$ bacteriophage contains a double-stranded, linear sequence of DNA with 16,687 base pairs, and a G+C content of 34.6%. Also present are 143 base pair inverted terminal repeats. Furthermore, 20 open reading frames (orfs), have been identified and some of the functions of the polypeptides encoded by these nucleic acids have been determined. These are described herein in Table III as SEQ ID NOs: 1-20, with the first 11 on the positive strand and the remaining 9 on the negative strand. The majority of the ORF-encoded proteins are dissimilar to known phage proteins and have no homology to any proteins contained in GenBank. Further analysis of the bacteriophage $C_1$ DNA revealed a terminal protein (TP) covalently linked to the 5' terminus of the DNA.

Previous studies demonstrated that the lytic properties associated with an isolated lysin had therapeutic potential to eliminate streptococcal colonization (Nelson et al. (2001) Proc. Nat. Acad. Sci. USA. 98:4107-4112). The available sequence data now provides the means by which such therapeutic and diagnostic utility can be carried out. Accordingly, in a more particular aspect of the invention, the open reading frames associated with the two subunits of the PlyC (lysin) enzyme have been identified. The amino acid sequences of the two subunits have been elucidated and are described herein as SEQ ID NOs: 9 and 11. The DNA sequences encoding the light chain (plyCB) and heavy chain (plyCA) are set forth as SEQ ID NOs: 22 and 23, respectively. The PlyC orf9 codes for a protein that is 8 kDa in size (light chain) and the PlyC orf 11 codes for as protein that is 50 kDa in size (heavy chain). Furthermore, since the native protein has an apparent molecular weight of 100 kDa as measured by gel filtration, a further embodiment of the invention provides for a PlyC multimer composed of multiple copies of the heavy subunit (ORF 11), the light subunit (ORF 9), or both subunits; More preferably, this embodiment provides, but is not limited to, one heavy subunit (ORF 11) and 5 or 6 light subunits (ORF 9). The DNA sequences contained in the plyC operon (SEQ ID NO: 25) include both of the PlyC genes, plyCB and plyCA, as well as untranslated regions thought be involved in the transcriptional regulation. It is envisioned that the multimeric PlyC may be used for treating or preventing bacterial infections, comprising administration of a therapeutically effective amount of the PlyC multimer.

In a yet further embodiment of the invention, the PlyC multimer is prepared as a pharmaceutical composition with a pharmaceutically acceptable carrier for use in treating bacterial infections, including infections caused by pathogenic streptococci of Groups A, C and E, as well as *S. uberis,* and *S. equi.* It is envisioned that the composition comprising the multimeric PlyC may be useful in treating streptococcal infections in mammals, including, but not limited to, horses and cows. A further embodiment provides for use of the pharmaceutical compositions for treatment of bovine mastitis in cows and strangles in horses. A yet further embodiment includes the use of the pharmaceutical compositions comprising multimeric PlyC for treatment of humans. A yet further embodiment provides for the use of the pharmaceutical compositions for treatment of streptococcal pharyngitis.

A further aspect of the invention provides for the generation of antibodies specific for the PlyC multimer. In a preferred embodiment, the antibodies are monoclonal antibodies specific for the PlyC multimer, or subunits or fragments thereof. In a yet further embodiment, the antibodies are polyclonal antibodies prepared in mice, rats, guinea pigs, rabbits, goats, sheep, horses, pigs, cows, or any other mammal generally used in the art for generation of polyclonal antibodies. In another embodiment, the antibodies may be chimeric antibodies, humanized antibodies, single chain antibodies, or fragments thereof. A further embodiment provides for an immortal cell line that produces a monoclonal antibody that is specific for the multimeric PlyC or subunits or fragments thereof.

A yet further aspect of the invention provides for methods of diagnosing the presence of a pathogenic streptococcal infection. In a preferred embodiment, the binding domain of PlyC is labeled with a fluorescent chemical or protein and the labeled PlyC is then incubated directly with a sample taken from a subject suspected of harboring a pathogenic streptococci. The observation of fluorescence in the sample is indicative of the presence of a pathogenic streptococcal infection. A yet further embodiment provides for the use of the PlyC in a luciferin-luciferase assay to aid in diagnosing pathogenic streptococcal infections. In this assay format, a sample suspected of harboring a pathogenic *streptococcus* is incubated directly with the PlyC multimer. If the sample contains a pathogenic *streptococcus,* the PlyC will bind to the bacteria, resulting in lysis of the bacteria and subsequent release of ATP or other components normally present in the cytoplasm of the bacterial cell, such as enzymes. The lysate is then tested in a luciferin-lucifersase assay. In another embodiment, the sample suspected of harboring a pathogenic *streptococcus* may be added directly to the PlyC multimer concurrently with luciferin-luciferase without the need to collect the cell lysate first before adding it to the luciferin-luciferase. If a pathogenic *streptococcus* is present in the sample, the release of ATP from the lysed bacteria will trigger a positive reaction in the luciferin-luciferase system, resulting in release of measurable light from the reaction mixture.

Therapeutic Uses of the Invention

Another aspect of the invention provides for the use of the PlyC (lysin) multimer in treatment of bacterial infections or in prevention of bacterial cell growth in vitro and in vivo. One embodiment of the invention features use of the PlyC (lysin) multimer to treat infections caused by streptococci or to prevent growth of streptococci, in particular streptococci from group A, E or C as well as *S. uberis,* and *S. equi.* A further aspect of this invention provides for use of the PlyC lysin as a decontamination agent. A specific embodiment of this invention is to use PlyC to decontaminate milking equipment and teet dip cups of S. uberis.

The invention provides for treatment or prevention of various diseases and disorders by administration of PlyC multimer. The administration of PlyC multimer would be by way of a pharmaceutically acceptable carrier. The administration of PlyC multimer may be by way of the oral cavity or it may be delivered parenterally. The PlyC multimer may be administered for use as an anti-infective and may be delivered topically, mucosally or sublingually. For systemic infections, it may be delivered intravenously, intramuscularly, or subcutaneously.

In a further embodiment, treatment of infections of the upper respiratory tract can be prophylactically or therapeutically treated with a composition comprising an effective amount of the PlyC multimer, and a carrier for delivering the PlyC multimer to a mouth, throat, or nasal passage. It is preferred that the PlyC multimer is in an environment having a pH that allows for activity of multimeric PlyC. If an individual has been exposed to someone with an upper respiratory disorder, the PlyC multimer will reside in the mucosal lining and prevent any colonization of the infecting bacteria.

Means of application include, but are not limited to direct, indirect, carrier and special means or any combination of means. Direct application of the PlyC multimer may be by nasal sprays, nasal drops, nasal ointments, nasal washes, nasal injections, nasal packings, bronchial sprays and inhalers, or indirectly through use of throat lozenges, or through use of mouthwashes or gargles, or through the use of ointments applied to the nasal nares, the bridge of the nose, or the face or any combination of these and similar methods of application. The forms in which PlyC may be administered include but are not limited to lozenges, troches, candies, injectants, chewing gums, tablets, powders, sprays, liquids, ointments, and aerosols.

The lozenge, tablet, or gum into which the PlyC multimer is added may contain sugar, corn syrup, a variety of dyes, non-sugar sweeteners, flavorings, any binders, or combinations thereof. Similarly, any gum based products may contain acacia, carnauba wax, citric acid, corn starch, food colorings, flavorings, non-sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another embodiment of the invention, sugar substitutes are used in place of dextrose, sucrose, or other sugars.

The PlyC multimer may also be placed in a nasal spray, wherein the nasal spray is the carrier. The nasal spray can be a long acting or timed release spray, and can be manufactured by means well known in the art. An inhalant may also be used, so that the PlyC multimer may reach further down into the bronchial tract, including into the lungs.

Another composition and use of the PlyC multimer is for the therapeutic or prophylactic treatment of bacterial infections of burns and wounds of the skin. The composition comprises an effective amount of the PlyC multimer and a carrier for delivering the PlyC multimer to the wounded skin. The mode of application for the PlyC multimer includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes but is not limited to a smear, spray, a time-release patch, a liquid absorbed wipe, and combinations thereof. The PlyC multimer may be applied to a bandage either directly or in one of the other carriers. The bandages may be sold damp or dry, wherein the PlyC multimer is in a lyophilized form on the bandage. This method of application is most effective for the treatment of burns.

In a further embodiment wherein a bacteriocidal activity is desirable, the PlyC multimer is administered alone or in combination with one or more additional therapeutic compounds or treatments. In a preferred embodiment, the PlyC multimer can be administered to a human subject for therapy (e.g. to ameliorate symptoms or to retard onset or progression) of bacterial infections. One embodiment provides for treatment of streptococcal pharyngitis. A further embodiment provides for the PlyC lysin to be administered to non-human mammals, including but not limited to horses and cows. One embodiment provides for treatment of bovine mastitis or strangles in horses. Specific embodiments provide for pharmaceutical compositions comprising the PlyC multimer for administration to human subjects or non-human mammals, including but not limited to cows and horses. It is also envisioned that one embodiment may provide for treatment of mammals, including human subjects and non-human mammals, suffering from streptococcal infections and who are not responsive to more traditional modes of anti-microbial therapy. It is also envisioned that the PlyC multimer may be used for decontamination purposes, such as to decontaminate milking, dairy, and agricultural equipment from streptococci. It is also envisioned that the PlyC multimer may be administered along with other lytic enzymes or with other antibiotics or anti-microbial forms of therapy.

The PlyC multimers for use in therapy can be tested in suitable animal model systems prior to testing in humans, including but not limited to rats, mice, chicken, cows, horses, monkeys, rabbits, etc. For in vivo testing, prior to administration to humans, any animal model system known in the art may be used. In one embodiment, PlyC multimers are tested in non-human animals (e.g., mice, rats, monkeys, rabbits, and guinea pigs), preferably non-human animal models for streptococcal infectious diseases. In accordance with this embodiment, PlyC multimer is administered to the animals, and the effect of the PlyC multimers on microbial levels is determined in the infected animal. Active PlyC multimers can be identified by comparing the level of bacteria in a culture obtained from an animal or group of animals treated with PlyC multimers with the level of the bacteria in a culture obtained from an animal or group of animals treated with a control nucleic acid or protein.

In yet another embodiment, test compounds that modulate the activity of PlyC multimers are identified in human subjects having an infection associated with streptococcal bacteria. In accordance with this embodiment, a test compound or a control compound is administered to the human subject in conjunction with the PlyC multimer, and the effect of a test compound on either reduction in spread of the microbial infection, elimination of the bacterial infection or amelioration of symptoms associated with the Therapeutic and Prophylactic Compositions and Their Use The invention provides methods of treatment comprising administering to a subject an effective amount of the PlyC multimer. In a preferred aspect, the PlyC multimer is substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human.

In one specific embodiment, a non-human mammal is the subject. In another specific embodiment, a human mammal is the subject.

Various delivery systems are known and can be used to administer the PlyC multimer, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment, such as topical use on the skin; any suitable method known to the art may be used.

Another aspect of the invention provides for pharmaceutical compositions comprising the PlyC multimer for therapeutic use in treatment of bacterial infections. Moreover, a further embodiment may include a pharmaceutical composition designed for use in topical treatment of bacterial infections. Another embodiment may include a pharmaceutical composition designed for use in treatment of systemic infections, or infections that are non-responsive to other antibiotic modalities.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

Examples of suitable pharmaceutical carriers are described in "Remington's Pharmaceutical Sciences" by E. W. Martin. Such compositions will contain a therapeutically effective amount of the nucleic acid of $C_1$ bacteriophage or PlyC multimer, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the PlyC multimer which will be effective in the treatment of infectious diseases, can be determined by standard clinical techniques based on the present description. In addition, its vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In a specific embodiment, it may be desirable to administer the pharmaceutical compositions of the invention locally to the area in need of treatment; this may be achieved, for example, and not by way of limitation, by local infusion during surgery, by topical application, by injection, by means of a catheter, or by means of an implant, said implant being of a porous, non-porous, or gelatinous material, including membranes, such as sialastic membranes, or fibers or co-polymers such as Elvax (see Ruan et al, 1992, Proc Natl Acad Sci USA, 89:10872-10876). In one embodiment, administration can be by direct injection by aerosol inhaler.

In another embodiment, the PlyC multimer can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the PlyC multimer can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

Diagnostic Uses

A further aspect of the invention provides for methods of diagnosing a pathogenic streptococcal infection. In a preferred embodiment, the binding domain of PlyC is labeled with a fluorescent chemical or protein and the labeled PlyC is then incubated directly with a sample taken from a subject suspected of harboring a pathogenic streptococci. The observation of fluorescence in the sample is indicative of the presence of a pathogenic streptococcal infection. A yet further embodiment provides for the use of the PlyC in a luciferin-luciferase assay to aid in diagnosing pathogenic streptococcal infections. In this assay format, a sample suspected of harboring a pathogenic *streptococcus* is incubated directly with the PlyC multimer. If the sample contains a pathogenic *streptococcus*, the PlyC multimer will bind to the bacteria, resulting in lysis of the bacteria and subsequent release of ATP or other components normally present in the cytoplasm of the bacterial cell, such as enzymes. The lysate is then tested in a luciferin-luciferase assay. In another embodiment, the sample suspected of harboring a pathogenic *streptococcus* may be added directly to the PlyC multimer concurrently with luciferin-luciferase without the need to collect the cell lysate first before adding it to the luciferin-luciferase. If a pathogenic *streptococcus* is present in the sample, the release of ATP from the lysed bacteria will trigger a positive reaction in the luciferin-luciferase system, resulting in release of measurable light from the reaction mixture. In another embodiment, any other cytoplasmic markers, enzymes, proteins, cell wall fragments, or carbohydrates liberated by PlyC from streptococci could also be detected by any methodologies common to the diagnostic art.

Alternatively, one embodiment of the invention may use an antibody to the PlyC multimer or subunits or fragments thereof, or antibodies may be prepared to any of the proteins listed in Table III as SEQ ID NOs: 1-20, and the antibody may be labeled (eg. with fluorescein or other known fluorescent proteins or chemicals), coupled to the bacteriophage protein and used to monitor binding of the specific protein to the bacteria in a patient sample, thus aiding in detection of pathogenic streptococci. Alternatively, any one of the proteins from Table III may be fluorescein labeled directly and used to detect the presence of pathogenic streptococci in a patient sample.

Further diagnostic testing formats, including ELISA assays or radioimmunoassays may also be contemplated for use with the present invention. In these formats, one can utilize the proteins identified in Table III directly or one may prepare antibodies to these proteins as noted herein for use in kits to monitor the presence of pathogenic streptococci in a patient sample. The procedures for ELISA or radioimmunoassays are known to those skilled in the art.

A further aspect of the invention provides for a method of diagnosing a pathogenic streptococcal infection, comprising:
a) collecting a patient sample suspected of harboring a *streptococcus*;
b) contacting the sample with a fluoresceinated PlyC multimer; and
c) measuring the amount of fluoresceinated multimer bound to the sample, wherein the detection of binding indicates the presence of streptococci in the sample.

A yet further aspect of the invention provides for a method for detecting the presence of streptococci in a sample, comprising:
a) collecting a patient sample suspected of harboring a *streptococcus*;
b) incubating the sample with the PlyC multimer;
c) collecting the cell lysate;
d) incubating the cell lysate with luciferin-luciferase; and
e) measuring the amount of light produced, wherein an increase in the amount of light produced is indicative of the presence of streptococci in the sample.

A yet further aspect of the invention provides for a method for detecting the presence of streptococci in a sample, comprising:
a) collecting a patient sample suspected of harboring a *streptococcus*;
b) incubating the sample in the presence of luciferin-luciferase along with the PlyC multimer; and
c) measuring the amount of light produced, wherein an increase in the amount of light produced is indicative of the presence of streptococci in the sample.

A yet further aspect of the invention provides for generation of antibodies to the PlyC multimer or subunits or fragments thereof. The antibodies may be polyclonal, monoclonal, chimeric, humanized, or single chain antibodies. They may be prepared in animals such as mice, rats, guinea pigs, rabbits, goats, sheep, horses, and pigs. These antibodies may be used for identification and isolation of the components of the streptococcal cell wall to which the PlyC multimer binds. An additional use of these antibodies may be for mobilizing the PlyC multimer to a Biacore chip to perform studies on the affinity or kinetics of binding of the PlyC multimer to its binding site on the streptococcal cell wall.

A yet further aspect of the invention would be to use the PlyC multimer to lyse the *streptococcus* in the infection, which will release the DNA of the *streptococcus*. This released DNA can then be utilized for PCR analysis to identify the *streptococcus*. A more particular embodiment of the invention is a method for detection of pathogenic streptococci in a sample, comprising:
a) collecting a sample from a patient suspected of having a streptococcal infection;
b) adding the PlyC multimer into the sample until lysis of bacteria is observed;
c) isolating the DNA from the lysed bacteria;
d) utilizing the isolated DNA for preparation of a probe which can be utilized for analysis and identification of the presence of *streptococcus* in a patient sample.

EXAMPLES

The following examples are put forth so as to provide those of ordinary skill in the art with a complete disclosure and description of how to isolate and use the nucleic acid of $C_1$ bacteriophage or the PlyC multimer or the other proteins and nucleic acids described herein, and to provide a suitable means for development of pharmaceutical compositions for therapeutic or diagnostic use, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Determination of the Genomic Sequence of $C_1$ Bacteriophage

Preparation and Purification of Phage

The lytic bacteriophage, $C_1$, and its host bacteria, group C streptococcus 26RP66, are both part of The Rockefeller University collection. For preparation of the $C_1$ bacteriophage, 26RP66 was grown at 37° C. in chemically defined media (CDM) for streptococci (JRH Biosciences) (27.13 g/L) and supplemented with 2.5 g/L sodium bicarbonate and 0.5 g/L cysteine. During early log phase ($OD_{650}$~0.25) 1/10 to 1/2 (v/v) of pre-warmed $C_1$ phage was added and allowed to incubate until complete lysis occurred (approximately 40 minutes). The lysate was clarified by centrifugation (10,000× g, 10 min), passed through a 0.45-micron filter (Amicon) and final phage purification was achieved by ultracentrifugation (100,000×g, 2 hr) with the phage pellet resuspended in PBS and stored at 4° C.

Purification of Phage DNA

To purified phage particles, RNase and DNase (10 μg each) was added and allowed to incubate for 30 min at 37° C., after which, 50 μl of 0.5 M EDTA was supplemented to inhibit the endonucleases. Protease K (200 μg) and SDS (0.5% final concentration) were added and the mixture and incubated for 1 hr at 65° C. Final DNA purification was achieved through common phenol/chloroform extraction protocols as previously described (Sambrook, J. et al. (1989) Cold Spring Harbor Laboratory Press, New York).

Receptor Studies

For $C_1$ infection studies, phage were added to an exponential growth of group C streptococci or group A-variant streptococci and monitored for either a clearing of a liquid culture as described above or plaque formation in a soft agar overlay. Alternately, group C streptococci were pretreated with pronase (100 μg/ml) or trypsin and chymotrypsin (100 μg/ml, each) for 30 minutes prior to exposure to the $C_1$ phage. For adsorption studies, group C cell walls were isolated as described (Fischetti et al. (1968) J. Exp. Med. 127:489-505), and the group C carbohydrate was isolated by the nitrous acid extraction method as described (Swanson, J. et al. (1969) J. Exp. Med. 130:1063-1091) Briefly, 100 μl of $10^8$ pfu/ml $C_1$ phage was mixed with isolated group C cell walls (5 mg/ml), group C carbohydrate (5 mg/ml), or 20 mM GalNAc in a final volume of 0.5 ml. After 10 min incubation at 37° C., log phase group C streptococci were added to a final volume of 1.0 ml, incubated 5 min, centrifuged to pellet the streptococci, and plated according to the soft agar layer technique. Adsorption is quantified a corresponding decrease in residual PFU/ml.

Terminal Protein Studies

To purify the DNA-protein complex, the same procedure used to purify the phage DNA from above was followed except a phenol extraction step with gentle shaking was used instead of multiple phenol/chloroform extractions. The DNA-protein complex, found at the interface between the aqueous and phenol layer, was extracted and precipitated by ethanol. Half of the DNA-protein complex was digested with Protease K (10 μg) for 30 min at 37° C. and re-purified by ethanol precipitation. Aliquots (10 μg each) of the DNA-protein complex or Protease K digested DNA (PK-DNA) were treated with either 2 μl (130 U) Exonuclease III or 2 μl (11 U) Lambda exonuclease (both from GibcoBRL), at 37° C. according to the manufacturer's instructions. Reactions were stopped with the addition of 10 mM EDTA at the indicated times prior to electrophoresis. Alternatively, PK-DNA (10 μg) was pretreated with 0.5 M piperidine for 2 h at 37° C. and then subjected to Lambda exonuclease treatment.

DNA Sequencing

For the library construction, genomic DNA was hydrodynamically sheared in an HPLC and separated on a 1% agarose gel. 3000-3500 bp fragments were excised, purified by the GeneClean procedure (Bio101, Inc.), blunt-ended using T4 DNA polymerase and ligated to unique BstX1-linker adapters. The linker-adapted inserts were separated from the unincorporated linkers by a second gel purification using GeneClean and ligated to BstX1-cut vector to form subclone libraries which were transformed into DH10β competent cells (Gibco/BRL, DH5α transformation protocol). DNA was purified from positive transformants using the Perfect-Prep384® system (Brinkmann Instruments) and then sequenced using ABI dye-terminator chemistry on automated MegaBace™ 1000 (Amersham) machines. Base calls and quality scores were determined using the program PHRED (Ewing, B. et al. (1998) Genome Res. 8:186-194). Reads were assembled using PHRAP with default program parameters and quality scores. Closure of gaps was accomplished by using primer-directed sequencing directly from purified phage DNA.

Bioinformatics

The LASERGENE suite of programs from DNASTAR was used for analysis, annotation, and assembly of the nucleotide and amino acid sequences. Putative open reading frames (ORFs) were identified by either the ORF Finder, available through the National Center for Biotechnology Information (http://www.ncbi/nlm.nih.gov), or the heuristic approach of gene prediction from GeneMark™ (Besemer, J. et al. (1999) Nucleic Acid Res. 27:3911-3920). The BLAST algorithms, (Altschul, S. F. et al. (1997) Nucleic Acid Res. 25:3389-3402) also available through NCBI, were used for similarity searches of putative ORFs. Sequence alignments were performed with CLUSTAL W and visualized with BOXSHADE.

Electron Microscopy

Purified phage were applied to a carbon film and fixed to a copper grid before being negatively stained with 1% uranyl acetate. Electron micrographs of the phage were taken using a JEOL 100 CXII transmission electron microscope. For phage infection images, $C_1$ bacteriophage were incubated with early log phase group C streptococci 26RP66 for 20 minutes, pelleted by centrifugation, and suspended in 2.5% glutaraldehyde in 0.1 M cacodylate buffer (pH 7.4). The samples were then postfixed in 1% osmium tetroxide, block stained with uranyl acetate and processed according to standard procedures. All microscopy was performed by The Rockefeller University Bio-Imaging Resource Center or in collaboration with Dr. John Swanson. The electron microscopy studies demonstrated the binding of $C_1$ bacteriophage to the cell wall of a group C *streptococcus* at 15 minutes post infection. The electron opaque capsid indicated that the phage DNA had not yet been injected. The honeycomb structure showed the progeny virions.

Nucleotide Sequence Accession Number

The DNA sequences of the genome reported herein appear in GenBank under accession number AY212251.

Results $C_1$ Bacteriophage Characterization

In agreement with a previously published report (Moynet, D. J. et al. (1985) Virology 142:263-269), the $C_1$ phage has a small polyhedral head (~50×50 nm) and a very short tail and tail fibers. A small collar or base plate was noted with three protruding appendages. The wider and longer central appendage is presumed to be the tail, but it is not clear if the side appendages are minor tail fibers similar to those seen in phage T7 or P22, or collar spikes as observed in the φ29 phage (Ackerman, H. et al. (1999), Adv. Vir. Res. 51: 135-201). Upon infection, complete lysis of susceptible group C streptococci was achieved by 40 minutes; however, mature phage particles could be observed emerging from infected streptococci by electron microscopy as soon as 10 minutes post infection (data not shown). We were able to manually count>100 progeny particles in one thin section micrograph of an infected *streptococcus*, which is consistent with a relatively high burst size noted previously (Fischetti, V. A. et al. (1968) J. Exp. Med. 127:475-488)

Elucidation of the $C_1$ Phage Receptor

Consistent with previous reports (Krause, R. M. (1957) J. Exp. Med. 106:365-384), it was determined that only group C streptococci were susceptible to infection by the $C_1$ bacteriophage. When these same streptococci were pretreated with pronase or trypsin and chymotrypsin, no inhibition of infection was noted indicating that the binding receptor is not of proteinaceous origin (Table I). The surface carbohydrate of group C streptococci is composed of a polyrhamnose backbone with side chains of two N-acetyl-galactosamine (GalNAc) residues whereas the group A-variant carbohydrate contains only the polyrhamnose backbone (Coligan, J. E. et al. (1978) Immunochemistry 15:755-760). Therefore, our data demonstrating that the $C_1$ phage is unable to infect group A-variant streptococci implicates GalNAc as a potential phage receptor.

For adsorption studies, we found that isolated group C streptococcal cell walls were very efficient in adsorbing the $C_1$ phage, reducing $10^7$ pfu/ml to less than $10^2$ pfu/ml (Table II). Additionally, we found that the chemically extracted group C carbohydrate also retained the ability to adsorb $C_1$ phage. This is in contrast to Fischetti and Zabriskie's earlier findings (Fischetti, V. A. (1968) J. Exp. Med. 127:489-505); however a method of nitrous acid extraction of the carbohydrate layer was used, which is more efficient than the hot formamide method utilized by the former authors. Finally, when $C_1$ phage were treated in the presence of 20 mM GalNAc monosaccharide, no adsorption was observed, strongly suggesting that the disaccharide rather than the monosaccharide of GalNAc, serves as the receptor for the $C_1$ bacteriophage, although we cannot rule out possible contributions of other epitopes to the infection process at this time.

Organization of the $C_1$ Genome and Identification of ORFs

A double stranded, linear sequence of 16,687 bp was established with a mean redundancy of six, with each region being sequenced a minimum of at least once on each strand. A G+C content of 34.6% is similar to the host and other "low GC" streptococci. 200 bp inverted terminal repeats were present which are characteristic of the "φ29-like" *Podoviridae* (Ackermann, H. W. (1999) Adv. Virus Res. 51:135:201).

The criteria for the characterization of a potential open reading frame (ORF) were the existence of a start codon (ATG, GTG, or TTG) and a minimum coding size of 50 amino acids. Using these criteria, 20 predicted ORFs were identified by both ORF Finder and GeneMark™, labeled 1-20 from the left end of transcription (Table III). The first eleven ORFs are on the positive strand and the remaining 9 ORFs are all on the negative strand. Unexpectedly, the majority of ORFs were not only dissimilar to known phage proteins, but had no homology to any proteins contained in GenBank. Therefore, we only assigned putative function to ORFs with significant homology or experimental proof. Included in this group are the following:

(i) Orf6. Although orf6 did not have a high E value (1.2), it did have ~20% identity to neck appendage proteins (late protein GP12) from *Bacillus* phages φ29 and PZA.

(ii) Orf7. Orf7 had high homology to DNA polymerases from *Bacillus* phages φ29 and GA-1. Significantly, these phage polymerases utilize a protein-primed mechanism of replication (see below for evidence of a terminal protein).

(iii) Orf8. Orf8 is a putative holin with similarity to a *Listeria* prophage holin and the *Bacillus* φ-105 phage holin. Additionally, with 108 amino acids and 3 predicted transmembrane domains, this sequence fits the classic type I holin, as do holins from the φ-29, φ-105, and Cp-1 *Podoviridae* (Wang, I. N. et al. (2000) Annu. Rev. Micrbiol. 54:799-825.

(iv) Orfs 9,10, and 11. The 72 amino acid orf9 has no homology to any known protein. Yet, sequencing of the purified $C_1$ lysin yielded an N-terminal sequence that corresponded to Orf9 (data not shown). However, the native $C_1$ lysin has a predicted MW of ~100 kDa, significantly larger than ORF9 (Nelson, D. et al. (2001) Proc. Natl. Acad. Sci. U.S.A. 98:4107-4112). This may be explained by investigating ORFs 10 and 11. ORF 10 has noteworthy homology to the HNH family of homing endonucleases found in many phages (specifically, LambdaSa2 from *Streptococcus agalactiae* and bIL170 from *Lactococcus* spp.). These endonucleases are often part of bacteriophage intron systems that give rise to modular enzymes. Orf11 has the highest identity with a putative amidase (lysin) from the LambdaSa1 phage infecting group B streptococci. However, the LambdaSa1protein is over 1200 amino acids and the "amidase" region comprises less than 100 amino acids, none of which share identity with the orf11 gene product. The remaining 1100 amino acids of the LambdaSa1 protein resemble a phage tail protein. As such, the $C_1$ orf11 also has high homology to a putative tail protein from phage 315.5 infecting group A streptococci. Although no typical lysin or amidase regions are present on either orf9 or 11, it is inviting to speculate that if orf10 is an intron, gene products of orf9 and 11 could be spliced together to form an active lysin. The combined size of Orfs9 and 11 would approximate the size of the native $C_1$ lysin, and remarkably, introns have been found in the middle of modular lysin genes for multiple streptococcal phage (Foley, S. et al. (2000) J. Virol. 74:611-618). Work is in progress to elucidate the exact interactions between Orfs 9, 10, and 11 to yield a functional lysin.

(v) Orf12. Orf12 is the major tail protein based on homology to the GP9 protein from *Bacillus* phage in the *Podoviridae* family (B103, φ29, and GA-1).

(vi) Orf15. Orf15 is a head tail connector (collar) protein based on homology to the GP10 protein from *Bacillus* phage (GA-1 and φ29).

(vii) Orf16. Orf16 does not have homology to known proteins. Yet, we experimentally determined this 44-kDa protein to be the major structural protein (see below) and believe it is the head or capsid protein.

$C_1$ Phage Structural Proteins

In order to examine $C_1$ structural proteins, purified phage particles were subjected to SDS-PAGE. Although several bands could be distinguished, two notable bands comprised>90% of the visualized protein. N-terminal sequencing of the two most prominent bands revealed the 44 kDa and 36 kDa bands correspond to orfs16 and orf15, respectively. Whereas orf15 is consistent with head/tail connector base plate proteins from several phage systems, orf16 does not share homology with any known proteins. N-terminal sequencing of the smaller, 36-kDa band gave the sequence MQITSGIK (amino acids 1-8 of SEQ ID NO: 15), which corresponds to Orf15 (SEQ ID NO: 15), a putative 35.9 kDa protein with significant homology to the upper collar proteins (GP-10) from *Bacillus* phages GA-1, B103, and φ29 (Table III). The larger and more abundant 44-kDa protein had an N-terminal sequence of ADETTNVA (amino acids 1-8 of SEQ ID NO: 16). This sequence corresponds to Orf16 (SEQ ID NO: 16), a putative 43.7-kDa protein that does not share similarity with any known protein in GenBank. Because this band accounts for ~75% of the total phage structural proteins by scanning densitometry, we believe that it represents the major capsid or head protein despite any homology with similar proteins. This is partially supported by a lack of an identified capsid protein in Table III, but presence of other expected structural proteins such as neck appendage (Orf6), major tail (Orf12), and collar protein (Orf15).

Evidence of a Covalently Linked 5' Terminal Protein

Bacteriophages that utilize a protein-primed mechanism of replication have a terminal protein (TP) covalently linked to the 5' termini of the DNA. One characteristic of this DNA-protein complex is a noted lack of migration in a standard agarose gel (Garcia, E., et. al (1983) Virology 128:92-104). We observed this trait for the $C_1$ bacteriophage DNA (data not shown). The migrating band presumably represents DNA that had the TP sheared off during the phenol step in purification. Protease K (PK) treatment of the complex results in complete conversion of all non-migrating complex to migrating DNA with a size of ~17 kb. Exonuclease III, which is specific for unblocked 3' termini, degrades both the DNA-protein complex and PK-DNA. Although we demonstrate that the 3' termini is free in both the DNA-protein complex and the PK-DNA, Exonuclease III has slower activity on the complex, most likely due to steric hindrance of the TP near the 3' termini.

In contrast to Exonuclease III, both the DNA-protein complex and the PK-DNA are insensitive to the effects of the 5' specific Lambda exonuclease. However, pretreatment of the PK-DNA with 0.5 M piperidine, which has been shown to specifically hydrolyze the bond between the DNA and TP in the φ29 bacteriophage (Penalva, M. S. et. al (1982) Proc. Natl. Acad. Sci. U.S.A. 79:5522-5526) renders the 5' termini unprotected.

Analysis of the DNA Polymerase

The data noted above confirms that the $C_1$ bacteriophage DNA contains protein covalently linked to the 5' termini. Further evidence supporting the existence of a terminal protein can be found by examination of the putative $C_1$ DNA polymerase. Bioinformatic analysis suggests the $C_1$ polymerase belongs to family B of DNA polymerases (also referred to as eukaryotic or α-like), which comprises eukaryotic, viral, and protein-primed polymerases. This family has consensus sequences known to be important for proofreading and strand displacement functions (ExoI, ExoII, ExoIII, cross-talk) as well as several consensus motifs (A,B,C) involved in initiation and polymerization. Significantly, polymerases that utilize a protein-primed mechanism of replication have two insertion motifs, called terminal protein regions (TPR), which lie between motif A and B (TPR-1) or motif B and C (TPR-2) (Blasco, M. A. et al. (Nucleic Acid Res. (18:4763-4770). The $C_1$ polymerase contains all necessary conserved elements, including both TPR regions.

Example 2

Cloning of PlyC

Bacterial strains, phage, and growth conditions. *Streptococcus pyogenes* D471 (group A strep), *Streptococcus equisimilis* 26RP66 (group C strep), and the $C_1$ bacteriophage are part of the Rockefeller University collection and were grown and maintained as previously described (Nelson, D., et al. (2001) Proc. Natl. Acad. Sci. U.S.A. 98:4107-4112; Nelson, D., et al. (2003) J. Bacteriol. 185:3325-3332). *E. coli* XL-1 Blue (Stratagene) and *E. coli* B834 (Novagen) were grown in Luria-Bertani (LB) broth at 37° C. in a shaking incubator (250 r.p.m.) unless otherwise stated. When needed, ampicillin (100 μg ml$^{-1}$) or chloremphenical (34 μg ml$^{-1}$) was added to the growth medium.

DNA manipulation. Phage DNA was isolated as previously described (Nelson, D., et al. (2003) J. Bacteriol. 185:3325-3332) and plasmid DNA was isolated using the Qiaprep kit (Qiagen). DNA polymerase, restriction, and modification enzymes were all purchased from New England Biolabs and used according to the manufactures instructions. Oligonucleotides were obtained from Sigma Genosys and all PCR was performed with the Eppendorf Mastercycler.

Cloning plyC. 5 μg aliquots of $C_1$ phage DNA were digested with Tsp509I and fragments ranging in size from 0.5-3.0 kb were cloned into the EcoRI site of the arabinose-inducible expression vector pBAD24 (Guzman, L. M., et al. (1995) J. Bacteriol. 177:4121-4130). The resulting expression library was then transformed into *E. coli* XL1-Blue and screened for lytic activity on glass LB plates containing 100 μg ml$^{-1}$ ampicillin and 0.25% arabinose. The induced library was permeabilized with chloroform vapors and overlaid with exponential phase *Streptococcus pyogenes* D471 in 0.75% LB agar. After 4 h incubation, distinct clearing, or lytic, zones were identified over library members. Corresponding plasmid DNA was prepared and sequenced at the Rockefeller University DNA Sequencing Resource Center. DNA sequence analysis and manipulations required the BLASTP (NCBI), ORF finder (NCBI), and SeqMan 5.0 (Dnastar Inc.) programs.

Biochemical techniques. PlyC was induced from XL1-Blue/pBAD24::plyC with 0.5% arabinose in overnight LB cultures. Cells were washed in 20 mM phosphate buffer at pH 7.0, and lysed with chloroform to yield crude PlyC. Purification of the recombinant enzyme and the plate assay to follow activity were identical to previously described methods used for the phage-produced enzyme (Nelson, D., et al. (2001) Proc. Natl. Acad. Sci. U.S.A. 98:4107-4112). The purified enzyme was routinely stored in phosphate buffered saline (PBS) at 4° C. and was stable for several months. Purification of the individually expressed heavy and light chains utilized the same column chromatography methods as the native enzyme, but purification was followed by SDS-PAGE rather than activity assays. Native and SDS-PAGE analysis were performed according to the method of Schagger (Schagger, H., et al. (1987) Anal. Biochem. 166:368-379) and blotting to polyvinylidene difluoride membranes was according to Matsudaira (Matsudaira, P. (1987) J. Biol. Chem. 262:10035-10038). N-terminal sequencing was performed at Rockefeller University Proteomics Resource Center. For the denaturation and refolding studies, urea was added to 100 µg each of PlyC-A and PlyC-B until the final concentration was 8M. Urea was slowly removed over 72 hours by successive dialysis against 6M, 4M, 2M urea, and finally PBS. Standard activity assays, normalized to control PlyC, were performed on equal masses of PlyC-B, PlyC-A, a mixture of heavy and light chains before denaturation, and after refolding. In the cross-linking experiments, we employed bis(sulfosuccinimidyl)suberate ($BS^3$), a water soluble, non-cleavable, homobifunctional cross-linker with a chain length of 11.4 Å and reactivity toward amino groups (purchased from Pierce). A fresh stock of $BS^3$ (1 mg ml$^{-1}$) was made in 20 mM phosphate buffer, pH 7.4, and 55 µl of this solution (5 µM final concentration) was added to 100 µg of purified PlyC in a final volume of 1 ml and allowed to react for 45 minutes at room temperature. The reaction was quenched by the addition of 25 mM Tris for 15 min at room temperature and then SDS-PAGE reduced sample buffer. Analytical gel filtration for size estimation of the native and the cross-linked enzymes employed a Superose 12 column (Amersham Biosciences) calibrated with gel filtration standards (Bio-Rad).

Expression of individual ORFs, chimeras, and co-transformants. Plasmid DNA was purified from XL1-Blue/pBAD24::plyC and individual ORFs were amplified by PCR as follows: for the light chain (plyCB), the primers Light-F (5'-GTAC-CCGGGGAAGTAATTTCCATTCTTGAA-3') (SEQ ID NO: 26) and Light-R (5'-CCCAAGCTTTTACTTTTTCAT-AGCCTTTCT-3') (SEQ ID NO: 27); for the intergenic region (lil), the primers LIL-F (5'-GTACCGGGGAGGAGGAAT-TCATGATTGAGGAGTGGGTC-3') (SEQ ID NO: 28) and LIL-R (5'-GGGAAGCTTTTACTCATTAAATAAAT-TCTCCCTTTC-3') (SEQ ID NO: 29); and for the heavy chain (plyCA), the primers Heavy-F (5'-GTACCCGG-GAAAGGGAGAATTTATTTAATG-3') (SEQ ID NO: 30) and Heavy-R (5'-CCCAAGCTTTGGGTTCAATTCAAGG-GAATA-3') (SEQ ID NO: 31). All forward primers contained a SmaI site and all reverse primers contained a HindIII site. PCR products were digested by SmaI and HindIII and ligated into a SmaI/HindIII digested pBAD24 (Amp$^r$) vector or the pBAD33 (Crm$^r$) vector. For the PlyC heavy chain and light chain chimera, plyCB was PCR amplified by Light-F and Light-R primers, blunt ended, and ligated to pBAD24::plyCA which had previously been linearized by digestion with SmaI. A 1.6 kb PCR product using the primers Light-F and Heavy-R confirmed the proper insert size for this chimera. Finally, XL1-Blue cells were co-transformed with pBAD24::plyCA and pBAD33::plyCB, and cells displaying a Cm$^r$/Amp$^r$ phenotype were selected for further study. Positive PCR products were obtained using either primer sets Light-F/Light-R or Heavy-F/Heavy-R, but no product was observed using Light-F/Heavy-R, thus verifying that plyCB and plyCA were on separate plasmids.

$^{35}$S-methionine labeling of PlyC. E. coli B834 cells were transformed with pBAD24::plyC and methionine auxotrophy was confirmed by observing growth in M9 minimal media supplemented with 50 µg ml$^{-1}$ methionine, while no growth was noted in M9 media alone. A fresh 20 ml overnight culture of B834/pBAD24::plyC was washed twice with M9 media, and used to inoculate a 2 L flask of M9 minimal media supplemented with 2 mCi $^{35}$S-methionine (New England Nuclear). Expression of $^{35}$S-Methionine-PlyC was induced with 0.5% arabinose and the enzyme was purified as described above. The heavy and light chains were resolved by SDS-PAGE using 15 µg of labeled PlyC loaded each lane (n=20). Individual bands were cut out of the gel, suspended in 1 ml of SigmaFluor scintillation fluid (Sigma), and counts per minute (cpm) of β-activity was assessed on a Beckman LS5000TD counter.

Results

PlyC is composed of 2 sub-units. In 2001, we reported that the streptococcal $C_1$ bacteriophage lysin, now termed PlyC, was ~50 kDa by SDS-PAGE (Nelson, D., et al. (2001) Proc. Natl. Acad. Sci. U.S.A. 98:4107-4112). Nonetheless, we did note that gel filtration of the enzyme suggested a mass of ~100 kDa, which was consistent with previous reports (Fischetti, V. A., et al. (1971) J. Exp. Med. 133:1105-1117). At the time, it was speculated that the native enzyme exists as a homodimer or possesses additional subunits that could not be visualized. Here we have purified larger quantities of phage produced PlyC, as well as a recombinant PlyC, and shown that the enzyme behaves as a homogeneous preparation on native gel electrophoresis (FIG. 1A). Moreover, this band is responsible for the lytic activity as observed on an overlay of streptococci-embedded agarose (FIG. 1B). However, an SDS-PAGE of the same material revealed the presence of two bands, a 50 kDa heavy chain and an 8 kDa light chain (FIG. 1C), neither of which retain any lytic activity (data not shown). Furthermore, N-terminal sequencing of the heavy and light chains resulted in two unique sequences, SKKYTQQQYE (amino acids 9-18 of SEQ ID: 11) and SKINVNVENV (amino acids 2-11 of SEQ ID: 9), respectively, and sequencing of the native enzyme resulted in a double sequence, which corresponds exactly to both chains. Thus, we conclude that PlyC is composed of at least one heavy chain, which we now call PlyC-A, and at least one light chain, which we now call PlyC-B.

In the 2001 manuscript (Nelson, D., et al. (2001) Proc. Natl. Acad. Sci. U.S.A. 98:4107-4112), we never observed the light chain in an SDS-PAGE, however, this can be explained by several factors. In the original publication, a 10% polyacrylamide gel was used for electrophoresis, which allowed the 8 kDa light chain to migrate in the dye front and was subsequently not detected. Additionally, we were only able to purify ng quantities of enzyme necessitating the need for silver staining, which is now known not to effectively label the 8 kDa light chain. In this report, we utilized a 4-20% gradient gel, which allows for visualization of proteins<10 kDa. Finally, we purified sufficient quantities of enzyme to stain the gel in FIG. 1 by Coomassie stain, which does resolve the 8 kDa band.

Figure 2:
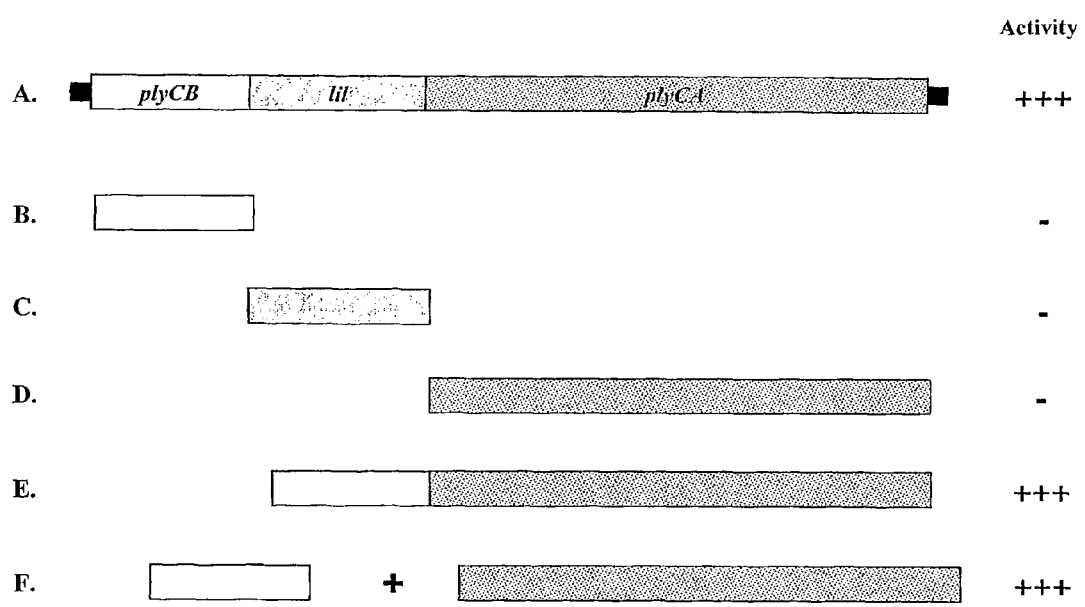
FIG. 2. Gene structure and analysis of the PlyC gene(s). (A) A clone displaying PlyC activity was found to contain 2.2 kb of sequence comprising 3 open reading frames (ORFs) and ~100 bp of untraslated region on both the 5' and 3' ends. This operon is called plyC (SEQ ID NO: 25). The first ORF contains the sequence for the PlyC light chain, PlyC-B (SEQ ID NO: 9), and its gene is called plyCB (SEQ ID NO: 22). The second ORF, positioned between the genes for the two chains of PlyC, contains a putative HNH endonuclease (SEQ ID NO: 10), suggestive of an intron, and hence its gene is called lil (SEQ ID NO: 24), for lysin intergenic locus. The third ORF contains the sequence for the PlyC heavy chain, PlyC-A (SEQ ID NO: 11), and its gene is called plyCA (SEQ ID NO: 23). (B) Expression of plyCB by itself contained no activity. (C) Expression of lil by itself contained no activity. (D) Expression of plyCA by itself contained no activity. (E) Expression of a chimera containing plyCB and plyCA possessed wild-type activity, indicating that lil is not necessary for formation of the active enzyme. (F) A double transformant, containing plyCB in pBAD33 (Crm⁺) and plyCA in pBAD24 (Amp⁺) contained PlyC activity, indicating that PlyC is composed of two separate gene products, PlyC-A and PlyC-B.

Cloning and sequencing the PlyC gene(s). To further investigate PlyC, we attempted to identify the gene(s) responsible for its activity in an expression library of the $C_1$ bacteriophage genome. Screening a Tsp509I expression library revealed only a single clone containing a 2.2 kb insert (SEQ ID: 25) possessed lytic activity toward group A streptococci. This insert included three open reading frames (ORFs) in addition to ~100 bp of non-coding sequence on both the 5' and 3' ends (FIG. 2A). Significantly, these ORFs correspond to ORFs 9, 10, and 11 of the recently sequenced $C_1$ phage genome (Nelson, D., et al. (2003) J. Bacteriol. 185:3325-3332) (SEQ. ID: 9, 10, and 11, respectively). Furthermore, ORF8 (SEQ ID: 8) of the genomic sequence is a holin and the majority of bacteriophage lysis systems exhibit a gene arrangement of a holin immediately prior to the lysins gene.

The first gene of the 2.2 kb insert, hereafter referred to as plyCB (SEQ ID: 22), codes for a 72 amino acid polypeptide (SEQ ID: 9) that matches the N-terminal sequence of PlyC-B, the PlyC light chain. The 7.8 kDa predicted mass of the plyCB gene product matches the observed size of the PlyC-B by SDS-PAGE (FIG. 1C). A BLAST search revealed no close matches for this protein in the database.

The third gene of the 2.2 kb insert, hereafter referred to as plyCA (SEQ. ED: 23), codes for a 465 amino acid polypeptide (SEQ ID: 11) with a predicted size of 50.5 kDa. This matches both the size and the N-terminal sequence of PlyC-A, the PlyC heavy chain. A BLAST search indicated the gene product had limited homology to a putative amidase from the S. agalactiae prophage Lambda Sa1 (AAM99497), a putative tail protein of the S. pyogenes prophage 315.5 (AAM79918), and a putative minor structural protein of the S. thermophilus phage Sfi11 (AAC34413).

The second gene of the PlyC clone encodes a potential 105 amino acid protein (SEQ ID: 10), which has noteworthy homology to putative endonucleases from the S. agalactiae prophage Lambda Sa2 (ANN00738), Lactococcus phage bIL170 (AAC27227), and Vibriophage VpV262 (AAM28379). All of these endonucleases belong to the HNH family of endonucleases, which are embedded within a group I intron and confer mobility to the host intervening sequence by catalyzing double-stranded breaks in cognate alleles lacking the intron (Chevalier, B. S., et al. (2001) Nuc. Acid Res. 29:3757-3774). Significantly, group I introns are not only present in many bacteriophage systems, but they have been shown to interrupt lysin genes in over half of the known S. thermophilus bacteriophage (Foley, S., et al. (2000) J. Virol. 74:611-618). As such, HNH endonucleases are thought to be involved modular evolution of phage (Crutz-Le Coq, A.-M., et al. (2002) Microbiol. 148:985-1001). Due to the unique position of this gene between plyCB and plyCA, we choose to call this region of our clone lil (SEQ ID: 24), for lysin intergenic locus.

Transcriptional and translational analysis of the PlyC genes. To determine the minimal sequence necessary for lytic activity, individual genes or chimeras were cloned into a pBAD24 expression system and evaluated for activity on group A streptococci. Neither plyCB, lil, nor plyCA alone was sufficient for activity (FIG. 2B,C,D). However, a lil⁻ chimera, which contained full-length plyCB and plyCA, possessed wild-type PlyC activity (FIG. 2E). Therefore, neither the lil gene nor the gene product is needed for formation of active PlyC. Additional truncations of either the plyCB or plyCA genes in the lil⁻ clone ablated enzymatic activity (data not shown).

RT-PCR results indicate that intron splicing is not a mechanism used to fuse plyCB and plyCA (data not shown). Therefore, it is possible that each gene is independently translated and the gene products, PlyC-B and PlyC-A, self-associate post-translationally. In order to investigate this theory, we constructed two separate plasmids, pBAD33::plyCB (Crm$^r$) and pBAD24::plyCA (Amp$^r$), and double transformed both plasmids into one host. Light-F and Heavy-R primers were used for PCR and the absence of a product indicated that the full length PlyC clone was not present (data not shown). Upon induction with 0.5% arabinose, the double transformant contained PlyC activity (FIG. 2F). Therefore, activity of native PlyC is dependant on two separate genes products, PlyC-B and PlyC-A, rather than any pre or post-translational splicing events. Additionally, the plyC is an operon composed of plyCB and plyCA, which may also be referred to as the plyCBA operon.

Figure 3:
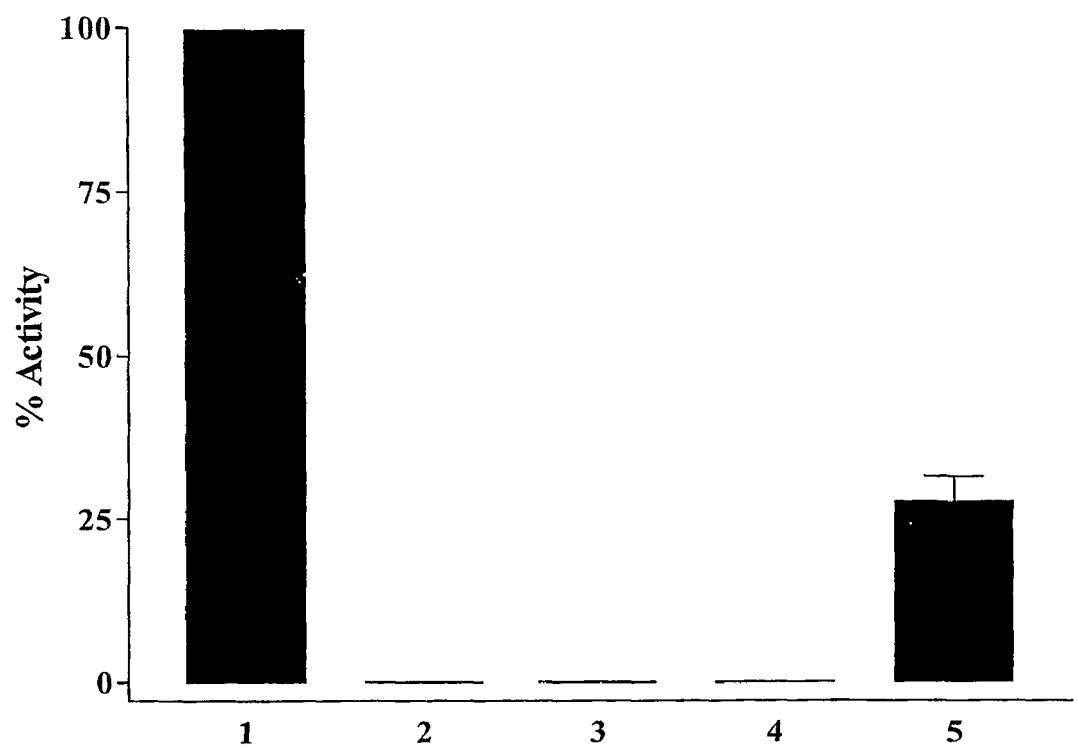
FIG. 3. Denaturation and refolding of PlyC subunits. Lane 1, activity of the native PlyC clone normalized to 100%. Lanes 2 and 3, individual activity of expressed PlyC-B and PlyC-A, respectively. Lane 4, activity of PlyC-B and PlyC-A mixed together, but expressed individually. Inactive samples from lane 4 were denatured in 8M urea and allowed to refold by dialyzing against decreasing concentrations of urea, and finally PBS, which reconstituted ~25% of the wild-type activity (lane 5).

In order to investigate interactions of PlyC-B and PlyC-A at the level of translation, we performed several folding experiments (FIG. 3). As expected, neither PlyC-B nor PlyC-A alone had any activity against group A streptococci. When both chains were mixed together and allowed to incubate at room temperature for 1 hr, again no activity was noted. However, when both chains were mixed together, denatured in 6 M urea, and allowed to slowly refold by dialysis against PBS overnight, we were able to reconstitute ~30% of wild-type activity. Consequently, PlyC-B and PlyC-A, each separate gene products, must be folded together at the level of translation to form the active enzyme, PlyC.

Figure 4:
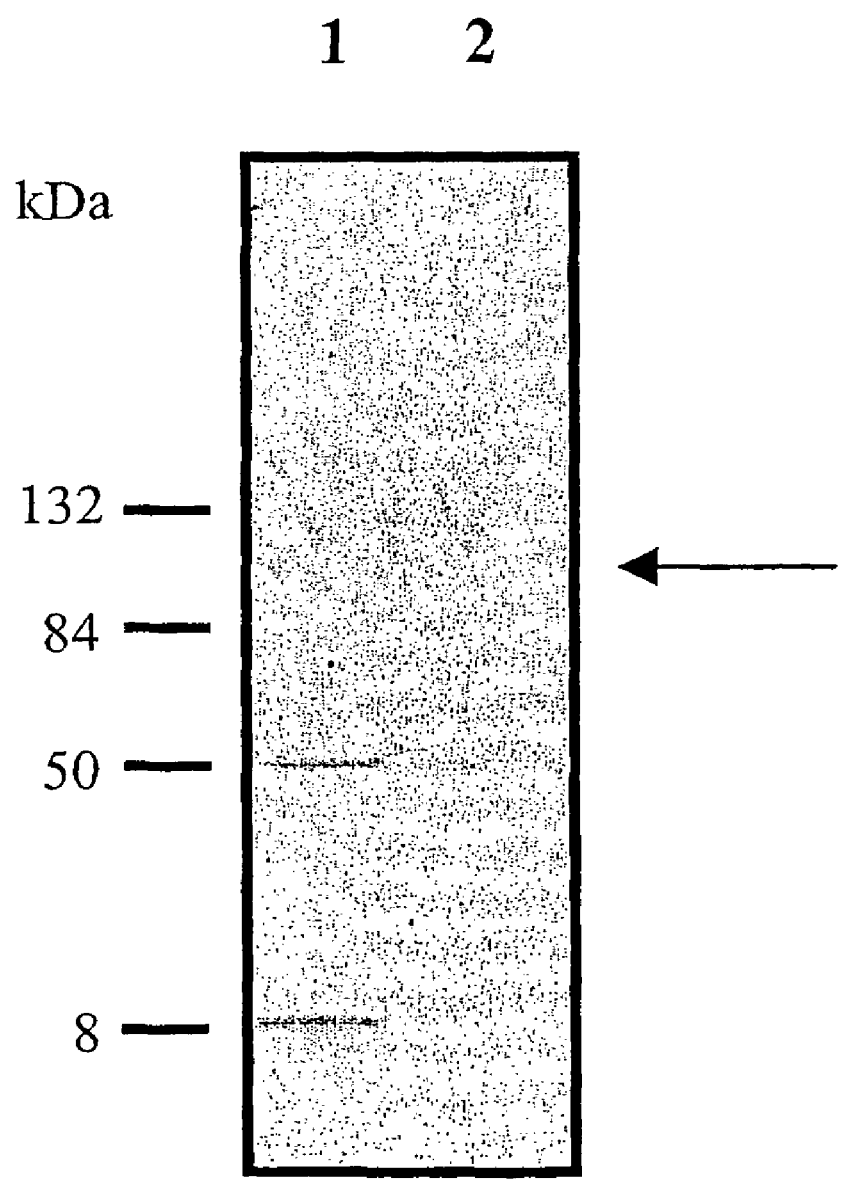
FIG. 4. Crosslinking of PlyC. SDS-PAGE on a 4-20% gradient gel. Lane 1, native PlyC showing the 50 and 8 kDa subunits. Lane 2, PlyC treated with the non-cleavable crosslinker, BS$^3$ (arrow shows the diffuse band ~100 kDa).

A model for the proposed structure of PlyC. In 1971, it was suggested that the mass of the streptococcal lysin (now PlyC) was 101 kDa based on the sedimentation coefficient and gel filtration of a semi-pure preparation (Fischetti, V. A., et al. (1971) J. Exp. Med. 133:1105-1117), which was confirmed more recently with a pure preparation (Nelson, D., et al. (2001) Proc. Natl. Acad. Sci. U.S.A. 98:4107-4112). Despite the current genetic and biochemical data of a 50 kDa PlyC-A heavy chain and an 8 kDa PlyC-B light chain presented above, a simple heterodimer model of the two chains does not rationalize the apparent 100 kDa mass of the native enzyme. To corroborate the mass of native PlyC, we utilized a non-cleavable crosslinker, bis(sulfosuccinimidyl)suberate ($BS^3$), which reacts with primary amines and the ε amine of lysine. An SDS-PAGE of the crosslinked PlyC substantiates that the native enzyme is ~100 kDa (FIG. 4). Furthermore, the elution profile on a Superose 12 gel filtration column of the crosslinked PlyC was super-imposable on that of native PlyC, indicating that the crosslinking process did not alter the mass of the enzyme (data not shown).

In order to achieve a mass of 100 kDa, multiple copies of one or both subunits must exist. Thus, PlyC is a multimer. Circumstantial evidence for a molar ratio of 5 light chains to one heavy chain was obtained from N-terminal sequencing of the native enzyme, which yielded a 55 pm signal for PlyC-B and a 12 pm signal for PlyC-A (data not shown). However, this observation could be mitigated if the PlyC-A had a partially blocked N-terminus. Therefore, to further investigate the ratios of PlyC-A and PlyC-B, we cloned plyC into B834 E. coli cells, which are auxotrophic for methionine. After expressing PlyC in M9 minimal media supplemented with $^{35}$S-methionine as the only methionine source, we purified the labeled enzyme and separated the heavy and light chains by SDS-PAGE. We were able to enumerate an average signal, measured in counts per minute, for each chain by placing gel-extracted bands (n=20) in scintillation fluid and measuring the β activity (Table IV). The average chain-specific cpm was subsequently divided by the number of known methionine residues for each subunit (10 for PlyC-A and 1 for PlyC-B), thus yielding an average cpm per methionine per chain. This data suggests a molar ratio of six light chains for each heavy chain in an active PlyC molecule. Significantly, this proposed model would yield an enzyme with a mass of 98 kDa (6×8 kDa+50 kDa), which is validated by the gel filtration and crosslinking experiments, both of which predicted a mass of ~100 kDa.

Example 3

PlyC Activity Against Various Streptococcal Strains

Methods. Measurement of lysin activity was based upon turbidimetric determination of cell lysis. Simple detection of activity during purification utilized 96 well plates (Costar) and an automated plate reader (Molecular Devices) measuring a decrease in $OD_{650}$ of group A streptococcus D471 cells. All bacterial strains were grown overnight in Todd Hewitt media, washed twice in phosphate buffered saline (PBS), and the $OD_{650}$ was adjusted to ~1.0 with PBS. Each cell suspension (225 µl) was added in triplicate to a 96 well microtiter plate just prior to addition of 250 U of purified PlyC (25 µl of a 10,000 U/ml stock). The $OD_{650}$ was monitored for each well over the course of the experiment and the plates were shaken before each reading to maintain cell suspension. Controls with PBS were used for each strain to observe spontaneous lysis of cells and/or sedimentation effects that were not resolved by the shaking. Although no spontaneous lysis was observed, several strains did have ~10% decrease in $OD_{650}$ after several hours due to sedimentation. In these cases, the $OD_{650}$ decrease seen in the controls were added back to the lysin experimental values to compensate for the natural settling. The activity of PlyC for each strain was reported as the initial velocity of lysis, in –OD/min, based on the time it took to decrease the starting OD by half (i.e. from an $OD_{650}$ of 1.0 to 0.5).

Results

Figure 5:
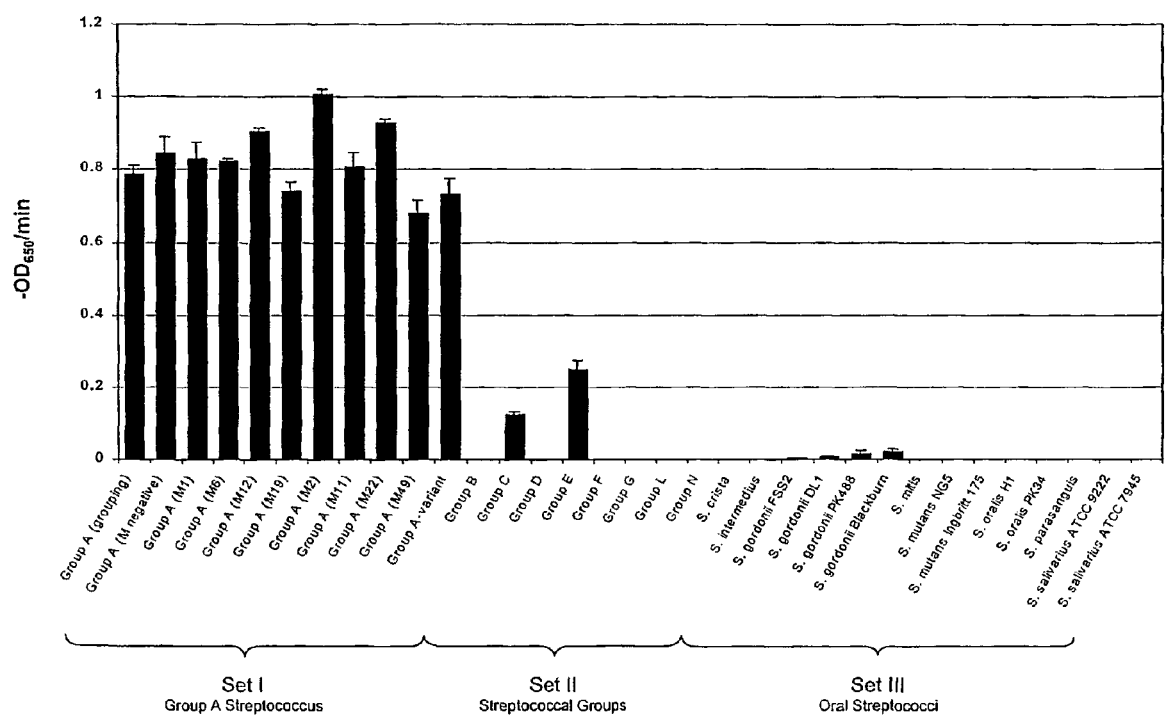
FIG. 5. PlyC activity on various streptococci. Representative streptococcal strains were exposed to 250 U of purified PlyC and the OD$_{650}$ was monitored. The activity of PlyC for each strain was reported as the initial velocity of lysis, in OD$_{650}$/min, based on the time it took to decrease the starting OD by half (i.e. from an OD$_{650}$ of 1.0 to 0.5). All assays were performed in triplicate and the data are expressed as means±standard deviations.

Purified $C_1$ phage lysin (PlyC) was tested for muralytic activity against >40 bacterial strains in a variety of species which were divided into sets (FIG. 5). Set I contained 10 different group A streptococcal strains including the serological grouping strain, an M-negative strain, 8 distinct M types (representing class I and class II streptococci (Bessen, D., et al. (1989) J. Exp. Med. 169:269-283)), and an A-variant strain. PlyC was able to equally and completely lyse every strain in this set within 5 minutes and no viable colonies were detected after plating cells exposed to PlyC for this amount of time. Set II contained 8 different Lancefield groups of streptococci. We found that PlyC exhibited activity against groups C and E, though considerably less than that seen with group A strains; however, it was unable to lyse groups B, D, F, G, L, and N streptococci. In agreement with the spectrophotometric observations, no viable colonies were detected for groups C and E streptococci when plated up to 30 minutes after exposure to PlyC. Set III contained representative oral streptococci including *S. crista, S. intermedius, S. gordonii, S. mitis, S. mutans, S. oralis, S. parasanguis,* and *S. salivarius*. Very low but reproducible activity was only noted against all the *S. gordonii* strains tested. However, in these bacteria, cell viability remained near starting counts even after 30 minutes exposure to PlyC ($4.8\times10^7$ starting CFU and $4.6\times10^7$ CFU after 30 min for *S. gordonii* Blackburn). Set IV contained a mix of Gram-positive bacteria (*Bacillus pumulis, Staphylococcus aureus,* or *Staphylococcus epidermidis*) often found in the oral flora and Gram-negative (*Escherichia coli, Neisseria lactamicus, Porphyromonas gingivalis,* or *Pseudomonas aeruginosa*) bacteria. Lysin had no effect on these organisms (data not shown in FIG. 9) despite similarities in the peptidoglycan of all Gram-positive organisms.

Figure 6:
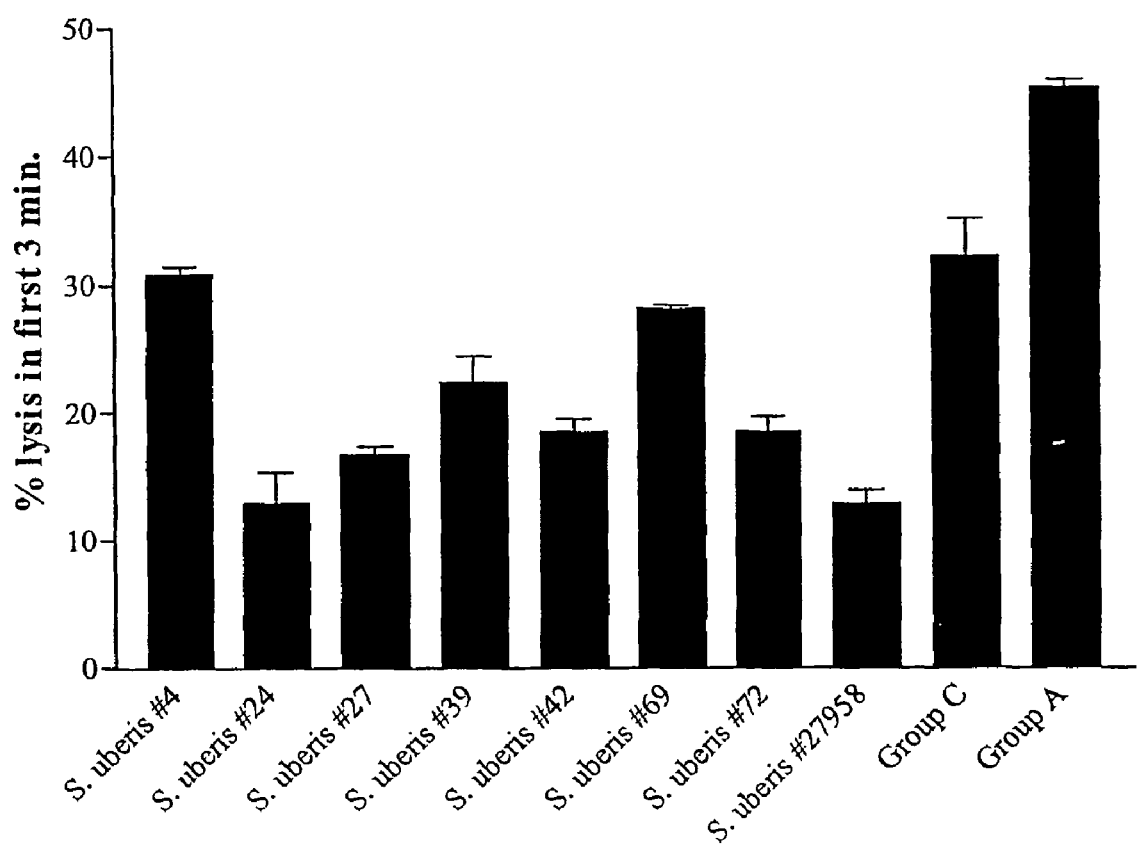
FIG. 6. PlyC activity on *Streptococcus uberis* strains. Representative streptococcal strains were exposed to 250 U of purified PlyC and the OD$_{650}$ was monitored. The activity of PlyC for each strain was reported as the % lysis that occurred in 3 minutes. *S. uberis* strains were clinical isolates or ATCC samples. Group A and C streptococci were control strains. All assays were performed in triplicate and the data are expressed as means±standard deviations FIG. 7. PlyC activity on *Streptococcus equi* strains. Two *S. equi* strains and the control Group A *streptococcus* strain (*S. pyogenes*) were exposed to 250 U of purified PlyC and the OD$_{650}$ was monitored. The activity of PlyC for each strain was reported as the initial velocity of lysis, in −OD$_{650}$/min, based on the time it took to decrease the starting OD by half (i.e. from an OD$_{650}$ of 1.0 to 0.5). All assays were performed in triplicate and the data are expressed as means±standard deviations.
Figure 7:
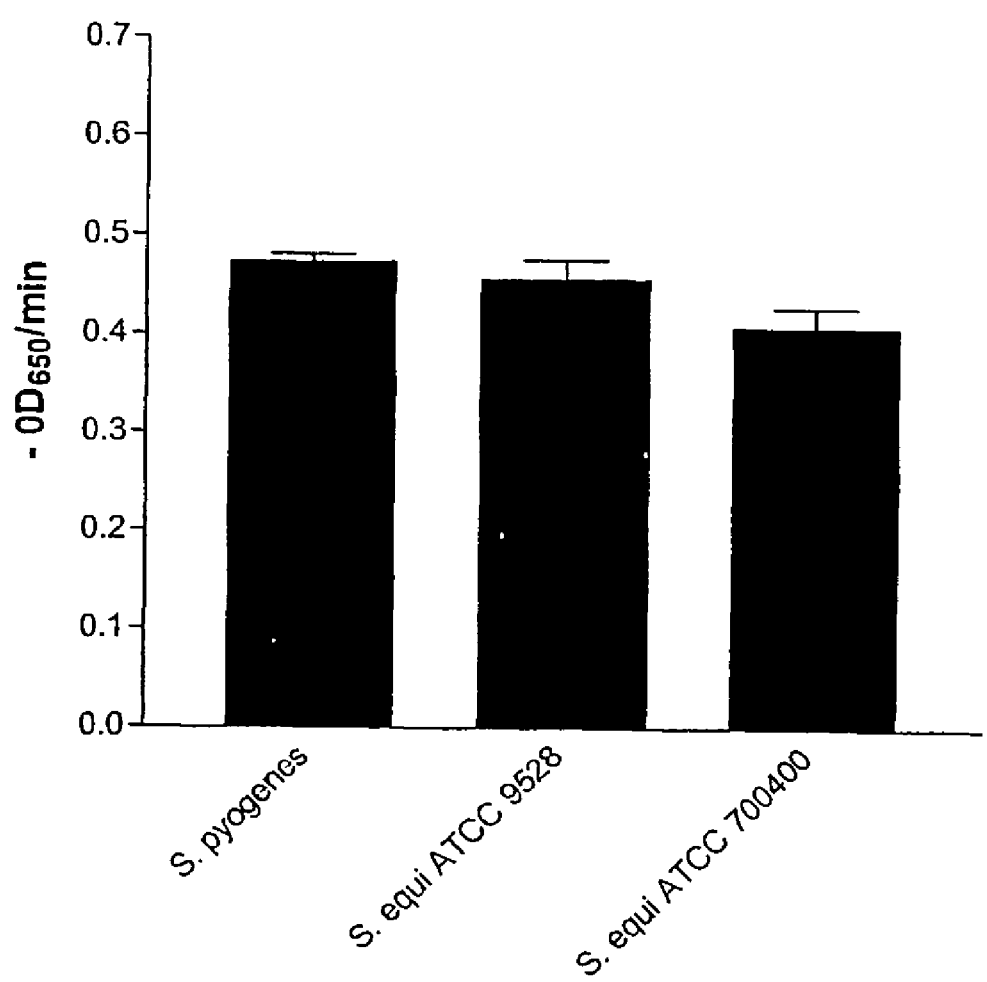

PlyC was subsequently tested against non-groupable streptococci that are pathogentic to animal. *S. uberis* causes bovine mastitis in dairy cows and significantly, PlyC was able to lyse every *S. uberis* strain tested including clinical isolates as well as reference strains in ATCC (FIG. 6). Likewise, PlyC possessed potent activity toward every *S. equi* strain tested (FIG. 7). *S. equi* is known to cause a condition called strangles disease in horses.

Example 4

PlyC has the Potential to be Used Diagnostically for Pathogentic Streptococcal Diseases Methods: We utilized the PROFILE-1 Model 3550i Microluminometer with the PROFILE-1 Reagent Kit, both of which are from New Horizon's Diagnostics Corporation. The microluminometer is a hand held device that uses an AC plug adaptor, but battery operated models are available for field use. For most assays, 50 ul of a bacterial sample was placed in a 0.45 micron Filtravette and positive pressure was used to remove any liquid. The sample was washed with a somatic cell releasing agent and then either treated with a bacterial releasing agent (strong detergent) or 100 U PlyC for 10 sec. 50 ul of a luciferin/luciferase mixture was added and the digital readout gave the relative light units (RLU) emitted over a 10 second integration.

Results

Figure 8:
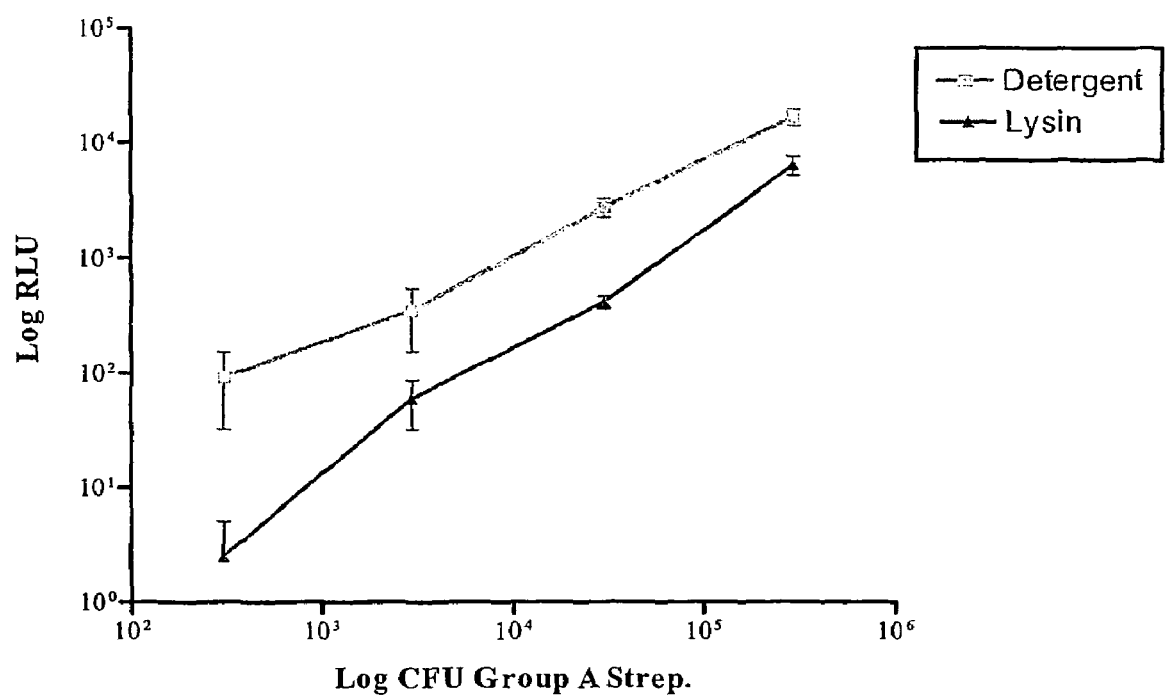
FIG. 8. Luminometer assay shows PlyC can correlate Relative Light Units to colony forming units of Group A streptococci as effectively as detergent. Group A streptococci were serially diluted, 100 ul was aliquoted in the NHD microluminometer, and 50 U of PlyC lysin was added for 10 min, after which the luciferin/luciferase was added. Alternately, a bacterial releasing agent (detergent) was used to identify the total microbial ATP. The PlyC treatment consistently yielded ~50% of the total ATP and was linear (r$^2$=0.912) down to ~300 organisms.

Traditional microbial ATP bioluminescent assays employ strong detergents to lyse bacterial cells. While this method works well to identify the presence of bacteria, it does not provide meaningful information about the type of bacteria present. Lysins are lytic enzymes encoded by bacteriophages that act on the host cell wall to release newly formed phage particles. These enzymes hydrolyze bonds common to most bacterial cell walls, yet they display unique specificity for the host organism or species, often restricted to just those organisms susceptible to the phage itself. Since phage typing has been accepted for years as a diagnostic tool, we investigated whether these lysins have the ability to provide both the specificity of phage typing and sufficient catalytic activity to lyse target cells within seconds for ATP detection in the presence of luciferin/luciferase. We show that PlyC, which has been shown to be specific for the cell walls of group A streptococci, can detect this organism in the luciferase based assay. Additionally, the relative light units (RLU) were found to be directly proportional to the amount of group A streptococci present, indicating a quantitative measurement (FIG. 8). Additionally, the PlyC produced curve was equivalent to that produced by the more traditional detergent method of extracting ATP.

Figure 9:
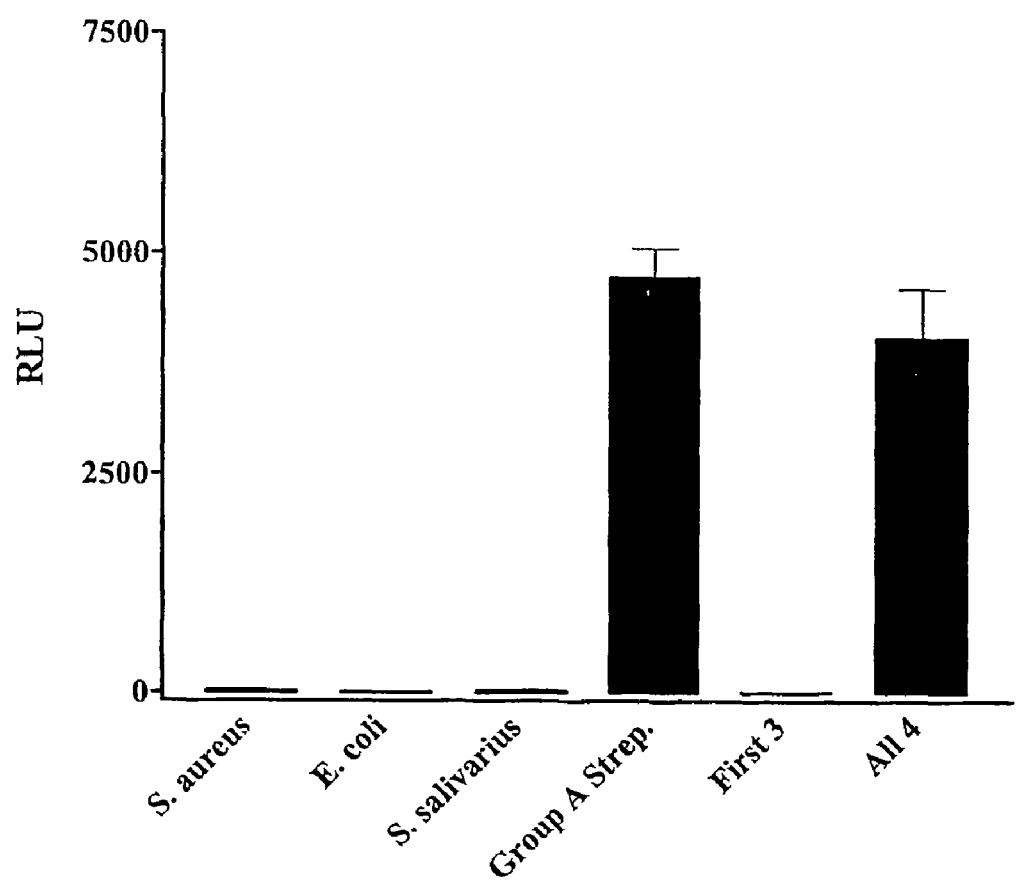
FIG. 9. Utility of PlyC as a diagnostic. *Staphylococcus aureus, E. coli,* and *Streptococcus salivarius* (~10$^6$ organisms) or group A strep (~10$^4$ organisms) were treated with 500 U of PlyC for 2 min and assayed in the microluminometer for a 10 sec integration. Mixing experiments contained the same proportion of CFU's.

Diagnostically, PlyC can be used in the luciferase based system to detect group A streptococci even when contaminating bacteria are present (FIG. 9). In a typical 10 sec assay with 100 U of PlyC, group A streptococci produced over 5,000 relative light units (RLU) (n=20) compared to less than 10 RLU produced for PlyC treated *E. coli, Staphylococcus aureus,* or the closely related *Streptococcus salivarius* (n=10 for each) (FIG. 9). Additionally, PlyC was able to detect group A streptococci in a mixture of the other organisms. These data suggest that use of PlyC may provide a rapid diagnostic tool to identify target bacteria in a variety of clinical and field applications;

TABLE I

| Ability of the $C_1$ bacteriophage to cause infection. | |
|---|---|
| | Plaque formation |
| Control (Group C strep) | ++++ |
| Pronase treated Group C strep | ++++ |
| Group A strep | – |
| Group A-variant strep | – |

TABLE II

| Adsorption of $C_1$ bacteriophage. | |
|---|---|
| | Residual Pfu/ml |
| Buffer control | $10^7$ |
| Group C cell walls | $10^2$ |
| Group C CHO | $10^3$ |
| 20 mM GalNAc | $10^7$ |

TABLE III

Features of C₁ ORFs from genomic DNA and their putative functions

| ORF | Strand | From | To | Length | aa | SEQ ID NO. | Putative function | Evalue |
|---|---|---|---|---|---|---|---|---|
| 1 | (+2) | 572 | 1092 | 522 | 173 | 1 | Unknown | >1 |
| 2 | (+3) | 1746 | 1934 | 189 | 62 | 2 | Unknown | >1 |
| 3 | (+2) | 1934 | 2470 | 537 | 178 | 3 | Unknown | >1 |
| 4 | (+3) | 2601 | 2918 | 318 | 105 | 4 | Unknown | >1 |
| 5 | (+2) | 2927 | 3550 | 624 | 207 | 5 | Unknown | >1 |
| 6 | (+1) | 3550 | 4776 | 1227 | 408 | 6 | Neck appendage | 1.2 |
| 7 | (+3) | 4806 | 7160 | 2355 | 784 | 7 | DNA Polymerase* | 3.00E−5 |
| 8 | (+1) | 7204 | 7530 | 327 | 108 | 8 | Holin | 9.00E−6 |
| 9 | (+2) | 7517 | 7735 | 219 | 72 | 9 | Lysin* | See text |
| 10 | (+1) | 7735 | 8052 | 318 | 105 | 10 | HNH endonuclease | 1.00E−4 |
| 11 | (+2) | 8024 | 9442 | 1419 | 472 | 11 | Lysin* | See text |
|  |  |  |  |  |  |  | Amidase (Group B strep.) | 8.00E−8 |
|  |  |  |  |  |  |  | Tail (*S. pyogenes* 315.5) | 3.00E−2 |
| 12 | (−3) | 11195 | 9471 | 1725 | 574 | 12 | Major tail | 3.00E−4 |
| 13 | (−1) | 12673 | 11381 | 1293 | 430 | 13 | Unknown | >1 |
| 14 | (−3) | 13370 | 12660 | 711 | 236 | 14 | Unknown | >1 |
| 15 | (−1) | 14320 | 13367 | 954 | 317 | 15 | Head-tail connector | 2.00E−06 |
| 16 | (−3) | 15545 | 14367 | 1179 | 392 | 16 | Major capsid* | See text |
| 17 | (−2) | 15738 | 15583 | 156 | 51 | 17 | Unknown | >1 |
| 18 | (−1) | 15913 | 15743 | 171 | 56 | 18 | Unknown | >1 |
| 19 | (−2) | 16296 | 16102 | 195 | 64 | 19 | Unknown | >1 |
| 20 | (−3) | 16547 | 16412 | 168 | 55 | 20 | Unknown | >1 |

*Experimentally determined or detailed further in the text

TABLE IV $^{35}$S-methionine radiolabeling PlyC to determine subunit ratios.

| Avg. PlyC-A cpm | 2583 |
|---|---|
| Avg. PlyC-B cpm | 1594 |
| Avg. cpm/met. for PlyC-A | 258.3 |
| Avg. cpm/met. for PlyC-B | 1594 |
| Avg. ratio PlyC-A:PlyC-B | 1:6.17 |
| Avg. ratio standard deviation | 1.66 |
| Proposed PlyC structure | PlyC-A(PlyC-B)$_6$ |

We claim:

1. An isolated polypeptide comprising an amino acid sequence of a $C_1$ bacteriophage PlyC lytic enzyme, wherein the polypeptide is a subunit PlyC lysin heavy chain (PlyC-A) and, wherein the polypeptide comprises the amino acid sequence of SEQ ID NO: 11.

2. A pharmaceutical composition for use in inhibiting or treating a bacterial infection, comprising an effective amount of the isolated polypeptide claim 1 and a pharmaceutically acceptable carrier.

* * * * *

SEQUENCE LISTING

<160> NUMBER OF SEQ ID NOS: 31

<210> SEQ ID NO 1
<211> LENGTH: 173
<212> TYPE: PRT
<213> ORGANISM: Bacteriophage C1 polypeptide

<400> SEQUENCE: 1

Met Lys Ile Arg Met Lys Thr Ile Tyr Thr Phe Ser Thr Thr Ile Ala
1               5                   10                  15

Thr Leu Ala Leu Gly Val Asn Leu Leu Met Asp Lys Gly Asp Asn Asn
                20                  25                  30

Asn Val Asn Thr Asp Asn Thr Phe Asn Asn Ser Asn Pro Ile Val Gln
            35                  40                  45

Val Asp Asn Asn Ser Ser Glu Ala Thr Thr Ile Thr Ser Asp Thr
    50                  55                  60

Asn Asp Asn Gln Val Ala Ala Asp Asp Thr Asn Asp Thr Glu Gln Leu
65                  70                  75                  80

Asp Tyr Phe Gln Pro Tyr Glu Tyr Leu Tyr Met Pro Ser Thr Asn Val
                85                  90                  95

Ser Ser Ile Arg Asp Gly Tyr Tyr Leu Val Ser Gly Gly Asn Thr Leu
                100                 105                 110

Ala Ala Val Gln Ile Thr Asn Gly Tyr Thr Thr Asp Glu Phe Arg Leu

```
                    115                 120                 125
Lys Asn Ile Ser Ala Glu Gln Trp Thr Val Ser Gln Gln Gln Met Glu
                130                 135                 140

Asp Phe Val Tyr Trp Leu Arg Glu Val Ser Pro Ser Gly Tyr Asn Gln
145                 150                 155                 160

Lys Ser Leu Glu Asn Asn Phe Lys Ile Phe Ile Lys Lys
                165                 170

<210> SEQ ID NO 2
<211> LENGTH: 62
<212> TYPE: PRT
<213> ORGANISM: Bacteriophage C1 polypeptide

<400> SEQUENCE: 2

Met Lys Thr Gln Glu Trp Tyr Leu Val Asn Phe Gly Leu Tyr Glu Thr
1               5                   10                  15

Lys Thr Gln Glu Met Glu Thr Asn Ser Arg Tyr Phe Glu Asp Lys Gln
                20                  25                  30

Ala Ala Leu Asp Phe Phe Tyr Thr Leu Ala Asn Glu Gly Tyr Tyr Asp
            35                  40                  45

Trp Ala His Val Tyr Ser Asn Leu Glu Met Glu Ile Ile Leu
        50                  55                  60

<210> SEQ ID NO 3
<211> LENGTH: 178
<212> TYPE: PRT
<213> ORGANISM: Bacteriophage C1 polypeptide

<400> SEQUENCE: 3

Met Lys Gln Thr Asn Ile Asp Ala Leu Phe Gly Lys Gly Asp His Gln
1               5                   10                  15

Leu Met Asn Lys Glu Ser Lys Tyr Leu Ser Thr Leu Phe Ile Asn Ile
                20                  25                  30

Glu Glu Leu Ser Val His Leu Ser Ser Val Thr Leu Phe Ile Asp Glu
            35                  40                  45

Tyr Glu Gln Leu Lys Glu Asn Ala Ile Lys Ser Lys Asn Gly Lys Cys
        50                  55                  60

Leu Lys Leu Gly Asn Thr Leu Tyr Phe Thr Asn Asn Asn Tyr Ala Thr
65                  70                  75                  80

Lys Leu Tyr Asn Ser Leu Leu Ala Leu Gly Phe Asn Gly Ala Asn Ser
                85                  90                  95

Phe Ser Ser Gly Glu Gln Thr Tyr Val Ile Ser Leu Thr Gly Gly Asn
            100                 105                 110

Ala Thr Leu Thr Thr Val Lys Thr His Tyr Gly Asp Val Lys Tyr His
        115                 120                 125

Tyr Lys His Glu Lys Leu Pro Val Lys Lys Ile Val Asn Asp Phe Trp
    130                 135                 140

Leu Ser Glu Gln Glu Tyr Val Tyr Thr Asn Ser Ile Lys Leu Ala Tyr
145                 150                 155                 160

Ala Leu Leu Asp Leu Tyr Lys Thr Met Gly Tyr Ser Thr Leu Asn Thr
                165                 170                 175

Ile Lys

<210> SEQ ID NO 4
<211> LENGTH: 105
<212> TYPE: PRT
<213> ORGANISM: Bacteriophage C1 polypeptide
```

```
<400> SEQUENCE: 4

Met Ala Ile Asn Phe Thr Asn Ile Gly Phe Ile Asn Phe Asn Lys Glu
1               5                   10                  15

Tyr Asn Lys Val Leu Lys Asn Gly Ala Ile Thr Ala Ser Met Ser Ala
            20                  25                  30

Ser Gln Lys Asp Val Lys Gly Glu Tyr Val Asp Glu Tyr His Asn Val
        35                  40                  45

Thr Ile Pro Lys Lys Val Ala Asp Gln Ile Lys Pro Leu Ile Asn Thr
    50                  55                  60

Glu Leu Cys Asp Ile Gln Gly Val Ile Ser Arg Asn Asp Lys Tyr Thr
65                  70                  75                  80

Asn Ile Thr Ile Leu Gly Ala Lys Lys His Val Lys Ala Glu Ala Val
                85                  90                  95

Asp Val Ala Asp Glu Asp Leu Pro Phe
            100                 105

<210> SEQ ID NO 5
<211> LENGTH: 207
<212> TYPE: PRT
<213> ORGANISM: Bacteriophage C1 polypeptide

<400> SEQUENCE: 5

Met Lys Gly Asp Glu Glu Arg Thr Ile Lys Ser Leu Phe Pro Leu Phe
1               5                   10                  15

Lys Tyr Met Ala Asn Lys Arg Gln Arg Lys Lys Gln Leu Lys Gln Gln
            20                  25                  30

Tyr Gly Val Gly His Lys Tyr Thr Pro Lys Leu Ser Gln Thr Gln Gln
        35                  40                  45

Lys Gln Ala Asp Phe Leu Lys Ser Ile Gly Gln Lys Phe Thr Asn Tyr
    50                  55                  60

Gln Thr Val Thr Ile Asp Lys Thr Tyr Ser Lys Asn Gln Glu Leu Leu
65                  70                  75                  80

Asp Thr Ala Asn Glu Ala Leu His Arg Leu Gly Ile Phe Phe Asp Gly
                85                  90                  95

Ser Glu Lys Ile Lys Leu Gln Gln Val Thr Asp Asp Leu Arg Tyr
            100                 105                 110

Ile Ile Asn Lys Leu Gln Pro Leu Leu Glu Ser Val Thr Met Arg Tyr
        115                 120                 125

Lys Lys Phe Leu Thr Asn Thr Tyr Arg Ser Asn Arg Asp Tyr Arg
    130                 135                 140

Leu Asp Trp Leu Leu Lys Ser Ala Ile Ser Lys Lys Leu Lys Asn Ala
145                 150                 155                 160

Gln Thr Val Arg Gly Leu Val Val Ala Ile Asn Lys Met Asp Arg Asp
                165                 170                 175

Phe Lys Glu Tyr Asp Lys Lys Leu Arg Lys Ser Ser Lys Gln Gly Asn
            180                 185                 190

Pro Phe Gly Phe Val Val Val Lys Tyr Ser Glu Met Gly Leu Met
        195                 200                 205

<210> SEQ ID NO 6
<211> LENGTH: 408
<212> TYPE: PRT
<213> ORGANISM: Bacteriophage C1 polypeptide

<400> SEQUENCE: 6
```

-continued

```
Met Ala Arg Lys Val Lys Lys Thr Ile Lys Thr Ile Phe Lys Asn Glu
  1               5                  10                 15

Glu Glu Glu Phe Lys Thr Leu Leu Asn Asp Tyr Arg Lys Lys Tyr Leu
             20                  25                  30

Pro Ser Lys Tyr Asn Gln Leu Glu Leu Leu Asp Trp Leu Cys Ser Asp
         35                  40                  45

Glu Ile Leu His Tyr Met Ser Ile Thr Ser Arg Gly Asp Gly Lys Ser
     50                  55                  60

Phe Asn Tyr Ile Gly Ala Leu Ala Trp Leu Ser Tyr His Leu Asn Phe
 65                  70                  75                  80

Gly Thr Met Leu Leu Val Arg His Trp Ser Leu Met Asp Lys Met Ala
                 85                  90                  95

Glu Met Val Phe Glu Ile Ile Arg Thr Val Gly Met Phe Asp Ile Glu
                100                 105                 110

Asn Val Gly Ile Gln Ala Lys Ala Asp Tyr Leu Thr Ile Thr Ile Glu
                115                 120                 125

Gly Arg Glu Val Phe Ile Ile Thr Asn Leu Asn Asn Ala Ser Asp Leu
        130                 135                 140

Lys Gln Ser Ser Ala Val Leu Arg Asn Tyr Pro Val Val Leu Tyr Asp
145                 150                 155                 160

Glu Phe Leu Thr Leu Gly Glu Asp Tyr Val Thr Asn Glu Leu Ala Lys
            165                 170                 175

Leu Gln Thr Ile Ile Lys Ser Ile Asp Arg Met Gly Lys Arg Pro Tyr
                180                 185                 190

Ile Lys Arg Pro Lys Ile Ile Tyr Leu Gly Asn Pro Val Asn Phe Asp
            195                 200                 205

Ser Pro Ile Leu Pro Ala Leu Asn Ile Phe Tyr Ala Leu Gln Asn Gln
        210                 215                 220

Glu Ile Asn Thr Ile Gln Gln His Gly Lys Thr Ile Leu Glu Leu Arg
225                 230                 235                 240

Arg Asn Asp Glu Val Asn Glu Lys Thr Thr Gly Tyr Phe Glu Asp
                245                 250                 255

Ser Val Asp Ser Asp Ile Thr Gly Glu Phe Asn Phe Ser Asn Tyr Arg
            260                 265                 270

Leu Ala Asp Gln Gln Thr Tyr Asn Lys Ala Leu Thr Asn Gly Thr Leu
        275                 280                 285

Tyr Lys Ile Arg Leu Glu Asp Lys Leu Ser Tyr Val Ile Leu Glu Ser
290                 295                 300

Asp Asn Glu Tyr Ile Leu Ser Ile Glu Glu Ser Lys Leu Asp Glu Asn
305                 310                 315                 320

Tyr Cys Ile His Leu Lys Asp Glu Thr Ala Thr Cys Glu Tyr Leu Lys
            325                 330                 335

Pro Ser Phe Tyr Lys Asp Ser Phe Ile Lys Arg Phe Gln Lys Gly His
        340                 345                 350

Phe Asn Phe Lys Asp Ser Phe Ser Arg Thr Phe Ile Glu Gly Asn Glu
            355                 360                 365

Asp Leu Gln Arg Leu Asn Phe Phe Lys Leu Asn Ala Val Ala Ser Thr
    370                 375                 380

Asp His Glu Asp Ala Tyr Ala Asn Ile Val Arg Glu Ser Trp Ile Ser
385                 390                 395                 400

Arg Leu Ala Lys Ile Tyr Glu Gln
                405
```

<210> SEQ ID NO 7
<211> LENGTH: 784
<212> TYPE: PRT
<213> ORGANISM: Bacteriophage C1 polypeptide

<400> SEQUENCE: 7

```
Met Lys Glu Phe Glu Gln Tyr Leu Lys Ser Phe Lys Gly Gln Lys Val
1               5                   10                  15

Thr Ser Val Asp Leu Tyr Cys Asp Ile Glu Thr Ala Thr Ile Asn Lys
            20                  25                  30

Asn Ser Gly Gln Lys His Ala Ser Thr Tyr His Ser Phe Thr Tyr Ser
        35                  40                  45

Leu Ala Val Ser Tyr Phe Lys Thr Gly Glu Glu Phe Pro Ser Val Val
    50                  55                  60

Val Phe Asn His Phe Lys Gln Leu Phe Asp Phe Ile Glu Lys Ser Lys
65                  70                  75                  80

Ile Arg Lys Ser Ile Glu Phe Arg Leu Ile Phe His Asn Gly Ala Lys
                85                  90                  95

Tyr Asp Asn His Phe Met Val Ser Glu Ile Gln Arg Asp Ile Asp Asn
            100                 105                 110

Val Arg Leu Phe Asn Gln Thr Ile Lys Gln Val Asn His Ile Thr Asp
        115                 120                 125

Leu Asp Leu Ser Lys Lys Gln Gly Lys Gln Met Arg Asn Asp Val Asn
    130                 135                 140

Met Val Leu Glu Arg Arg Val Arg Ser Ser Asn Asn Leu Asp Gly Asp
145                 150                 155                 160

Met Trp Ile Tyr Gly Arg His Tyr Glu Met Val Asp Ser Tyr Arg Lys
                165                 170                 175

Thr Asn Val Ser Ile Glu Leu Cys Gly Arg Met Leu Leu Asn Asn Gly
            180                 185                 190

Leu Ile Asp Glu Gln Tyr Leu Lys Thr Asp Phe Glu Tyr Asp Lys Tyr
        195                 200                 205

Asp Leu Asp Thr Asp Leu Thr Trp His Glu Val Arg Lys Tyr Arg Glu
    210                 215                 220

Phe Ile Phe Asn Asp Leu Asp Glu Lys Gln Met Lys Tyr Ile His Asn
225                 230                 235                 240

Asp Val Ile Ile Leu Ala Leu Thr Cys Lys His Tyr Ser Lys Leu Phe
                245                 250                 255

Tyr Gly Phe Asp Phe Glu Lys Gln Thr Phe Thr Gln Asn Ile Lys Glu
            260                 265                 270

Glu Tyr Ala Asn Tyr Asn Asp Met Ala Lys Phe Gln Leu Leu Lys Gln
        275                 280                 285

Ile Gly Asp Asn Met Thr Gly Lys His Leu Lys Leu Thr Asp Tyr Phe
    290                 295                 300

Ile Gln Gly Gln Asn Ala Tyr Asp Tyr Phe Lys Asn Tyr Tyr Asn Gly
305                 310                 315                 320

Gly Leu Asn Leu Tyr Asn Asp Lys Tyr Ile Gly Lys Lys Leu Val Arg
                325                 330                 335

Asp Gly Phe Ser Ile Asp Leu Asn Ser Ser Tyr Pro Thr Val Met Tyr
            340                 345                 350

Lys Glu Lys Leu Pro Thr Phe Leu Val Met Val Asp Ser Lys Pro Thr
        355                 360                 365

Asp Leu Lys Asn Ile Gly Ser Thr Asp Gly Asp Tyr Met Val Phe Phe
    370                 375                 380
```

```
Asn Met Leu Met Glu Asp Val Asn Asp Gln Ile Leu Ser Arg Ile Lys
385                 390                 395                 400

Ser Asn Val Ile Lys Ser Ala Ile Val Lys Tyr Trp Arg Val Lys Asp
            405                 410                 415

Gly Tyr Val Trp Leu Asn Asn Val Met Ile Ser Leu Ile Glu Glu Ile
        420                 425                 430

Thr His Gln Lys Phe Asn Asn Leu His Val Gln Ser Phe Ser Val Phe
    435                 440                 445

Glu Cys His His Phe Gly Ala Arg Asp Ile Ile Ala Lys Asn Tyr Phe
450                 455                 460

Ile Lys Thr Gln Gly Lys Met Ser Lys Ala Leu Asn Cys Thr Met Glu
465                 470                 475                 480

Thr Ile Asp Pro Leu Asn Ile Glu Leu Thr Asp Lys Asp Lys Pro Lys
                485                 490                 495

Glu Tyr Asp Phe Ser His Glu Met Val Glu Gly Ser Lys Val Leu Leu
            500                 505                 510

Asn Gly Ile Tyr Gly Ile Pro Ala Leu Arg Ala Tyr Phe Asp Cys Tyr
        515                 520                 525

Arg Arg Asp Glu Asn Gly Gln Leu Tyr Asn Val Ser Asn Gly Phe Glu
530                 535                 540

Asn Lys Glu Arg Asn Ile Val Phe Ser Ala Gly Val Thr Ala Phe Ala
545                 550                 555                 560

Val Arg Asn Leu Leu Leu Pro Leu Gly Lys Leu Thr Gln Asp Glu Ile
                565                 570                 575

Asp Asp Tyr Phe Trp Tyr Ala Asp Thr Asp Ser Leu Tyr Met Asp Lys
            580                 585                 590

Arg Ala Leu Pro Lys Leu Pro Lys Ser Met Phe His Lys Met Asn Leu
595                 600                 605

Gly Gly Trp Asp Ile Glu His Ala Asn Ile Ser Thr Phe Tyr Ala Phe
        610                 615                 620

Asn His Lys Lys Tyr Cys Leu Tyr Asp Asp Asp Asn Glu Ile Val
625                 630                 635                 640

Val Arg Cys Gly Gly Ile Ser Lys Ala Leu Ile Lys Lys Trp Ile Ala
                645                 650                 655

Glu Ser Arg Asn Asn Ile Asp Tyr Phe Ile Asn Asn Phe Phe Ile Asp
            660                 665                 670

Gly Val Thr Ile Pro Ala Thr Arg Ala Ile Arg Asn Glu Trp Asn Thr
        675                 680                 685

Ile Thr Ile Tyr Asp Gly Thr Ser Glu Leu Lys Lys Gly Gly Val Tyr
    690                 695                 700

Tyr Lys Lys Tyr Asp Thr Asn Leu Leu Gln Asn Ile Glu Ser Glu Leu
705                 710                 715                 720

Ala Lys Leu Lys Asp Ala Ile Leu Thr Glu Glu Ser Glu Thr Ser Leu
                725                 730                 735

Asp Tyr Ser Glu Thr Met Tyr Ile Glu Ser Asn Val Gly Ser Phe Gly
            740                 745                 750

Val Ser Asp Leu Tyr Lys Ile Lys Lys Asn Asn Thr Leu Lys Gln Ser
        755                 760                 765

Ser Met Ile Val Asp Glu Tyr Asp Val Phe Lys Ser Tyr Leu Ile Tyr
770                 775                 780

<210> SEQ ID NO 8
<211> LENGTH: 108
<212> TYPE: PRT
```

<213> ORGANISM: Bacteriophage C1 polypeptide

<400> SEQUENCE: 8

```
Met Ile Tyr Leu Leu Ile Leu Asn Ser Ala Asp Phe Ile Ser Gly Ile
1               5                   10                  15

Leu Asn Gly Ile Ala Leu Gly Asp Ile Ser Ser Lys Lys Leu Lys Lys
            20                  25                  30

Gly Ile Ile Gly Lys Leu Leu Gln Trp Ile Val Ile Ala Val Thr Ile
        35                  40                  45

Thr Met Lys Pro Val Ile His Val Asp Leu Leu Thr Tyr Val Ile Ile
50                  55                  60

Tyr Tyr Tyr Ile Met Glu Val Ile Ser Ile Leu Glu Asn Val Ala Trp
65                  70                  75                  80

Tyr Leu Pro Val Pro Lys Lys Leu Leu Asn Val Leu Ala Gln Phe Lys
                85                  90                  95

Glu Ile Glu Asn Glu Val Lys Ser Asn Glu Gln Asp
            100                 105
```

<210> SEQ ID NO 9
<211> LENGTH: 72
<212> TYPE: PRT
<213> ORGANISM: Bacteriophage C1 light chain of PlyC (PlyC B)
      (formerly known as the alpha subunit)

<400> SEQUENCE: 9

```
Met Ser Lys Ile Asn Val Asn Val Glu Asn Val Ser Gly Val Gln Gly
1               5                   10                  15

Phe Leu Phe His Thr Asp Gly Lys Glu Ser Tyr Gly Tyr Arg Ala Phe
            20                  25                  30

Ile Asn Gly Val Glu Ile Gly Ile Lys Asp Ile Glu Thr Val Gln Gly
        35                  40                  45

Phe Gln Gln Ile Ile Pro Ser Ile Asn Ile Ser Lys Ser Asp Val Glu
50                  55                  60

Ala Ile Arg Lys Ala Met Lys Lys
65                  70
```

<210> SEQ ID NO 10
<211> LENGTH: 105
<212> TYPE: PRT
<213> ORGANISM: Bacteriophage C1 polypeptide

<400> SEQUENCE: 10

```
Met Ile Glu Glu Trp Val Lys His Pro Ser Leu Asn Tyr Tyr Ile Ser
1               5                   10                  15

Ser Tyr Gly Arg Val Lys Asn Ser Lys Gly Leu Ile Met Lys Gln His
            20                  25                  30

Ile Cys Asn Gly Tyr Lys Arg Ile Lys Leu Val Lys Asp Gly Ile Lys
        35                  40                  45

Lys Asn Tyr Tyr Val His Arg Leu Val Ala Glu Thr Phe Ile Pro Lys
50                  55                  60

Leu His Val Asp Tyr Val His His Ile Asp His Asp Lys Leu Asn
65                  70                  75                  80

Asn Trp Val His Asn Leu Glu Trp Cys His Tyr Gln Thr Asn Leu Leu
                85                  90                  95

Tyr Glu Arg Glu Asn Leu Phe Asn Glu
            100                 105
```

<210> SEQ ID NO 11
<211> LENGTH: 472
<212> TYPE: PRT
<213> ORGANISM: Bacteriophage C1 heavy chain of PlyC (PlyC A)
    (formerly known as the beta subunit)

<400> SEQUENCE: 11

Met Lys Gly Arg Ile Tyr Leu Met Ser Lys Lys Tyr Thr Gln Gln Gln
 1               5                  10                  15

Tyr Glu Lys Tyr Leu Ala Gln Pro Ala Asn Asn Thr Phe Gly Leu Ser
            20                  25                  30

Pro Gln Gln Val Ala Asp Trp Phe Met Gly Gln Ala Gly Ala Arg Pro
        35                  40                  45

Val Ile Asn Ser Tyr Gly Val Asn Ala Ser Asn Leu Val Ser Thr Tyr
50                  55                  60

Ile Pro Lys Met Gln Glu Tyr Gly Val Ser Tyr Thr Leu Phe Leu Met
65                  70                  75                  80

Tyr Thr Val Phe Glu Gly Gly Ala Gly Asn Trp Ile Asn His Tyr
            85                  90                  95

Met Tyr Asp Thr Gly Ser Asn Gly Leu Glu Cys Leu Glu His Asp Leu
        100                 105                 110

Gln Tyr Ile His Gly Val Trp Glu Thr Tyr Phe Pro Pro Ala Leu Ser
    115                 120                 125

Ala Pro Glu Cys Tyr Pro Ala Thr Glu Asp Asn Ala Gly Ala Leu Asp
130                 135                 140

Arg Phe Tyr Gln Ser Leu Pro Gly Arg Thr Trp Gly Asp Val Met Ile
145                 150                 155                 160

Pro Ser Thr Met Ala Gly Asn Ala Trp Val Trp Ala Tyr Asn Tyr Cys
                165                 170                 175

Val Asn Asn Gln Gly Ala Ala Pro Leu Val Tyr Phe Gly Asn Pro Tyr
            180                 185                 190

Asp Ser Gln Ile Asp Ser Leu Leu Ala Met Gly Ala Asp Pro Phe Thr
        195                 200                 205

Gly Gly Ser Ile Thr Gly Asp Gly Lys Asn Pro Ser Val Gly Thr Gly
    210                 215                 220

Asn Ala Thr Val Ser Ala Ser Glu Ala Asn Arg Glu Lys Leu Lys
225                 230                 235                 240

Lys Ala Leu Thr Asp Leu Phe Asn Asn Asn Leu Glu His Leu Ser Gly
                245                 250                 255

Glu Phe Tyr Gly Asn Gln Val Leu Asn Ala Met Lys Tyr Gly Thr Ile
            260                 265                 270

Leu Lys Cys Asp Leu Thr Asp Asp Gly Leu Asn Ala Ile Leu Gln Leu
        275                 280                 285

Ile Ala Asp Val Asn Leu Gln Thr Asn Pro Asn Pro Asp Lys Pro Thr
    290                 295                 300

Val Gln Ser Pro Gly Gln Asn Asp Leu Gly Ser Gly Ser Asp Arg Val
305                 310                 315                 320

Ala Ala Asn Leu Ala Asn Ala Gln Ala Gln Val Gly Lys Tyr Ile Gly
                325                 330                 335

Asp Gly Gln Cys Tyr Ala Trp Val Gly Trp Trp Ser Ala Arg Val Cys
            340                 345                 350

Gly Tyr Ser Ile Ser Tyr Ser Thr Gly Asp Pro Met Leu Pro Leu Ile
        355                 360                 365

Gly Asp Gly Met Asn Ala His Ser Ile His Leu Gly Trp Asp Trp Ser
    370                 375                 380

```
Ile Ala Asn Thr Gly Ile Val Asn Tyr Pro Val Gly Thr Val Gly Arg
385                 390                 395                 400

Lys Glu Asp Leu Arg Val Gly Ala Ile Trp Cys Ala Thr Ala Phe Ser
            405                 410                 415

Gly Ala Pro Phe Tyr Thr Gly Gln Tyr Gly His Thr Gly Ile Ile Glu
        420                 425                 430

Ser Trp Ser Asp Thr Thr Val Thr Val Leu Glu Gln Asn Ile Leu Gly
    435                 440                 445

Ser Pro Val Ile Arg Ser Thr Tyr Asp Leu Asn Thr Phe Leu Ser Thr
450                 455                 460

Leu Thr Gly Leu Ile Thr Phe Lys
465                 470

<210> SEQ ID NO 12
<211> LENGTH: 574
<212> TYPE: PRT
<213> ORGANISM: Bacteriophage C1 polypeptide

<400> SEQUENCE: 12

Met Thr Leu Ser Lys Ile Lys Leu Phe Tyr Asn Thr Pro Phe Asn Asn
 1               5                  10                  15

Met Gln Asn Thr Leu His Phe Asn Ser Asn Glu Glu Arg Asp Ala Tyr
            20                  25                  30

Phe Asn Ser Lys Phe Asp Val His Glu Phe Thr Ser Thr Phe Asn Tyr
        35                  40                  45

Arg Asn Met Lys Gly Val Leu Arg Val Thr Ile Asp Leu Val Ser Asp
50                  55                  60

Arg Ser Cys Phe Glu Gln Leu Met Gly Val Asn Tyr Cys Gln Val Gln
65                  70                  75                  80

Tyr Ile Gln Ser Asn Arg Val Glu Tyr Leu Phe Val Thr Asp Ile Gln
                85                  90                  95

Gln Leu Asn Asp Lys Val Cys Glu Leu Ser Leu Val Pro Asp Val Val
            100                 105                 110

Met Thr Tyr Thr Gln Gly Asn Val Leu Asn Thr Leu Asn Asn Val Asn
        115                 120                 125

Val Ile Arg Gln His Tyr Thr Gln Thr Glu Tyr Glu Gln Asn Leu Glu
130                 135                 140

Gln Ile Arg Ser Asn Asn Asp Val Leu Ala Thr Ser Thr Met Arg Val
145                 150                 155                 160

His Ala Ile Lys Ser Glu Leu Phe Thr Gln Leu Glu Tyr Ile Leu Thr
                165                 170                 175

Ile Gly Ala Asn Leu Arg Lys Ser Phe Gly Thr Ala Glu Lys Pro Lys
            180                 185                 190

Phe Pro Ser Ser Ser Gly Ser Thr His Asp Gly Ile Tyr Asn Pro Tyr
        195                 200                 205

Asp Met Tyr Trp Phe Asn Asp Tyr Glu Ser Leu Lys Glu Val Met Asp
210                 215                 220

Tyr Leu Thr Gly Tyr Pro Trp Ile Gln Gln Ser Ile Lys Asn Val Thr
225                 230                 235                 240

Ile Ile Pro Ser Gly Phe Ile Lys Gln Glu Ser Leu Asn Asp His Glu
                245                 250                 255

Pro Val Asn Gly Gly Asp Leu Ser Val Arg Lys Leu Gly Lys Gln Gly
            260                 265                 270

Val Ser Asn Gln Lys Asp Phe Asn Ala Ile Ser Leu Asp Tyr Gln Ser
```

```
                275                 280                 285
Leu Met Phe Thr Leu Gly Leu Asn Pro Ile Asn Asp Lys His Leu Leu
    290                 295                 300

Arg Pro Asn Ile Val Thr Ala Glu Leu Thr Asp Tyr Ala Gly Asn Arg
305                 310                 315                 320

Leu Pro Ile Asp Leu Ser Leu Ile Glu Thr Asn Leu Glu Phe Asp Ser
                325                 330                 335

Phe Val Thr Met Gly Ala Lys Asn Glu Ile Lys Val Tyr Val Lys Asn
                340                 345                 350

Tyr Asn Ala Arg Gly Asn Val Gly Gln Tyr Ile Asp Asn Ala Leu
            355                 360                 365

Thr Ile Asn Asn Phe Asp Thr Ile Gly Phe Ser Val Asp Ser Gly Glu
    370                 375                 380

Leu Gly Lys Ala Asn Ser Ala Tyr Ser Arg Glu Leu Ser Asn Ser Arg
385                 390                 395                 400

Gln Met Ser Ser Arg Ile Asn Thr Val Leu Asp Asn Asp Ala Ser Val
                405                 410                 415

Lys Asp Arg Leu Phe Asn Ala Ile Ser Leu Ser Gly Gly Leu Ser Ile
            420                 425                 430

Lys Ser Ala Leu Ser Gly Phe Asn Asn Glu Tyr Glu His Tyr Arg Asp
        435                 440                 445

Gln Lys Ala Gln Phe Lys Gln Met Asp Ala Leu Pro Asn Ala Ile Thr
    450                 455                 460

Glu Gly His Val Gly Tyr Ala Pro Leu Phe Lys Gln Asp Lys Phe Gly
465                 470                 475                 480

Val His Leu Arg Leu Gly Arg Ile Ser Gln Asp Glu Leu Asn Asn Val
                485                 490                 495

Lys Lys Tyr Tyr Asn Met Phe Gly Tyr Glu Cys Asn Asp Tyr Ser Thr
            500                 505                 510

Lys Leu Ser Asp Ile Thr Ser Met Ser Ile Cys Asn Trp Val Gln Phe
        515                 520                 525

Lys Gly Ile Trp Thr Leu Pro Asn Val Asp Thr Gly His Met Asn Met
    530                 535                 540

Leu Arg Ala Leu Phe Glu Ala Gly Val Arg Leu Trp His Lys Glu Ser
545                 550                 555                 560

Asp Met Ile Asn Asn Thr Val Val Asn Asn Val Ile Ile Lys
                565                 570

<210> SEQ ID NO 13
<211> LENGTH: 430
<212> TYPE: PRT
<213> ORGANISM: Bacteriophage C1 polypeptide

<400> SEQUENCE: 13

Met Arg Gly Thr Asn Tyr Met Lys Phe Tyr Ile Asn Pro Phe Asp Gln
  1               5                  10                  15

His His Asp His Met Ser His His Asp His Glu His Trp Lys Glu Leu
                20                  25                  30

Gln Phe Ser Lys Ala Val Ala Asp Ala Ile Asn Ala Asn Ser Glu Lys
            35                  40                  45

Asn Ile Glu Gln Asp Gly Arg Leu Asp Gly His Asp Lys Asp Val Gln
    50                  55                  60

Asp Leu Lys Asn Ala Asp Leu Glu Ile Ile Gln Gln Ile Asp Glu Val
65                  70                  75                  80
```

```
Ala Ala Gln Ala Ala Glu Asn Lys Asn Leu Leu Gly Asn Leu Lys Gly
                85                  90                  95

Ala Glu Thr Ser Thr Ala Lys Ser Asn Ile Tyr Asn Gly Ile Gln Val
            100                 105                 110

Asp Val Lys Val Ala Pro Gln Ser Asp Asn Gly Leu Lys Ile Thr Thr
        115                 120                 125

Asp Gly Leu His Val Val Asp Tyr Thr Ser Lys Ile Ala Glu Ile Glu
    130                 135                 140

Gln Leu Ile Asp Glu Ile Leu Thr Pro Glu Gly Ser Asp Val Thr Met
145                 150                 155                 160

Glu Gln Ile Arg Ala Met Ile Glu Asn Leu Ser Gln Glu Phe Gly Glu
                165                 170                 175

Ala Asp Ala Gly Leu Lys Leu Gln Ile Asp Asn Met Glu Lys Arg Leu
            180                 185                 190

Ile Ala Leu Asp Ile Pro Asp Ile Asp Pro Leu Thr Gln Lys Ile Glu
        195                 200                 205

Leu Leu Asp Ala Asp Ile Leu Gly Val Lys Gln Ile Ser Thr Tyr Thr
    210                 215                 220

Glu Met Met Asn Ser Leu Ala Thr Phe Gly Ser Arg Glu Gly Ser Lys
225                 230                 235                 240

Ala Ile Arg Phe Asn Pro Val Gly Asn Ala Ser Thr Gly Thr Gln Ile
                245                 250                 255

Asp Pro Asn Gly Gly Met Asn Leu Leu Tyr Gln Ser His Thr Phe Gln
            260                 265                 270

Val Arg Gly Val Thr Lys Arg Phe Glu Phe Leu Leu Leu Asp Ile Trp
        275                 280                 285

His Met Thr Phe Arg Gly Thr Gly Trp Pro Glu Gln Val Ala Asp Met
    290                 295                 300

Tyr Tyr Phe Met Leu Asp Ile Tyr Ala Glu Gly Val Thr Asp Arg Leu
305                 310                 315                 320

Lys His Val Leu Ser Asn Asn Ala Ile Thr Met Asn Asp Phe His Gln
                325                 330                 335

Phe Asp Asn Asn Ala Gln Val Lys Lys Trp Tyr Pro Val Val Phe Thr
            340                 345                 350

Leu Tyr Gly Asn Asp Asp Lys Glu Glu Met Tyr Leu Val Ala Gln Gly
        355                 360                 365

Leu Gly Thr Ser Gly Leu Asp Thr Glu Ser Leu Asp Asn Phe Arg Ala
    370                 375                 380

Pro Ala Thr Gly Thr Pro Tyr Val Ile Glu Thr Trp Leu Asp Pro Val
385                 390                 395                 400

Thr Gly Thr Glu Tyr Met Pro Ala Tyr Gln Ala Asp Gly Tyr Lys His
                405                 410                 415

Lys Pro Phe Asn Gln Trp Val Thr Val Glu Asp Phe Tyr Ser
            420                 425                 430

<210> SEQ ID NO 14
<211> LENGTH: 236
<212> TYPE: PRT
<213> ORGANISM: Bacteriophage C1 polypeptide

<400> SEQUENCE: 14

Met Arg Leu Phe Glu Leu Ile Tyr Lys Glu Val Val Lys Asn Gly Tyr
1               5                   10                  15

Ser Pro Phe Arg Ser Pro Glu Asn Arg Ile Val Val Phe Glu Asp Lys
            20                  25                  30
```

Ala Gln Ile Glu Thr Lys Ile Met Met Tyr Asp Glu Asp Val Gln Lys
                35                  40                  45

Val Val Asn Glu Leu Ile Phe Thr Gly Ser Lys Val Asn Glu Asp Phe
 50                  55                  60

Arg Glu Glu Phe Val Asn Tyr Phe Phe Asn Arg Glu Pro His Trp Asp
 65                  70                  75                  80

Ser Leu Tyr Ile Phe Arg Ala Lys Leu Lys Gly Ile Leu Lys Thr Lys
                85                  90                  95

Glu Ala Val Leu Asn Met Leu Tyr Leu Lys Ser Thr Glu Leu Leu Leu
                100                 105                 110

Gly Glu Ser Met Ser Lys Ser Glu Gly His Ser Ser Asn Glu Asn Arg
                115                 120                 125

Ser Arg Asp Asn Ser Thr Asn Glu Ser Asn Gly Glu Asn Arg Gly Ala
        130                 135                 140

Asn Ala His Ser Thr Asn Pro Asp Asp Val Thr Asp Thr Asp Leu Glu
145                 150                 155                 160

Thr Ala Asn Leu Ser Tyr Ala Asp Asn Leu Asp Lys Ser Tyr Asn Glu
                165                 170                 175

Ser Val Asn Val Ser His Ser Lys Gly Ile Ser Ser Ser Gln Gly Ser
                180                 185                 190

Ser Asn Asn Asn Ser Asn Ser Thr Asn Thr Gln Phe Asn Thr Lys Ala
        195                 200                 205

Leu Glu Glu Tyr Glu Ala Phe Lys Gln Lys Ile Phe Asp Glu Leu Asp
    210                 215                 220

Ile Lys Leu Phe Ser Gln Leu Phe Tyr Glu Gly Tyr
225                 230                 235

<210> SEQ ID NO 15
<211> LENGTH: 317
<212> TYPE: PRT
<213> ORGANISM: Bacteriophage C1 polypeptide

<400> SEQUENCE: 15

Met Gln Ile Thr Ser Gly Ile Lys Pro Ser Glu Met Asn Tyr Lys Met
 1               5                  10                  15

Ser Thr Phe Thr Asp Asp Ile Ala Glu Arg Val Lys Leu His Lys Gln
                20                  25                  30

Asn Tyr Phe Asn Ile Ile Tyr Ser Arg Tyr Val Glu Phe Leu Pro Leu
                35                  40                  45

Leu Ile Ser Tyr Glu Asn Tyr Asp Leu Asp Ser Leu Leu Ile Glu Ser
 50                  55                  60

Tyr Leu Arg Ala Gly Tyr Gly Val Ala Ile Gly Glu Thr Lys Thr Gly
 65                  70                  75                  80

Lys Ile Asp Val Leu Gly Tyr Cys Ser Val Asn Thr Asn Tyr Leu Gln
                85                  90                  95

Pro Ile Lys Glu Pro Leu Gln Gly Lys Asp Ile Thr Phe Ile His Asn
                100                 105                 110

Asn Ile Leu Pro Lys Gly Lys Tyr Lys Glu Leu Thr Arg Tyr Ser Asp
        115                 120                 125

Gly Asn Phe Val Val Leu Arg Asn Lys Arg Ala Ser Phe Leu Cys Asp
        130                 135                 140

Tyr Asn Ile Ile Thr His Tyr Val Met Glu Met Ser Glu Ile Ala Asn
145                 150                 155                 160

Ser Arg Tyr Ser Ile Ser Ile Gln Ala Lys Val Asn Thr Phe Ile Arg

-continued

```
                165                 170                 175
Asn Glu Gly Gly Ser Lys Asp Gly Gln Val Met Ala Asn Asn Leu Phe
            180                 185                 190

Asn Gly Val Pro Tyr Thr Ala Thr Thr Pro Lys Phe Asp Pro Glu Glu
        195                 200                 205

His Ile Leu Thr Phe Asn Asn Ala Ser Ala Val Ser Phe Leu Pro Glu
    210                 215                 220

Leu Lys Arg Glu Gln Gln Asn Lys Ile Ser Glu Leu Asn Ala Met Leu
225                 230                 235                 240

Gly Leu Asn Thr Leu Gly Val Asp Lys Glu Ser Gly Val Ser Glu Ile
                245                 250                 255

Glu Ala Gln Ser Asn Thr Ala Phe Lys Lys Ala Asn Glu Asn Ile Tyr
            260                 265                 270

Leu Gly Ile Arg Asn Glu Ala Leu Asn Leu Ile Asn Asn Lys Tyr Gly
        275                 280                 285

Leu Asn Ile His Ala Glu Tyr Arg Asp Asn Met Val Ala Glu Leu Ser
    290                 295                 300

Ser Ile Glu Lys Leu Gln Ile Val Ser Glu Val Ala Gln
305                 310                 315

<210> SEQ ID NO 16
<211> LENGTH: 392
<212> TYPE: PRT
<213> ORGANISM: Bacteriophage C1 polypeptide

<400> SEQUENCE: 16

Met Ala Asp Glu Thr Thr Asn Val Ala Gly Ala Ile Val Ala Ser Leu
1               5                   10                  15

Asn Asp Phe Asn Ala Asp Asn Gly Lys Ser Trp Thr Phe Gly Thr Asn
            20                  25                  30

Trp Asn Ala Val Gly Thr Asp Phe Glu Thr Tyr Thr Asn Gln Tyr Leu
        35                  40                  45

Phe Pro Lys Leu Asn Glu Thr Leu Ile Val Glu Thr Ala Ala Gly Asn
    50                  55                  60

Arg Leu Asp Trp Leu Ala Lys Glu Ile Asp Phe Ile Gly Gln Tyr Ser
65                  70                  75                  80

Glu Glu Tyr Val Ile Leu Asp Thr Val Pro Val Glu Leu Asp Leu Ser
                85                  90                  95

Lys Ser Ala Gln Leu Met Leu Glu Arg Asn Tyr Pro Lys Ile Ala Ser
            100                 105                 110

Lys Leu Tyr Gly Ala Gly Ile Leu Lys Lys Leu Lys Phe Thr Leu Asn
        115                 120                 125

Asp Asn Ile Gln Arg Gln Gln Phe Ala Thr Leu Gly Asp Ala Thr Lys
    130                 135                 140

Phe Ala Val Gln Val Tyr Lys Lys Ile Ala Asp Ile Asn Ile Ser
145                 150                 155                 160

Glu Glu Gln Glu Leu Lys Ala Ile Ile Met Asp Tyr Thr Ser His Ile
                165                 170                 175

Ala Asp Val Arg Glu Val Glu Ser Gly Ala Thr Met Gln Gln Phe Ile
            180                 185                 190

Asn Lys Val Tyr Thr Ala Ile Leu Asn Leu Gln Asn Asn Ser Ala Lys
        195                 200                 205

His Asn Glu Ala Ala Gln Ala Ser Gly Gly Ala Val Gly Arg Phe Thr
    210                 215                 220
```

```
Thr Asn Thr Lys Leu Lys Asp Met Leu Ile Val Thr Thr Asp Glu Met
225                 230                 235                 240

Lys Val Glu Ile Leu Asn Ser Phe Leu Ala Asn Thr Phe His Ala Glu
            245                 250                 255

Gly Leu Asp Ile Thr Ser Gln Ile Ile Ser Phe Glu Asp Leu Gly Gly
        260                 265                 270

Val Tyr Lys Ala Ala Glu Asp Ile Thr Val Asp Ala Thr Ile Gln Gly
    275                 280                 285

Val Met Ala Ala Met Gly Asp Tyr Gln Val Lys Ala Gly Asp Val Ile
290                 295                 300

Pro Ala Gly Thr Val Phe Thr Tyr Glu Ile Pro Ala Glu Ala Leu Gly
305                 310                 315                 320

Asp Gln Ala Asp Ala Leu Val Glu Val Lys Pro Asp Ser Asp Glu Phe
            325                 330                 335

Val Ala Ile Phe Asp Val Arg Ser Ile Arg Tyr Lys Arg Tyr Thr Arg
        340                 345                 350

Asn Met Leu Lys Ala Pro Phe Tyr Asn Gly Glu Phe Asp Glu Val Thr
    355                 360                 365

His Trp Ile His Tyr Tyr Ser Met Lys Ala Ile Ser Pro Phe Tyr Asn
370                 375                 380

Lys Val Val Ile Lys Arg Ala Asn
385                 390

<210> SEQ ID NO 17
<211> LENGTH: 51
<212> TYPE: PRT
<213> ORGANISM: Bacteriophage C1 polypeptide

<400> SEQUENCE: 17

Met Leu Pro Glu Glu His Thr Asn Thr Ile His Asn Met Thr Lys Asp
1               5                   10                  15

Asp Phe Gly Ile Ser Lys Leu Asp Lys Ser Asn Glu Leu Asn Glu Thr
            20                  25                  30

Met Thr Ile Gly Gln Gly Lys Ser Gln Asp Glu Val Thr Thr Ala Leu
        35                  40                  45

Phe Asn Leu
    50

<210> SEQ ID NO 18
<211> LENGTH: 56
<212> TYPE: PRT
<213> ORGANISM: Bacteriophage C1 polypeptide

<400> SEQUENCE: 18

Met Thr Lys Glu Glu Leu Leu Ala Lys Ile Ala Ala Leu Glu Glu Lys
1               5                   10                  15

Thr Ala Arg Leu Glu Glu Leu Ala Thr Ala Pro Ala Pro Ala Asp Glu
            20                  25                  30

Pro Lys Gln Gln Glu Glu Gln Glu Pro Glu Val Thr Pro Ile Asp Glu
        35                  40                  45

Ile Glu Glu Trp Leu Lys Glu Asp
    50                  55

<210> SEQ ID NO 19
<211> LENGTH: 64
<212> TYPE: PRT
<213> ORGANISM: Bacteriophage C1 polypeptide
```

<400> SEQUENCE: 19

| Met | Ala | Glu | Asn | Lys | Pro | Leu | Glu | Glu | Gln | Asp | Gly | Lys | Asn | Tyr | Glu |
| 1 | | | | 5 | | | | | 10 | | | | | 15 | |

| Tyr | His | Ile | Tyr | Ala | Tyr | Val | Asn | Gly | Lys | Trp | Ile | Lys | Val | Tyr | Val |
| | | | 20 | | | | | 25 | | | | | 30 | | |

| Thr | Arg | Asp | Val | Glu | Asp | Arg | Asp | Lys | Val | Met | Leu | Thr | Leu | Lys | Asn |
| | | 35 | | | | | 40 | | | | | 45 | | | |

| Asp | Gly | Asp | Met | Ile | Lys | Asp | Tyr | Phe | Tyr | Glu | Thr | Lys | Glu | Ile | Lys |
| | 50 | | | | | 55 | | | | | 60 | | | | |

<210> SEQ ID NO 20
<211> LENGTH: 55
<212> TYPE: PRT
<213> ORGANISM: Bacteriophage C1 polypeptide

<400> SEQUENCE: 20

| Met | Asn | His | Thr | Arg | Thr | Thr | His | Ile | Ser | Val | Thr | Glu | Thr | Ser | Ile |
| 1 | | | | 5 | | | | | 10 | | | | | 15 | |

| Asp | Thr | Leu | Arg | Asp | Ile | Tyr | Ala | His | Glu | Val | Ala | Thr | Tyr | Gly | Met |
| | | | 20 | | | | | 25 | | | | | 30 | | |

| Glu | Asn | Val | Lys | Val | Val | Ser | Phe | Thr | Met | Asn | Asn | Glu | Gly | Val | Thr |
| | | | 35 | | | | | 40 | | | | | 45 | | |

| Met | Val | Tyr | Asp | Ile | Ile | Lys |
| | 50 | | | | | 55 |

<210> SEQ ID NO 21
<211> LENGTH: 16687
<212> TYPE: DNA
<213> ORGANISM: Bacteriophage C1 entire genomic sequence

<400> SEQUENCE: 21

```
ttttagtata tagcgtagtg atttctccct cccccctcct aatgtaaatg ttttcagaaa      60
acactttcat aaatatttct gttgacacca cagctgcaac atgatataat taatacataa     120
ataagaaaga ggtacacaac atggttcaca aagtaacaac acgcaaatca ctaactgaca     180
caagcattga cagattgtta agcacatacg cgcagattgt agcgacttac ggctcaccaa     240
atgttcaaat agtccgcttc gttaagaacg gaaatagcgc aacaatgact tacgacataa     300
caatattaat ttaaaaaagt aaactttcta gttgacaacg cataacggt tgatataat      360
tagtatataa aatagagata gaggtaacaa caatgacatt tcaaaaagtc cttagattta     420
aagacgtatc acgtgaagag atgatgaaaa actacaggga attaacagcc cgctatggta     480
tgaataacat catcttagaa gatttgaaat acgacgttga atacaacgaa tactcattca     540
atatactaat caagctataa ggagatattc catgaaaatt agaatgaaaa caatttacac     600
ttttcaaca acaatagcaa cactagctct tggtgtaaac ctattaatgg ataagggaga     660
caacaacaat gttaacactg ataatacttt taataatagc aaccctattg tacaagttga     720
caacaattct agtgaagcca ctactactat tactagtgat actaatgata tcaagtggc     780
tgccgacgat actaatgata ctgaacaact agattatttt caaccatacg aatacctata     840
catgccaagt acaaacgtat catcaattag agacggatac tacttagtat caggtggtaa     900
tacattagca gctgttcaaa taacaaatgg ttacacaact gatgaattta gacttaaaaa     960
tatatccgcg gaacaatgga cagtatctca acaacaaatg aagactttg tttactggtt    1020
acgtgaagtt agtccaagcg gatacaatca aaaaagtcta gaaaataatt ttaaaatttt    1080
tatcaaaaag tagttgacac tgataacaca acatgctata atagatacat aaataagaaa    1140
```

-continued

```
ggaagtatcc aaaatatgtt ttatacacca attagagagt ataggttaga ttattatgac    1200
ggtgaaaaat accaatcagt catctgcaca gaccatgagt taaatcaaac actatctgaa    1260
ttaatcaata aatacggtga aagtaatgtc gaaccaataa aggagattag ataatgacag    1320 ctttattga tacaatcaag aaatatcaac ttgaaccaga cgaaccaaaa acggtaacag     1380
tagaaaaaaa aaagtgaaac aaaatataga cgccatcgcc tcattatcaa caagacggta    1440
ttgaacctat tgaatatata atgtcacaca acatgaattt caatatcgga aatgttatca    1500
aatacgtaac aagagcaggc aagaaacagg gtgagcctat agagaaagac ttacaaaaag    1560
caattgatta tttaaagttt gaattagaaa gggttaaaaa atgaccaaat acctagtaac    1620
tgttatcaac gaccaacacg ttttaagcga acatgaattc acaagtaaga aacacgcttt    1680
aagtttcttt aaacgactac aagcagacga aactgtccta tcatcagaaa tagaggaaat    1740
ataatatgaa acacaagaa tggtacttag taaatttcgg tttatacgaa accaaaacac     1800
aagaaatgga acaaattct agatattttg aggataaaca agccgcccta gacttcttct     1860
acactctagc aaacgaggga tactacgact gggcgcatgt atatagcaac ttagaaatgg    1920
aaattatctt ataatgaaac aaacaaatat cgacgcactt ttcggaaaag gagaccacca    1980
gttaatgaac aaagaaagta aatacctatc aacattattt atcaatatag aggaattatc    2040
agtacattta tcatcagtaa ctttatttat cgatgaatat gaacagttaa aagaaaatgc    2100
tattaagagc aaaaacgta aatgcttgaa actcggtaat acactatact ttaccaataa     2160
taactacgct actaaattat ataatagctt actagcactt ggctttaacg gtgctaacag    2220
cttttcatca ggtgaacaaa catatgttat ttcactaaca ggcggtaatg caacattaac    2280
aactgtcaaa acacattatg gagatgtaaa atatcactat aaacacgaaa aattaccagt    2340
taagaagatt gtcaatgatt tctggttatc ggaacaagag tacgtatata ctaattcaat    2400
taaattagct tacgcattac ttgatttata aagactatg ggatactcaa cacttaatac     2460
tataaaataa tttcaaaaat aagaacaaaa gtattgacaa atataataaa agctgttata    2520
attaatatat ataagttaag taagaaagaa aacttacagt caaactcacg tcaatataaa    2580
aacattagga gaaaacaaa atggcaatta acttcacaaa catcggattc atcaacttca     2640
acaaagaata caacaaagtt cttaaaaacg gagctatcac agctagcatg tcagcgtcac    2700
aaaaagacgt taaggtgaa tacgtagacg aatatcacaa cgtaactatt cctaaaaaag     2760
tagcagacca aattaaacca cttattaata cagaattatg tgacattcaa ggggttatct    2820
ctcgtaacga taagtataca aacatcacca tcttaggtgc taaaaaacac gtcaaagcgg    2880
aagccgtaga cgtagcagac gaagatttac cattctaata taattaatga aaggagatga    2940
ggaaaggaca ataaaaagtc tctttcctct ttttaaatat atggctaaca aaagacaacg    3000
taaaaaacaa ctaaaacaac aatatggggt tggtcataaa tataccccta aactaagtca    3060
aacacaacaa aaacaagctg atttctaaa atcaatcggt caaaaattca ctaattatca     3120
aacagttaca attgataaaa catattcaaa aaatcaagaa ttgctagata cagctaacga    3180
agctcttcat agactaggta tcttctttga tggtagtgaa aaaatcaagt tgcagcaggt    3240
gacagatgat gatttgagat atatcattaa taagttacaa cctctttttgg aaagtgtgac    3300 aatgagatat aagaagtttc tgacaaatac ataccgctca acaatagag actatcgatt      3360 agactggtta cttaaatcgg ccatctctaa aaaacttaaa aacgctcaaa cagttagggg    3420
tctagtagtt gccattaata aaatggatag agattttaag gaatacgata agaaattacg    3480
```

```
taaatcaagt aaacaaggca acccatttgg gtttgtcgtt gtaaaatata gtgaaatggg   3540
gttaatgtaa tggcaagaaa agtaaagaaa acgataaaaa caatcttcaa gaacgaggaa   3600
gaggagttta aaacactgct taatgactat cgcaagaaat atttaccatc taaatacaat   3660
caactagaat tacttgattg gctatgttca gacgaaatac ttcactacat gtcaataact   3720
tctcgtggtg acgtaaaatc gtttaattac attggggcat tggcatggct atcatatcat   3780
ttaaactttg gaactatgtt attggtacgt cactggtcat taatgacaa aatggctgaa    3840 atggtatttg aaattattag aactgttggt atgtttgaca ttgaaaatgt tgggatacaa   3900
gctaaagctg attatctaac aataactatc gagggtcgag aagtctttat tataaccaat   3960
ctaaacaacg ctagtgactt gaaacagtca tcagcggttc ttcgtaacta cccagttgtt   4020
ttatatgatg aattcctaac attaggagag gattacgtca caaatgagtt ggcaaaacta   4080
caaacaatta tcaagtccat tgaccgtatg ggtaaacgac catacataaa aaggcctaaa   4140
ataatttatc taggaaaccc agttaatttt gacagtccta ttctaccagc tctaaacatc   4200
ttctacgcac tacaaaatca agaaattaat actatccaac aacatggtaa aacaattctt   4260
gaattacgtc ggaatgacga ggtaaacgag gaaaagacaa ctggttactt tgaggatagt   4320
gttgatagtg atattacagg tgaatttaac ttttcaaact atcggctagc cgaccaacaa   4380
acatataata aagcactaac caacggtaca ctatataaga taagactaga ggacaagctg   4440
tcatacgtta ttttggaaag tgacaacgaa tatatattat ccatagaaga aagcaaactt   4500
gatgaaaatt actgcataca ccttaaagat gaaacggcaa catgtgaata cctaaaacca   4560 agttttata aagatagttt cataaaacgt ttccaaaaag gtcatttaa ctttaaagac     4620 agtttctctc gtacattcat tgagggtaac gaggacttac aacgcttaaa cttcttcaaa   4680
cttaacgctg tagcaagtac agaccacgaa gacgcttacg ccaatattgt tagggaaagt   4740
tggatttcaa gacttgctaa aatctatgaa caatgatata atagtttata gaaagaggta   4800
tcacaatgaa agaatttgaa caatatctaa agtcattcaa aggtcaaaag gttacctctg   4860
ttgacttata ttgtgatata gaaaccgcaa ctattaataa aaatagcgga cagaaacacg   4920
ctagtacata tcactcgttt acctattcat tggccgtatc atacttcaaa actggggaag   4980
aattccctag tgttgtcgtg tttaatcact tcaaacagtt atttgatttt attgagaaaa   5040
gcaagattag aaagtctatc gaatttcgtt taatatttca caatggcgct aaatacgata   5100
atcattttat ggttagtgaa atacaacgtg atatagataa tgtgcgtcta tttaaccaga   5160
ctattaaaca agttaaccat ataacagacc tagatttatc aaaaaaacaa ggtaaacaaa   5220
tgaggaatga tgttaatatg gtattggaac gtcgggtacg ttcatctaat aaccttgatg   5280
gtgatatgtg gatatatggc cgacattatg aaatggtaga tagttatcgt aagactaatg   5340
tgtcaattga actatgtgga cgaatgcttc ttaacaacgg acttattgac gaacaatact   5400
taaaaacaga ttttgagtac gacaaatacg atttagatac agatttaact tggcacgagg   5460
ttagaaagta ccgagaattc atcttcaatg acttagatga aaagcagatg aaatatatcc   5520
ataatgatgt tattattcta gccttgacat gtaaacacta ctctaaatta ttttatggat   5580
ttgattttga gaaacagaca ttcacacaga atatcaaaga ggaatacgca aactataatg   5640
acatggctaa attccaactg ttgaaacaaa ttggcgataa catgactggt aaacacttga   5700
aattaacaga ctattttatt caaggtcaaa atgcttatga ctactttaaa aattattata   5760
atggtggctt aaacctatat aacgataaat atatcggaaa gaaactagtt agagatgggt   5820
tctctattga cctgaatagc tcatatccaa cagtgatgta taaggaaaag ttaccaacct   5880
```

```
ttttagtaat ggtagatagt aaaccaactg accttaaaaa tatcggcagc actgacggtg    5940
attatatggt attttttaac atgttaatgg aagatgtaaa cgaccaaatc ctatcacgaa    6000
ttaagtctaa tgttatcaaa agtgccatag ttaaatattg gcgagtgaaa gacggctatg    6060
tgtggttaaa caatgtaatg attagtttaa tagaggaaat aacacatcaa aaattcaaca    6120
atctacatgt tcaatcattt agtgtatttg aatgtcatca cttcggagct agggacatta    6180
tagctaaaaa ttatttcatt aaaacacaag gaaagatgag caaagctctt aactgtacaa    6240
tggaaacaat tgacccgtta acattgaat taactgataa ggataaacct aaagaatatg    6300
acttctccca tgaaatggta gagggttcaa aggtactact aaacgggata tacggtatcc    6360
ctgccttacg tgcttacttt gattgttaca gacgggacga gaacggtcag ctgtataacg    6420
tatcaaacgg ttttgagaat aaggaacgta acattgtatt ttcagcaggt gtaacagctt    6480
ttgcagtaag aaacctattg ctgccactag gaaaattaac acaagatgaa atagatgatt    6540
atttctggta tgctgatact gatagtctat atatggataa aagagcattg cctaaactac    6600
ctaaatcaat gtttcataag atgaatttag gaggttggga tattgaacac gcaaacatat    6660
ctacattcta tgcctttaac cataaaaagt attgtttata cgatgatgat gataatgaaa    6720
tagttgtacg ttgtggtggt atatctaaag ccttaatcaa gaaatggata gctgaaagtc    6780
gcaacaatat tgattatttt attaataact tcttcattga cggtgtaaca atccctgcaa    6840
ccagagctat aaggaatgaa tggaatacca ttacgattta tgacggcact agcgaattaa    6900
aaaaaggggg ggtgtactac aaaaaatatg acacgaattt attacaaaat attgaaagtg    6960
aattagcaaa gttaaaagac gcaatattaa cagaggaaag cgaaacaagt ttagactatt    7020
ccgaaacaat gtacattgaa agtaatgtag gctctttcgg ggttagcgac ctatacaaga    7080
ttaaaaagaa taacactctt aagcaatcaa gtatgattgt agatgagtac gatgtcttca    7140 aatcataccct aatctattga caaataaagg ccactatgct ataataagtg taggaggttt    7200
tttatgatat atttgttaat actaaattcc gctgacttta ttagcggtat actcaatggt    7260
attgcattag gtgacatatc tagtaagaaa ctaaaaaaag gaattattgg caagttgctg    7320
caatggattg ttattgctgt aacaattaca atgaaaccag ttattcatgt tgacttactt    7380
acatatgtta tcatatacta ctatataatg gaagtaattt ccattcttga aaacgtcgca    7440
tggtacttac cagtgccaaa gaaactgcta aatgttttag cacaatttaa agaaatagaa    7500
aatgaggtaa aatcaaatga gcaagattaa tgtaaacgta gaaaatgttt ctggtgtaca    7560
aggtttccta ttccataccg atggaaaaga aagttacggt tatcgtgctt ttattaacgg    7620
agttgaaatt ggtattaaag acattgaaac cgtacaagga tttcaacaaa ttataccgtc    7680
tatcaatatt agtaagtctg atgtagaggc tatcagaaag gctatgaaaa agtaatgatt    7740
gaggagtggg tcaagcaccc ctccctcaat tactatataa gtagttatgg cagggtgaaa    7800
aactctaaag gtttaataat gaaacaacac atatgcaatg gttataagcg aattaaatta    7860
gtaaaggacg gtataaaaaa gaattactat gttcatcgct tagttgcaga acattcata    7920 cctaaactac atgttgacta tgttgtacat catattgacc atgataaact aaacaactgg    7980
gtacataact tagaatggtg tcattatcaa actaacctat tatatgaaag ggagaattta    8040
tttaatgagt aagaagtata cacaacaaca atacgaaaaa tatttagcac aaccagcaaa    8100
taacacattt gggttatcac ctcaacaggt tgctgattgg tttatgggtc aagctggtgc    8160
taggcctgtt attaactcgt atggggtaaa tgctagtaat ttagtatcaa cgtacatacc    8220
```

```
taaaatgcag gaatacggtg tatcatatac actattctta atgtatactg tctttgaggg    8280
aggcggcgca ggtaattgga ttaatcatta catgtacgat acggggtcta atggattaga    8340
gtgtttggaa cacgatttac aatacataca tggcgtctgg gaaacttatt ttccaccagc    8400
tttatctgcg ccagaatgtt acccagctac ggaagataac gcaggtgctt tagatagatt    8460
ttatcaatcg ctaccaggcc gaacatgggg tgatgttatg atacctagta caatggctgg    8520
taatgcttgg gtatgggctt ataactattg tgttaacaac caaggggctg ccccattagt    8580
ttactttggc aatccatacg atagtcaaat tgatagcttg cttgcaatgg gagctgaccc    8640
gtttacaggt ggttcaatta caggtgatgg aaaaaatcct agtgttggca ctgggaatgc    8700
taccgtttct gctagctcgg aagctaacag agagaagtta agaaagccc taacagattt     8760 attcaacaac aacctagaac atctatcagg tgaattctac ggtaaccaag tgttgaatgc    8820
tatgaaatac ggcactatcc tgaaatgtga tttaacagat gacggactta atgccattct    8880
tcaattaata gctgatgtta acttacgac taaccctaac ccagacaaac cgaccgttca     8940
atcaccaggt caaaacgatt tagggtcggg gtctgataga gttgcagcaa acttagccaa    9000
tgcacaggcg caagtcggta agtatattgg tgacggtcaa tgttatgctt gggttggttg    9060
gtggtcagct agggtatgtg gttattctat ttcatactca acaggtgacc caatgctacc    9120
gttaattggt gatggtatga acgctcattc tatccatctt ggttgggatt ggtcaatcgc    9180
aaatactggt attgttaact acccagttgg tactgttgga cgcaaggaag atttgagagt    9240
cggcgcgata tggtgcgcta cagcattctc tggcgctccg ttttatacag acaatacgg     9300 ccatactggt atcattgaaa gctggtcaga tactaccgtt acagtcttag aacaaaacat    9360
tttagggtca ccagttatac gcagcaccta tgaccttaac acattcctat caacactaac    9420
tggtttgata acatttaaat aaaaagaag agactgtaaa gtctcttttc ttattttata    9480
atgacgttat taacaactgt gttattaatc atgtcacttt ctttgtgcca taaccttaca    9540
cctgcttcaa acaaagctct taacatattc atatgcccag tgtctacgtt aggaagagtc    9600
catattccct tgaattgaac ccaattacaa attgacatag atgtaatgtc tgaaagtttt    9660
gttgaatagt cgttacactc atatccgaac atgttgtaat acttcttaac attgtttaac    9720
tcgtcttgtg atatacgacc caatctcaag tgtacaccga atttgtcttg tttaaataaa    9780
ggagcatatc caacatgccc ctccgtaatg gcatttggta aagcgtccat tgtttaaac    9840 tgggcttttt ggtctctgta gtgttcatat tcattgttaa aacctgatag tgctgactta    9900
atagacagtc cacctgacag agaaatagca ttgaacagtc tatctttaac actggcgtca    9960
ttgtcaagta cggtattgat acgtgatgac atttgacgtg aattagataa ctcacgacta   10020
taggctgaat tggcttttcc taactcacca ctgtcaacag agaaacctat agtatcaaag   10080
ttatttattg tgagggcatt gtcaatgtat tgaccaacgt tgttacctct agcgttatag   10140
tttttaacat ataccttat ttcgttcttc gctcccatag ttacaaaact atcaaattca    10200
agattagttt caattaaaga aaggtcgatt ggtaaacgat taccagcgta atctgttagc   10260
tcggctgtta ctatattagg ccttagtaaa tgtttatcat tgattgggtt taaacctagc   10320
gtaaacataa gtgattgata atctaaacta atagcattaa aatctttttg atttgataca   10380
ccctgcttac ctaatttacg aacagacaaa tcaccaccgt taactggttc gtggtcgttt   10440
aaactttctt gtttaataaa gccacttgga ataattgtta cgttttttat tgattgttgt   10500
atccaagggt agcctgtgag atagtccatt acctctttta gactttcata gtcattaaac   10560
caatacatgt cataagggtt gtaaatacca tcatgtgttg aaccactaga agatggaaat   10620
```

```
ttaggctttt ctgccgtacc aaaagattta cgtaagttag ctcctattgt tagtatgtac   10680
tcaagttgtg tgaacaactc tgatttgata gcgtgtactc tcatagtgct tgtagctaaa   10740
acgtcattgt tagaacgaat tgttctaaa ttctgttcat attcagtttg agtataatgt    10800
tgacgtataa cattaacgtt attgagtgtg tttaatacat ttccttgagt atatgtcata   10860
acaacgtctg gtactagaga cagttcacat accttgtcat taagttgttg aatgtcagtt   10920
acaaataagt attcaactct gtttgattga atgtattgta cttgacagta gttaacgccc   10980
attaactgct caaagcatga acggtcactt actaagtcta ttgtaaccct tagcacccct   11040
ttcatattcc tatagttaaa tgttgatgta aactcatgta catcaaactt actattgaaa   11100
taggcgtccc gttcctcatt tgaattgaaa tgcaaagtat tttgcatgtt gttaaacggt   11160
gtattataga ataattttat ttttgataag gtcattcttt ttgtcctcct gcttctatta   11220
taccataaaa acactagcta ggctagtgtt attgtttatt tttctagttt ttctttgata   11280
aactcatcaa tttgtttctg ttcaactttc ttgtcgtaca ttggtctctt tagtaattca   11340
ttgatttgtt cttgtgttag tgccattgtt tatctccttt ctagctgtaa aagtcttcta   11400
cagttaccca ttgattaaat ggtttatgtt tataaccgtc tgcttggtaa gctggcatgt   11460
attctgtacc cgttacaggg tctaaccatg tttcaataac atatggtgta ccagttgcag   11520
gtgctctaaa gttatctaga gactcagtat ctaaaccact agttcctaat ccttgggcca   11580
ctaggtacat ttcttcttta tcgtcattac cgtataacgt gaacacaacg ggataccatt   11640
ttttaacttg tgcgttgtta tcaaattggt ggaagtcatt cattgtgata gcattgtttg   11700
atagaacatg tttcaaccta tcagttacac cctctgcgta aatgtctaac atgaaataat   11760
acatgtctgc aacttgttca ggccacccag tgcctctaaa tgtcatatgc cagatgtcta   11820
acaaaaggaa ttcaaaacgt ttagtaacgc cccgcacttg gaatgtatgg gattgatata   11880
gtaggttcat tccgccgtta gggtcaatct gcgtaccagt gctagcattt ccaactgggt   11940
taaacctaat agcttttgac ccctcacgac taccgaatgt tgctaagctg ttcatcattt   12000
ctgtatatgt tgaaatttgt ttcacaccta gaatatctgc gtctaacaat tcaatctttt   12060
gtgttagtgg gtcaatatct ggtatgtcaa gagcaattaa tcgttttttcc atgttatcaa   12120
tttgaagttt tagacctgcg tcagcttctc cgaattcctg cgataaattc tcaatcatag   12180
ctcggatttg ttccattgtt acgtctgaac cctctggcgt tagaatttca tcaattagtt   12240
gctcaatttc agcaatttta gatgtgtagt caacgacgtg taacccgtca gttgtgattt   12300
ttaaaccgtt atctgattgt ggtgctacct taacatctac ctgaatgcca ttatagatat   12360
ttgacttggc tgttgatgtt tcagcaccct ttaaattacc aagaagattt ttattctcgg   12420
ccgcttgggc agcaacttcg tcaatttgtt gaatgatttc aaggtcggca tttttttaaat   12480
cttgtacgtc tttatcgtga ccatcaagtc taccgtcttg ttcgatattc tttttcactgt   12540
tagcgttaat agcgtctgct actgccttac taaattgtaa ttctttccaa tgttcatggt   12600
cgtgatgtga catgtggtcg tgatgttggt caaatggatt gatataaaat ttcatataat   12660
tagtacccct catagaatag ttggctgaat aatttaatat ctagctcatc aaaaatcttc   12720
tgcttaaatg cttcgtattc ttctaaagct ttagtgttaa attgtgtgtt ggttgaattt   12780
gaattattgt tactacttcc ctgactacta ctgatacctt ttgaatgtga tacgttaaca   12840
ctttcgttat agctcttatc aaggttatct gcatagctta ggttagctgt ttctaggtcg   12900
gtatcggtta catcatcagg gtttgttgag tgagcgttag ctcctctgtt ttcaccgtta   12960
```

-continued

```
ctttcgtttg tgctgttatc tcgacttcta ttctcattag atgaatgtcc ctcactctta    13020
gacatgcttt cacctaataa taattctgtt gattttaagt acaacatatt tagcacagct    13080
tcttttgttt ttagtattcc ttttagtttc gctctaaaga tgtatagact gtcccaatgt    13140
ggctctctgt taaagaagta gttaacgaat tcctctctaa agtcttcgtt taccttgctg    13200
ccagtgaaga taagttcatt aacaaccttt tgtacatctt catcatacat cattatcttt    13260
gtttcaattt gtgctttgtc ctcaaacact acaattctat tttcagggct gcggaacggt    13320
gaataaccgt tctttaccac ttctttataa attaactcga ataatctcat tgtgctacct    13380
cgcttacaat ttgaagcttc tcaatacttg ataattcagc aaccatatta tccctgtatt    13440
cagcatgaat attaaggccg tatttattat taataaggtt taaggcttcg ttgcgaattc    13500
caagataaat gttttcgttt gctttcttaa aggctgtatt ggattgggct tcaatttctg    13560
atacgccact ttctttatca actcctagag tatttagtcc tagcattgca ttcaattcag    13620
aaattttatt ctgttgttca cgtttcaatt ctggtaagaa tgaaacagcc gaggcattat    13680
tgaatgttag tatatgttcc tctgggtcga atttaggcgt tgttgctgta aaggtacac    13740 cgttaaaaag attattggcc atgacttgac cgtctttgct gccaccctca ttacgtataa    13800
aggtattaac cttagcttga atggaaatac tataccttga attggctatt tcagacattt    13860
ccataacata atgtgtaata atgttataat cgcacaagaa actagctctt tgttacgta    13920 atacaacaaa attaccatca ctgtatcttg ttagctcttt atactttcct ttgggtagta    13980
tgttattgtg aatgaatgtg atgtctttgc cttgtagagg ctctttaatt ggttgtaagt    14040
aatttgtatt tacagaacaa tatcctagta cgtcaatctt accagtttta gtttcaccga    14100
tggccacccc gtacccagca cgtaaataac tttcgattag taaactatct aaatcatagt    14160
tttcatatga aattagtagt ggtaggaatt ctacatatct actataaata atattaaagt    14220
agttttgttt atgtaacttt acccttcag ctatatcatc tgtaaaagta gacattttgt    14280
aattcatttc actaggctta attcctgatg tgatttgcat gtataccct ttctatataa    14340 aaacagagga cttgcgccct cgttaattag ttagcacgct taattactac cttattgtag    14400
aaaggactaa tagctttcat tgagtagtag tgaatccaat gtgttacttc gtcaaactca    14460
ccgttataga atggtgcttt caacatgtta cgtgtataac gtttgtaacg aattgaacgt    14520
acatcgaaaa ttgctacaaa ttcatcactg tcaggtttaa cttcgactag agcgtcagct    14580
tggtcgccca gagcttctgc gggaatttcg taagtgaata ctgttcctgc tgggataaca    14640
tcacctgctt taacttggta gtctcccatg gcagccatca caccttgaat agttgcgtcg    14700
actgtaatgt cctcggctgc tttatataca ccgcctaagt cttcaaaaga gataatttgt    14760
gatgtaatat ccaatccctc tgcgtggaat gtgttagcaa ggaagctgtt taggatttca    14820
actttcattt cgtcagttgt aacaattaac atatccttta gttttgtgtt tgttgtaaaa    14880
cgtccgactg cacctcctga agcttgtgca gcttcgttat gcttagcaga gttgttttgt    14940
aagttaagga tagctgtata aactttgttg atgaattgtt gcattgtagc acctgattca    15000
acttcacgta cgtctgcaat gtgacttgtg tagtccataa taatagcctt tagctcttgt    15060
tcctctgaaa tgttaatatc agcgattttc tttttgtaga cttgtactgc aaactttgtt    15120
gcgtctccta gagtagcaaa ttgttgacgt tggatattgt cattaagagt gaatttaagt    15180
tttttaagaa tacctgcacc gtacaactta gaagcaattt ttggatagtt gcgttctagc    15240
ataagttgtg ctgattttga taagtcaagt tcaactggga cggtgtcaag gataacgtat    15300
tcttctgaat attgtccgat aaagtcaatt tcttttgcta gccaatctaa acggttacct    15360
```

```
gctgctgttt caacaattag ggtctcgttc aatttaggga aaagatattg attagtatat    15420
gtctcgaagt ctgtaccaac tgcattccaa ttagtaccga atgtccaaga tttaccgtta    15480
tctgcgttaa aatcgttaag tgaagcgaca atagcgccag ctacgtttgt agtttcatct    15540
gccataatat ataattctcc tattttctat tttttctatt tattataagt taaacaaagc    15600
tgttgttact tcgtcttgtg atttaccttg gccaatcgtc atagtttcgt taagttcatt    15660
tgacttatcg agctttgaaa taccgaagtc atctttggtc atgttgtgga ttgtgtttgt    15720
gtgttcttct ggtagcatgt tattagtcct cctttaacca ttcttcaatt tcgtcaattg    15780
gtgtaacttc tggctcttgt tcttcttgct gttttggttc atcagcagga gcaggagcgg    15840
tagctagttc ttcaagacgt gctgtctttt cttcaagagc tgcaatctta gctagtagtt    15900
cttctttcgt cattaaatag tctcctttca aaataaaata tcggtatttt tacttggtta    15960
tccgataaac aaagttaggt ctagggttcg tctaattatg tgcttatagt ctcgtatgac    16020
ctcaattcta attaataact cttccctatt tccttactac tctttaatta tatcaaacta    16080
ttttagatat gtcaagcttt tttatttaat ttcttttgtt tcgtagaaat agtctttaat    16140
catatcaccg tcattttaa gagttagcat aactttgtct ctatcctcta catcacgagt     16200
aacgtatact ttaatccatt taccattaac atatgcgtag atgtggtact catagttttt    16260
accgtcttgt tcctctagtg gtttgttttc agccatttgt attctccttt ccttattgtt    16320
atatatagta taacaaattg tttcgtgatt gtcaactgtt ttatttgaag ttttaaatt     16380 tattttataa tgtcgtaaac cattgttacg ccctcattgt tcatagtgaa gctgactacc    16440
ttaacatttt ccataccata agttgcaacc tcatgtgcat atatatcgcg tagcgtgtca    16500
atgcttgttt cggttactga tatgtgtgtt gttcgtgtgt ggttcatgtt gtgtacctct    16560
ttcttattta tgtattaatt atatcatgtt gcagctgtgg tgtcaacaga aatatttatg    16620
aaagtgtttt ctgaaaacat ttacattagg agggggagg gagaaatcac tacgctatat     16680
actaaaa                                                              16687

<210> SEQ ID NO 22
<211> LENGTH: 219
<212> TYPE: DNA
<213> ORGANISM: Bacteriophage C1 light chain of PlyC (PlyC B)
      (formerly known as gene for alpha subunit)

<400> SEQUENCE: 22
atgagcaaga ttaatgtaaa cgtagaaaat gtttctggtg tacaaggttt cctattccat       60
accgatggaa agaaagtta cggttatcgt gctttatta acggagttga aattggtatt        120
aaagacattg aaaccgtaca aggatttcaa caaattatac cgtctatcaa tattagtaag      180
tctgatgtag aggctatcag aaaggctatg aaaaagtaa                             219

<210> SEQ ID NO 23
<211> LENGTH: 1419
<212> TYPE: DNA
<213> ORGANISM: Bacteriophage C1 heavy chain of PlyC (PlyC A)
      (formerly known as gene for beta subunit)

<400> SEQUENCE: 23
atgaaaggga gaatttattt aatgagtaag aagtatacac aacaacaata cgaaaaatat       60
ttagcacaac cagcaaataa cacatttggg ttatcacctc aacaggttgc tgattggttt      120
atgggtcaag ctggtgctag gcctgttatt aactcgtatg gggtaaatgc tagtaattta      180
```

-continued

| | |
|---|---|
| gtatcaacgt acatacctaa aatgcaggaa tacggtgtat catatacact attcttaatg | 240 |
| tatactgtct ttgagggagg cggcgcaggt aattggatta atcattacat gtacgatacg | 300 |
| gggtctaatg gattagagtg tttggaacac gatttacaat acatacatgg cgtctgggaa | 360 |
| acttattttc caccagcttt atctgcgcca gaatgttacc cagctacgga agataacgca | 420 |
| ggtgctttag atagattta tcaatcgcta ccaggccgaa catggggtga tgttatgata | 480 |
| cctagtacaa tggctggtaa tgcttgggta tgggcttata actattgtgt taacaaccaa | 540 |
| ggggctgccc cattagttta ctttggcaat ccatacgata gtcaaattga tagcttgctt | 600 |
| gcaatgggag ctgacccgtt tacaggtggt tcaattacag gtgatggaaa aaatcctagt | 660 |
| gttggcactg ggaatgctac cgtttctgct agctcggaag ctaacagaga gaagttaaag | 720 |
| aaagccctaa cagattatt caacaacaac ctagaacatc tatcaggtga attctacggt | 780 |
| aaccaagtgt tgaatgctat gaaatacggc actatcctga atgtgatt aacagatgac | 840 |
| ggacttaatg ccattcttca attaatagct gatgttaact tacagactaa ccctaaccca | 900 |
| gacaaaccga ccgttcaatc accaggtcaa aacgatttag ggtcggggtc tgatagagtt | 960 |
| gcagcaaact tagccaatgc acaggcgcaa gtcggtaagt atattggtga cggtcaatgt | 1020 |
| tatgcttggg ttggttggtg gtcagctagg gtatgtggtt attctatttc atactcaaca | 1080 |
| ggtgacccaa tgctaccgtt aattggtgat ggtatgaacg ctcattctat ccatcttggt | 1140 |
| tgggattggt caatcgcaaa tactggtatt gttaactacc cagttggtac tgttggacgc | 1200 |
| aaggaagatt tgagagtcgg cgcgatatgg tgcgctacag cattctctgg cgctccgttt | 1260 |
| tatacaggac aatacggcca tactggtatc attgaaagct ggtcagatac taccgttaca | 1320 |
| gtcttagaac aaaacattt agggtcacca gttatacgca gcacctatga ccttaacaca | 1380 |
| ttcctatcaa cactaactgg tttgataaca tttaaataa | 1419 |

<210> SEQ ID NO 24
<211> LENGTH: 318
<212> TYPE: DNA
<213> ORGANISM: Bacteriophage C1 lysin intergenic locus(lil)

<400> SEQUENCE: 24

| | |
|---|---|
| atgattgagg agtgggtcaa gcaccctcc ctcaattact atataagtag ttatggcagg | 60 |
| gtgaaaaact ctaaaggttt aataatgaaa caacacatat gcaatggtta taagcgaatt | 120 |
| aaattagtaa aggacggtat aaaaagaat tactatgttc atcgcttagt tgcagaaaca | 180 |
| ttcataccta aactacatgt tgactatgtt gtacatcata ttgaccatga taaactaaac | 240 |
| aactgggtac ataacttaga atggtgtcat tatcaaacta acctattata tgaaagggag | 300 |
| aatttatta atgagtaa | 318 |

<210> SEQ ID NO 25
<211> LENGTH: 2213
<212> TYPE: DNA
<213> ORGANISM: Bacteriophage C1 PlyC operon

<400> SEQUENCE: 25

| | |
|---|---|
| gaagtaattt ccattcttga aaacgtcgca tggtacttac cagtgccaaa gaaactgcta | 60 |
| aatgttttag cacaatttaa agaaatagaa aatgaggtaa aatcaaatga gcaagattaa | 120 |
| tgtaaacgta gaaaatgttt ctggtgtaca aggtttccta ttccataccg atggaaaaga | 180 |
| aagttacggt tatcgtgctt ttattaacgg agttgaaatt ggtattaaag acattgaaac | 240 |
| cgtacaagga tttcaacaaa ttataccgtc tatcaatatt agtaagtctg atgtagaggc | 300 |

```
tatcagaaag gctatgaaaa agtaatgatt gaggagtggg tcaagcaccc ctccctcaat      360
tactatataa gtagttatgg cagggtgaaa aactctaaag gtttaataat gaaacaacac      420
atatgcaatg gttataagcg aattaaatta gtaaaggacg gtataaaaaa gaattactat      480
gttcatcgct tagttgcaga acattcata cctaaactac atgttgacta tgttgtacat       540
catattgacc atgataaact aaacaactgg gtacataact tagaatggtg tcattatcaa      600
actaacctat tatatgaaag ggagaattta tttaatgagt aagaagtata cacaacaaca     660
atacgaaaaa tatttagcac aaccagcaaa taacacattt gggttatcac ctcaacaggt      720
tgctgattgg tttatgggtc aagctggtgc taggcctgtt attaactcgt atggggtaaa     780
tgctagtaat ttagtatcaa cgtacatacc taaaatgcag gaatacggtg tatcatatac     840
actattctta atgtatactg tctttgaggg aggcggcgca ggtaattgga ttaatcatta     900
catgtacgat acgggtcta atggattaga gtgtttggaa cacgatttac aatacataca     960
tggcgtctgg gaaacttatt ttccaccagc tttatctgcg ccagaatgtt acccagctac     1020
ggaagataac gcaggtgctt tagatagatt ttatcaatcg ctaccaggcc gaacatgggg    1080
tgatgttatg atacctagta caatggctgg taatgcttgg gtatgggctt ataactattg    1140
tgttaacaac caaggggctg ccccattagt ttactttggc aatccatacg atagtcaaat   1200
tgatagcttg cttgcaatgg gagctgaccc gtttacaggt ggttcaatta caggtgatgg   1260
aaaaaatcct agtgttggca ctgggaatgc taccgtttct gctagctcgg aagctaacag   1320
agagaagtta aagaaagccc taacagattt attcaacaac aacctagaac atctatcagg   1380
tgaattctac ggtaaccaag tgttgaatgc tatgaaatac ggcactatcc tgaaatgtga   1440
tttaacagat gacggactta atgccattct tcaattaata gctgatgtta acttacagac   1500
taaccctaac ccagacaaac cgaccgttca atcaccaggt caaaacgatt tagggtcggg  1560
gtctgataga gttgcagcaa acttagccaa tgcacaggcg caagtcggta agtatattgg  1620
tgacggtcaa tgttatgctt gggttggttg gtggtcagct agggtatgtg gttattctat  1680
ttcatactca acaggtgacc caatgctacc gttaattggt gatggtatga acgctcattc  1740
tatccatctt ggttgggatt ggtcaatcgc aaatactggt attgttaact acccagttgg  1800
tactgttgga cgcaaggaag atttgagagt cggcgcgata tggtgcgcta cagcattctc  1860
tggcgctccg ttttatacag gacaatacgg ccatactggt atcattgaaa gctggtcaga  1920
tactaccgtt acagtcttag aacaaaaacat tttagggtca ccagttatac gcagcaccta  1980
tgaccttaac acattcctat caacactaac tggtttgata acatttaaat aaaaaagaag  2040
agactgtaaa gtctcttttc ttattttata atgacgttat taacaactgt gttattaatc  2100
atgtcacttt ctttgtgcca taaccttaca cctgcttcaa acaaagctct taacatattc  2160
atatgcccag tgtctacgtt aggaagagtc catattccct tgaattgaac cca          2213
```

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26

```
gtacccgggg aagtaatttc cattcttgaa                                       30
```

<210> SEQ ID NO 27

```
<211> LENGTH: 30
<212> TYPE: DNA
<213> ORGANISM: Artificial Sequence
<220> FEATURE:
<223> OTHER INFORMATION: primer

<400> SEQUENCE: 27
cccaagcttt tactttttca tagcctttct                                    30

<210> SEQ ID NO 28
<211> LENGTH: 38
<212> TYPE: DNA
<213> ORGANISM: Artificial Sequence
<220> FEATURE:
<223> OTHER INFORMATION: primer

<400> SEQUENCE: 28
gtaccgggga ggaggaattc atgattgagg agtgggtc                           38

<210> SEQ ID NO 29
<211> LENGTH: 36
<212> TYPE: DNA
<213> ORGANISM: Artificial Sequence
<220> FEATURE:
<223> OTHER INFORMATION: primer

<400> SEQUENCE: 29
gggaagcttt tactcattaa ataaattctc cctttc                             36

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
gtacccggga aagggagaat ttatttaatg                                    30

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
cccaagcttt gggttcaatt caagggaata                                    30
```